(12) United States Patent
Suzuki et al.

(10) Patent No.: US 7,986,824 B2
(45) Date of Patent: Jul. 26, 2011

(54) PREDETERMINED SITE LUMINESCENCE MEASURING METHOD, PREDETERMINED SITE LUMINESCENCE MEASURING APPARATUS, EXPRESSION AMOUNT MEASURING METHOD, AND MEASURING APPARATUS

(75) Inventors: Hirobumi Suzuki, Hino (JP); Yoko Ohashi, Tokyo (JP); Kenji Kawasaki, Hachioji (JP); Kiyotsugu Kojima, Yokohama (JP); Kenichi Koyama, Sagamihara (JP); Akihiko Yoshikawa, Hachioji (JP)

(73) Assignee: Olympus Corporation, Tokyo (JP)

( * ) Notice: Subject to any disclaimer, the term of this patent is extended or adjusted under 35 U.S.C. 154(b) by 968 days.

(21) Appl. No.: 11/887,468

(22) PCT Filed: Mar. 30, 2006

(86) PCT No.: PCT/JP2006/306755
§ 371 (c)(1),
(2), (4) Date: Sep. 28, 2007

(87) PCT Pub. No.: WO2006/106882
PCT Pub. Date: Oct. 12, 2006

(65) Prior Publication Data
US 2009/0274360 A1    Nov. 5, 2009

(30) Foreign Application Priority Data

Mar. 30, 2005  (JP) ................. 2005-098608
Mar. 31, 2005  (JP) ................. 2005-104341
Apr. 28, 2005  (JP) ................. 2005-133231
Nov. 22, 2005  (JP) ................. 2005-337608

(51) Int. Cl.
*G06K 9/00*    (2006.01)

(52) U.S. Cl. ........................ 382/133; 382/286

(58) Field of Classification Search .......... 382/109, 382/110, 128–134, 141–154, 168–170, 181, 382/274–275, 286, 325
See application file for complete search history.

(56) References Cited

U.S. PATENT DOCUMENTS 5,485,530 A * 1/1996 Lakowicz et al. ............. 382/191
(Continued)

FOREIGN PATENT DOCUMENTS

EP    1 457 571    9/2004
(Continued)

OTHER PUBLICATIONS

Mullaney J M et al., "Activity of Foreign Proteins Targeted Within the Bacteriophage T4 Head and Prohead: Implications for Packaged DNA Structure", Journal of Molecular Biology, London, GB, vol. 283, No. 5, Nov. 13, 1998, pp. 913-929, XP004462337.

(Continued)

*Primary Examiner* — Manav Seth
(74) *Attorney, Agent, or Firm* — Scully, Scott, Murphy & Presser, P.C.

(57) ABSTRACT

An object of the present invention is to provide a predetermined site luminescence measuring method and a predetermined site luminescence measuring apparatus, which allow for determining whether, when the luminescence from the predetermined site in live samples is measured, a photoprotein is localized at the predetermined site in the same ones as the samples. An predetermined site luminescence measuring apparatus 100 in the present invention is comprised of: a the sample 102 into which a fused gene is introduced, the fusion gene being obtained by fusing a fluorescence-related gene that expresses a fluorescence protein in addition to a targeting base sequence and a luminescence-related gene; a container 103 for storing the sample 102, a stage 104 on which the container 103 is arranged; a luminescent image capturing unit 106 which captures a luminescent image of the sample 102 (the objective lens 106a to the CCD camera 106c, and the imaging lens 106f); a fluorescent image capturing unit 108 which captures a fluorescent image of the sample 102 (the objective lens 108a to shutter 108f); and an the information communication terminal 110.

37 Claims, 27 Drawing Sheets

U.S. PATENT DOCUMENTS

| | | | |
|---|---|---|---|
| 5,976,796 | A | 11/1999 | Szalay et al. |
| 6,271,022 | B1 * | 8/2001 | Bochner .................... 435/287.3 |
| 6,608,918 | B1 * | 8/2003 | Rushbrooke et al. ......... 382/133 |
| 6,671,624 | B1 * | 12/2003 | Dunlay et al. .................. 702/19 |
| 6,800,249 | B2 * | 10/2004 | de la Torre-Bueno .......... 422/63 |

FOREIGN PATENT DOCUMENTS

| | | |
|---|---|---|
| EP | 1 935 987 A1 | 6/2008 |
| FR | 2 840 320 | 12/2003 |
| JP | 10-339875 | 12/1998 |
| JP | 2001-501100 | 1/2001 |
| JP | 2001-319952 | 11/2001 |
| JP | 2002-055282 | 2/2002 |
| JP | 2002-335997 | 11/2002 |
| JP | 2003-180393 | 7/2003 |
| JP | 2005-531303 | 10/2005 |

OTHER PUBLICATIONS

Molina A et al., "A transformed fish cell line expressing a green fluorescent protein-luciferase fusion gene responding to cellular stress", Toxicology in Vitro, vol. 16, No. 2, Apr. 2002, pp. 201-207, XP002554656.

Ponomarev Vladimir et al., "A novel triple-modality reporter gene for whole-body fluorescent, bioluminescent, and nuclear noninvasive imaging", European Journal of Nuclear Medicine and Molecular Imaging May 2004, vol. 31, No. 5, pp. 740-751, XP002554657.

Extended Supplementary European Search Report dated Dec. 16, 2009.

H. J. Kennedy, et al. "Glucose generates sub-plasma membrane ATP microdomains in single islet β-cells.", Journal of Biological Chemistry, vol. 274, pp. 13281-13291, 1999.

English-language abstract of International Patent Publication No. WO 03/102176, dated Dec. 11, 2003.

European Office Action dated Oct. 8, 2010, issued in corresponding European Patent Application No. 06730703.3.

* cited by examiner

US 7,986,824 B2

PREDETERMINED SITE LUMINESCENCE MEASURING METHOD, PREDETERMINED SITE LUMINESCENCE MEASURING APPARATUS, EXPRESSION AMOUNT MEASURING METHOD, AND MEASURING APPARATUS

TECHNICAL FIELD

The present invention relates to a predetermined site luminescence measuring method and a predetermined site luminescence measuring apparatus, that measure the luminescence from a predetermined site in a live sample.

The present invention also relates to an expression amount measuring method that includes identifying the stage of the cell cycle in living cells into which a gene to be analyzed are introduced using fluorescence measurement in combination with luminescence measurement, and measuring the amount of expression of the gene to be analyzed.

The present invention further relates to a measuring apparatus that captures an image of a specimen for observation, and more particularly to a measuring apparatus that is preferably used to observe a specimen labeled with a luminescent label emitting weak luminescence or a fluorescent label emitting fluorescence by excitation.

BACKGROUND ART (I) ATP is a source of intracellular energy as well as a substance deeply involved in the life process. On the other hand, firefly luciferase catalyzes the reaction of forming oxyluciferin, $CO_2$, AMP, and pyrophosphoric acid through D-luciferin as a luminescent substrate in the presence of ATP, $O_2$, and $Mg^{2+}$, thereby producing luminescence. Further, the luminescent reaction of luciferase depends on the amount of ATP.

Therefore, an assay to quantify ATP using the luminescent reaction of luciferase has been used since a long time ago. In fields, such as biotechnology, clinical laboratory test, and food hygiene, methods for measuring the amount of intracellular ATP using luciferase have been developed.

For example, the amount of intracellular ATP is usually measured by the following steps (1-1) to (1-3):
(1-1) dissolving cells or bacteria to extract ATP;
(1-2) adding the extracts to a reaction solution containing luciferin and luciferase; and
(1-3) quantifying the amount of intracellular ATP by measuring the luminescence from the reaction solution to which the extracts are added.

The amount of ATP in the cells which are not homogenized is usually measured by the following steps (2-1) to (2-3):
(2-1) introducing a luciferase gene into cells to obtain expression thereof;
(2-2) adding luciferin to a culture solution containing cells; and
(2-3) quantifying intracellular ATP by measuring the luminescence from the culture solution to which luciferin is added.

The serial measurement of the amount of ATP at a predetermined site (specifically, mitochondria) in living cells is performed by the following steps (3-1) and (3-2) (Non-patent document 1):
(3-1) fusing a mitochondrial targeting signal gene to a luciferase gene and introducing the fused gene into cells; and
(3-2) sequentially measuring changes of the amount of ATP in mitochondria in the cells by measuring the luminescence from the cells on the presupposition that luciferase is localized in mitochondria in the cells.

Since the intensity of luminescence emitted from cells is very weak, photon counting is performed by using a CCD camera equipped with an image intensifier to recognize one cell. Cells other than the cells whose amount of luminescence is measured are used to determine whether luciferase is localized in mitochondria in cells or not. Specifically, the different cells are immobilized and reacted with anti-luciferase antibodies, and then the cells are observed by a fluorescent antibody method in order to confirm their localization. As a result, it is suggested that the amount of luminescence from the measured cells corresponds to the amount of luminescence from mitochondria.

(II) The cell proliferation is one of the essential and important characteristics for organisms in the vital life processes. The cell cycle includes multiple consecutive reactions consisting of the growth of cells, the DNA duplication, the distribution of chromosomes, the cell division, and the like. Therefore, it is just conceivable that the expression of various genes varies depending on each stage of the cell cycle. Further, it is considered that abnormality or disruption of the cell cycle is involved in numerous chronic diseases and oncogenesis (refer to Patent document 1). In addition, Patent document 1 discloses a technique relative to a method of measuring the activity of a cell-cycle regulator and a method of diagnosing cancer using thereof.

Incidentally, when the luciferase gene is introduced into cells as a reporter gene and the strength of expression of the luciferase gene is examined using the luciferase activity as an indicator, the effect of a target DNA fragment on the transcription of the luciferase gene can be examined by linking the target DNA fragment to upstream or downstream of the luciferase gene. Further, a gene such as a transcription factor, considered to affect the transcription of luciferase gene, is linked to an expression vector and coexpressed with the luciferase gene, thereby enabling to examine the effect of a gene product of the gene on the expression of the luciferase gene. In this regard, examples of the method of introducing a reporter gene such as a luciferase gene into cells include a calcium phosphate method, a Lipofectin method, and an electroporation method. Each method is used separately depending on the purpose or the difference in the type of cell.

Further, the activity of the luciferase which is introduced into cells and is expressed is measured (monitored) by the steps of reacting a cell lysate in which the cells are dissolved with a substrate solution containing luciferin, ATP, magnesium, or the like, and then quantifying the amount of luminescence from the cell lysate reacted with the substrate solution using a luminometer with a photomultiplier tube. That is, the luminescence is measured after dissolving the cells. Thus, the amount of expression of the luciferase genes at a certain point in time can be measured as an average value of the whole cells.

In order to catch the amount of expression of luciferase genes with time, it is necessary to measure the luminescence from living cells sequentially. The serial measurement of the luminescence from living cells is performed by the steps of adding a luminometer function to an incubator for culturing cells, and then quantifying the amount of luminescence from whole cell populations while culturing at regular time intervals using a luminometer. This allows for measuring the expression rhythm with a regular cycle, and the like. Thus, it is possible to catch changes over time of the amount of expression of luciferase genes in whole cells.

However, in the conventional reporter assay as described above, multiple cells at different stages of the cell cycle are mixed, so that the cells at various stages have been handled as a group of data. Therefore, the operation of synchronized culture is performed to match the stages of the cell cycle when the gene in connection with the cell cycle is analyzed.

(III) Conventionally, a microscope apparatus that can observe a specimen by switching imaging magnification of a specimen image from a high magnification mode to a low magnification mode, has commonly been used. With reference to such a microscope apparatus, there has been recently proposed a microscope apparatus in which a visual field of observation at low magnification is not limited by an objective lens with high magnification and the overall image of a specimen can be grasped in a wider visual field (for example, refer to Patent document 2). In the microscope apparatus disclosed in Patent document 2, when a specimen is observed at low magnification, the specimen image is formed using an imaging lens for low magnification, in which the focal depth is deeper than the conventional one, namely, NA (Numerical Aperture) on the side of the specimen is smaller than the conventional one without the objective lens with high magnification.

Patent document 1: Japanese Patent Application Laid-Open (JP-A) No. 2002-335997

Patent document 2: JP-A No. 10-339845

Non-patent document 1: H. J. Kennedy, A. E. Pouli, E. K. Ainscow, L. S. Jouaville, R. Rizzuto, G. A. Rutter, "Glucose generates sub-plasma membrane ATP microdomains in single islet β-cells.", Journal of Biological Chemistry, vol. 274, pp. 13281-13291, 1999

DISCLOSURE OF INVENTION

Problem to be Solved by the Invention (I) However, in the conventional technology, cells other than the cells whose amount of luminescence is measured are used to determine whether a photoprotein is localized at a predetermined site in cells or not. Additionally, since cells die when they are confirmed by a fluorescent antibody technique, it is not always known whether a photoprotein is localized at a predetermined site in living cells which are subject to the measurement of luminescence. Therefore, it is not necessarily clear that the amount of luminescence from the cells is that from a predetermined site, which is a problem.

Particularly, when a gene is transiently introduced into cells, the gene is not introduced into all the cells. Thus, it is necessary to confirm whether the gene has been introduced into the living cells themselves which are subject to the measurement of luminescence and whether a photoprotein is localized at a predetermined site in the cells into which the gene has been introduced.

The present invention has been achieved in view of the above-mentioned problems. An object of the present invention is to provide a predetermined site luminescence measuring method, and a predetermined site luminescence measuring apparatus, which allow for determining whether, when the luminescence from the predetermined site in live samples is measured, a photoprotein is localized at the predetermined site in the same ones as the aforementioned samples.

(II) However, the operation of synchronized culture in the conventional technology is complicated, which resulted in a heavy procedural burden on experimenters.

The present invention has been achieved in view of the above-mentioned problem. Another object of the present invention is to provide an expression amount measuring method, in which when the amount of expression of genes which are introduced into cells for analysis is measured, the stage of the cell cycle can be identified without performing the synchronized culture method, resulting in reducing the procedural burden on experimenters.

(III) Meanwhile, in recent years, there has been a great need to observe biological cells by using GFP (Green Fluorescent Protein) or a luciferase gene, i.e. a bioluminescent enzyme, as a reporter of expression and labeling an intracellular predetermined site or a functional protein with fluorescence or luminescence in research areas, such as cell biology and molecular biology. Usually, in order to catch time-dependent change in expression in observing such cells, it is necessary to continue to observe cells on the time series.

However, GFP is a protein which emits fluorescence depending on irradiation of excitation light and a specimen activated by GFP is irradiated with the excitation light with high intensity to give fluorescence. Thus, with reference to the observation using GFP, the specimen is easily damaged and the observation is limited to about 1 hour to 2 hours. Compared with this, in the observation using a luciferase gene, the observation can be performed for about several days to several weeks because the luciferase gene is a self-luminous enzyme and does not damage a specimen. Thus, it is desired that continuous observation using a luciferase gene is performed over time and the time-dependent change in a specimen is caught by properly switching to the observation using GFP depending on this result of the observation using a luciferase gene.

However, the light emitted from the luciferase gene is very weak. For this reason, as for the observation of fluorescence, for example, when observing fluorescence from GFP, the weak luminescence from a luciferase gene cannot be observed using an imaging optical system with high magnification to be used usually or a conventional imaging optical system with low magnification in which both NA on the specimen side and NA on the image side are small. A microscope apparatus that combines the observation of fluorescence and the observation of weak luminescence by weak luminescence has not been realized yet. Further, a microscope apparatus that can immediately switch to the observation of fluorescence depending on the result of continuous observation according to the observation of weak luminescence has not been developed, either.

The present invention has been achieved in view of the above circumstances. Still another object of the present invention is to provide a measuring apparatus which can switch between observation of weak luminescence and observation of fluorescence properly and can switch to the observation of fluorescence immediately depending on the results of observation of weak luminescence.

Means for Solving Problem

To solve the above problems and to achieve the above objects, according to one aspect of the present invention, a predetermined site luminescence measuring method measures the luminescence from a live sample into which a fusion gene is introduced, the fusion gene being obtained by fusing a targeting base sequence that directs a photoprotein to a predetermined site in the sample and a luminescence-related gene that expresses the photoprotein, in order to obtain the amount of luminescence from the predetermined site, wherein the fusion gene is obtained by further fusing a fluorescence-related gene that expresses a fluorescence protein with the targeting base sequence, and the luminescence-related gene. The method includes a fluorescent image capturing step of capturing a fluorescent image of the sample into which the fusion gene is introduced, a determining step of determining whether the photoprotein is localized at the predetermined site based on the fluorescent image captured at the fluorescent image capturing step, and a luminescence measuring step of measuring the luminescence from the sample when the localization is determined as a result of the determining step.

According to another aspect of the present invention, the predetermined site luminescence measuring method further includes a luminescent image capturing step of, when multiple live samples into which the fusion gene is introduced are present in an area to be captured, capturing a luminescent image of the samples, and a selecting step of selecting a sample for measurement from the samples in which the localization is determined as the result of the determining step by superimposing the fluorescent image captured at the fluorescent image capturing step and the luminescent image captured at the luminescent image capturing step, wherein the fluorescent image capturing step includes capturing the fluorescent image of the samples, the determining step includes determining whether the photoprotein is localized at the predetermined site based on the fluorescent image for each sample, and the luminescence measuring step includes measuring the luminescence from the sample selected at the selecting step.

According to still another aspect of the present invention, in the predetermined site luminescence measuring method, the amount of luminescence from the predetermined site in the sample is obtained sequentially by repeatedly performing the fluorescent image capturing step, the determining step, the luminescent image capturing step, the selecting step, and the luminescence measuring step.

According to still another aspect of the present invention, the predetermined site luminescence measuring method further includes a luminescence separation step of separating luminescence from the sample in accordance with luminescent color, wherein multiple fusion genes to be introduced into the samples are prepared in advance so that each combination of a targeted site to which the photoprotein is directed by the targeting base sequence, a luminescent color of luminescence emitted from the photoprotein, and a fluorescent color of fluorescence emitted from the fluorescence protein is different, the determining step includes determining whether a photoprotein is localized at the predetermined site for each fluorescent color based on the fluorescent image, and the luminescence measuring step includes, when the localization is determined as a result of the determining step, specifying luminescence from the site where the localization is determined among the multiple luminescence separated at the luminescence separation step, and measuring the specified luminescence.

According to still another aspect of the present invention, in the predetermined site luminescence measuring method, the sample is any one of a test sample, a tissue, a cell, and an individual.

According to still another aspect of the present invention, the predetermined site luminescence measuring method further includes an ATP quantifying step of quantifying ATP at the predetermined site in the samples selected at the selecting step based on the amount of luminescence measured at the luminescence measuring step, wherein the sample is a cell, the predetermined site is mitochondria, the targeting base sequence is a mitochondrial targeting signal, the photoprotein is luciferase, and the fluorescence protein is a green fluorescent protein, and ATP at the predetermined site in the sample is quantified sequentially by repeatedly performing the fluorescent image capturing step, the determining step, the luminescent image capturing step, the selecting step, the luminescence measuring step, and the ATP quantifying step.

According to still another aspect of the present invention, a predetermined site luminescence measuring apparatus measures the luminescence from a live sample into which a fusion gene is introduced, the fusion gene being obtained by fusing a targeting base sequence that directs a photoprotein to a predetermined site in the sample and a luminescence-related gene that expresses the photoprotein, in order to obtain the amount of luminescence from the predetermined site, wherein the fusion gene obtained by further fusing a fluorescence-related gene that expresses a fluorescence protein with the targeting base sequence, and the luminescence-related gene. The apparatus includes a fluorescent image capturing unit that captures a fluorescent image of the sample into which the fusion gene is introduced, a determining unit that determines whether the photoprotein is localized at the predetermined site based on the fluorescent image captured by the fluorescent image capturing unit, and a luminescence measuring unit that measures the luminescence from the sample when the localization is determined as a result of the determining unit.

According to still another aspect of the present invention, an expression amount measuring method includes a luminescence measuring step of measuring luminescence intensity of luminescence emitted from a living cell into which a luminescence-related gene which expresses a photoprotein, a fluorescence-related gene which expresses a fluorescence protein, and a gene to be analyzed are introduced, a fluorescence measuring step of measuring fluorescence intensity emitted from the cell, and an expression amount measuring step of measuring the amount of expression of the gene to be analyzed based on the luminescence intensity measured at the luminescence measuring step or the fluorescence intensity measured at the fluorescence measuring step, wherein the cell is a cell into which a cell cycle-related gene which expresses at a predetermined stage of the cell cycle is further introduced in addition to the luminescence-related gene, the fluorescence-related gene, and the gene to be analyzed. The method further includes a stage identifying step of identifying the stage of the cell cycle by determining the presence or absence of the expression of the cell cycle-related gene based on the fluorescence intensity measured at the fluorescence measuring step when the luminescence intensity is used at the expression amount measuring step, or based on the luminescence intensity measured at the luminescence measuring step when the fluorescence intensity is used at the expression amount measuring step.

According to still another aspect of the present invention, the expression amount measuring method further includes a fluorescent image capturing step of, when multiple cells are present in an area to be captured, capturing a fluorescent image of the cells, and a luminescent image capturing step of capturing a luminescent image of the cells, wherein the luminescence measuring step includes measuring luminescence intensity of luminescence emitted from each cell based on the luminescent image captured at the luminescent image capturing step, the fluorescence measuring step includes measuring fluorescence intensity emitted from each cell based on the fluorescent image captured at the fluorescent image capturing step, the expression amount measuring step includes measuring the amount of expression of the gene to be analyzed in each cell based on the luminescence intensity measured at the luminescence measuring step or the fluorescence intensity measured at the fluorescence measuring step, and the stage identifying step identifies the stage of the cell cycle for each cell by determining the presence or absence of the expression of the cell cycle-related gene for each cell based on the fluorescence intensity measured at the fluorescence measuring step when the luminescence intensity is used at the expression amount measuring step, or based on the luminescence intensity measured at the luminescence measuring step when the fluorescence intensity is used at the expression amount measuring step.

According to still another aspect of the present invention, the expression amount measuring method further includes a selecting step of selecting the cell for measurement from among the cells whose stages are identified at the stage identifying step, wherein the expression amount measuring step includes measuring the amount of expression of the gene to be analyzed which is introduced into the cells selected at the selecting step, based on the luminescence intensity measured at the luminescence measuring step or the fluorescence intensity measured at the fluorescence measuring step.

According to still another aspect of the present invention, in the expression amount measuring method, the amount of expression of the gene to be analyzed is measured sequentially by repeatedly performing the luminescent image capturing step, the fluorescent image capturing step, the luminescence measuring step, the fluorescence measuring step, the stage identifying step, the selecting step, and the expression amount measuring step while the stage of the cell cycle is identified in the cells selected at the selecting step.

According to still another aspect of the present invention, in the expression amount measuring method, the expression amount measuring step includes measuring the amount of expression of the gene to be analyzed in the cell selected at the selecting step based on the fluorescence intensity measured at the fluorescence measuring step, and identifying an expression site of the gene to be analyzed in the cell based on the fluorescent image captured at the fluorescent image capturing step.

According to still another aspect of the present invention, an expression amount measuring method includes a luminescence measuring step of measuring luminescence intensity of luminescence emitted from cells in a living cell into which a luminescence-related gene which expresses a photoprotein and a gene to be analyzed are introduced, and an expression amount measuring step of measuring the amount of expression of the gene to be analyzed based on the luminescence intensity measured at the luminescence measuring step, wherein the cell is stained with a fluorescent substance at the predetermined site. The method further includes a fluorescent image capturing step of capturing a fluorescent image of the cell; and a stage identifying step of identifying the stage of the cell cycle by determining whether the shape of the cell is changed or not based on the fluorescent image captured at the fluorescent image capturing step.

According to still another aspect of the present invention, the expression amount measuring method further includes a luminescent image capturing step of, when multiple cells are present in an area to be captured, capturing a luminescent image of the cells, wherein the fluorescent image capturing step includes capturing a fluorescent image of the cells, the luminescence measuring step includes measuring luminescence intensity of luminescence emitted from each cell based on the luminescent image captured at the luminescent image capturing step, the expression amount measuring step includes measuring the amount of expression of the gene to be analyzed in each cell based on the luminescence intensity measured at the luminescence measuring step, and the stage identifying step includes identifying the stage of the cell cycle by determining whether the shape of the cell is changed or not based on the fluorescent image captured at the fluorescent image capturing step.

According to still another aspect of the present invention, the expression amount measuring method further includes a selecting step of selecting the cell for measurement from among the cells whose stages are identified at the stage identifying step, wherein the expression amount measuring step includes measuring the amount of expression of the gene to be analyzed which is introduced into cells selected at the selecting step, based on the luminescence intensity measured at the luminescence measuring step.

According to still another aspect of the present invention, in the expression amount measuring method, the amount of expression of the gene to be analyzed is measured sequentially by repeatedly performing the luminescent image capturing step, the fluorescent image capturing step, the luminescence measuring step, the stage identifying step, the selecting step, and the expression amount measuring step while the stage of the cell cycle is identified in the cells selected at the selecting step.

According to still another aspect of the present invention, a measuring apparatus includes an imaging optical system which forms a specimen image of a specimen which is labeled with a luminescent label emitting weak luminescence or a fluorescent label emitting fluorescence by excitation and held by a holding unit; and a capturing unit that captures the specimen image, wherein the imaging optical system includes a weak luminescence imaging optical system that forms the specimen image of weak luminescence from the luminescent label as a weak luminescent specimen image; and a fluorescence imaging optical system that forms the specimen image of fluorescence from the fluorescent label as a fluorescent specimen image, and the capturing unit captures the weak luminescent specimen image and the fluorescent specimen image.

According to still another aspect of the present invention, in the measuring apparatus, the fluorescence imaging optical system comprises an illuminating unit that illuminates the specimen.

According to still another aspect of the present invention, the measuring apparatus includes an image capture switch controlling unit that makes a control to switch between the capturing of the weak luminescent specimen image and the capturing of the fluorescent specimen image, based on an image characteristic of the weak luminescent specimen image captured by the capturing unit.

According to still another aspect of the present invention, in the measuring apparatus, the image characteristic is image intensity of the weak luminescent specimen image, and the image capture switch controlling unit switches from the capturing of the weak luminescent specimen image to the capturing of the fluorescent specimen image when the image intensity is higher than a predetermined threshold.

According to still another aspect of the present invention, in the measuring apparatus, the image intensity is the image intensity of all or part of the weak luminescent specimen image, and is cumulative image intensity from a predetermined time point up to a current time point or current image intensity.

According to still another aspect of the present invention, in the measuring apparatus, the fluorescence imaging optical system includes a fluorescence objective lens that converts fluorescence from each point of the fluorescent label into a substantially parallel pencil of rays, a fluorescence imaging lens that concentrates the fluorescence converted into the substantially parallel pencil of rays by the fluorescence objective lens to form the fluorescent specimen image, a fluorescence unit including: an excitation light transmitting filter which selectively transmits excitation light that excites the fluorescent label; a fluorescence transmitting filter which selectively transmits the fluorescence from the fluorescent label; and a dichroic mirror which reflects the excitation light and transmits the fluorescence, the fluorescence unit being arranged between the fluorescence objective lens and the fluorescence imaging lens, and an excitation light irradiating unit including an excitation light source that emits the excitation light, the excitation light irradiating unit reflecting the excitation light from the excitation light source by the dichroic mirror to irradiate the specimen with the excitation light.

According to still another aspect of the present invention, in the measuring apparatus, the weak luminescence imaging optical system includes a weak luminescence objective lens that converts weak luminescence from each point of the luminescent label into a substantially parallel pencil of rays, and a weak luminescence imaging lens that concentrates the weak luminescence converted into the substantially parallel pencil of rays by the weak luminescence objective lens to form the weak luminescent specimen image.

According to still another aspect of the present invention, in the measuring apparatus, the weak luminescence imaging optical system and the fluorescence imaging optical system are mutually arranged on the opposite sides across the specimen, the excitation light irradiating unit includes a non-irradiating unit that does not irradiate the specimen with excitation light, and the image capture switch controlling unit controls the non-irradiating unit not to irradiate the specimen with excitation light when causing the capturing unit to capture a weak luminescent specimen, and controls the excitation light irradiating unit to irradiate the specimen with excitation light when causing the capturing unit to capture a fluorescent specimen image.

According to still another aspect of the present invention, the measuring apparatus includes a visual field moving unit that moves the visual fields of the weak luminescence imaging optical system and the fluorescence imaging optical system relatively and parallel to each other.

According to still another aspect of the present invention, in the measuring apparatus, the holding unit includes a specimen transferring unit that transfers the specimen to each visual field of the weak luminescence imaging optical system and the fluorescence imaging optical system.

According to still another aspect of the present invention, in the measuring apparatus, the weak luminescence objective lens and the fluorescence objective lens are the same lens, and the weak luminescence imaging optical system and the fluorescence imaging optical system share the objective lens.

According to still another aspect of the present invention, the measuring apparatus further includes a mirror which is insertably and detachably arranged in a pupil space between the objective lens and the fluorescence unit, the mirror reflecting weak luminescence from the objective lens to the weak luminescence imaging lens when arranged in the pupil space, wherein the excitation light irradiating unit includes a non-irradiation unit that does not irradiate the specimen with excitation light, and the image capture switch controlling unit arranges the mirror in the pupil space and controls the non-irradiating unit not to irradiate with excitation light when causing the capturing unit to capture a weak luminescent specimen image, and arrange the mirror out of the pupil space and controls the excitation light irradiating unit to irradiate with excitation light when causing the capturing unit to capture a fluorescent specimen image.

According to still another aspect of the present invention, in the measuring apparatus, the weak luminescence imaging optical system and the fluorescence imaging optical system are arranged on the same side with respect to the specimen, the holding unit includes a specimen transferring unit that transfers the specimen to each visual field of the weak luminescence imaging optical system and the fluorescence imaging optical system, and the image capture switch controlling unit controls the specimen transferring unit to transfer the specimen to the visual field of the weak luminescence imaging optical system when causing the capturing unit to capture a weak luminescent specimen image, and controls the specimen transferring unit to transfer the specimen to the visual field of the fluorescence imaging optical system when causing the capturing unit to capture a fluorescent specimen image.

According to still another aspect of the present invention, the measuring apparatus further includes an optical system moving unit that moves the weak luminescence imaging optical system and the fluorescence imaging optical system so that the visual fields of the weak luminescence imaging optical system and the fluorescence imaging optical system cover the specimen, wherein the weak luminescence imaging optical system and the fluorescence imaging optical system are arranged on the same side with respect to the specimen, and the image capture switch controlling unit controls the optical system moving unit to move the weak luminescence imaging optical system so that the visual field of the weak luminescence imaging optical system covers the specimen when causing the capturing unit to capture a weak luminescent specimen image, and controls the optical system moving unit to move the fluorescence imaging optical system so that the visual field of the fluorescence imaging optical system covers the specimen when causing the capturing unit to capture a fluorescent specimen image.

According to still another aspect of the present invention, in the measuring apparatus, the optical system moving unit includes an axis of rotation that passes through the midpoint of a line segment connecting substantially central points of the visual fields of the weak luminescence imaging optical system and the fluorescence imaging optical system and is substantially parallel to the optical axis of each of the weak luminescence imaging optical system and the fluorescence imaging optical system, the optical system moving unit rotating and moving the weak luminescence imaging optical system and the fluorescence imaging optical system around the axis of rotation.

According to still another aspect of the present invention, in the measuring apparatus, the capturing unit includes a weak luminescence capturing unit that captures the weak luminescent specimen image, and a fluorescence capturing unit that captures the fluorescent specimen image.

According to still another aspect of the present invention, in the measuring apparatus, the capturing unit includes a weak luminescence capturing unit that captures the weak luminescent specimen image, and a fluorescence capturing unit that captures the fluorescent specimen image, and the optical system moving unit integrally moves the weak luminescence imaging optical system and the weak luminescence capturing unit as well as the fluorescence imaging optical system and the fluorescence capturing unit.

According to still another aspect of the present invention, in the measuring apparatus, the weak luminescent specimen image and the fluorescent specimen image are formed in substantially the same position by the weak luminescence imaging lens and the fluorescence imaging lens, respectively, and the capturing unit is fixed in a position substantially corresponding to the position where the weak luminescent specimen image and the fluorescent specimen image are formed.

According to still another aspect of the present invention, the measuring apparatus further includes an illuminating unit that corresponds to at least one of the weak luminescence imaging optical system and the fluorescence imaging optical system, for transmit illumination to the specimen.

According to still another aspect of the present invention, in the measuring apparatus, the transmitted illumination is at least one of illumination for bright field observation, illumination for dark field observation, illumination for differential interference observation, and illumination for phase contrast observation.

According to still another aspect of the present invention, in the measuring apparatus, the weak luminescence imaging optical system has a value calculated by $(NAo/\beta)^2$ of 0.01 or more, where NAo is a numerical aperture on the side of the specimen of the weak luminescence imaging optical system, and $\beta$ is a magnification for forming the weak luminescent specimen image.

EFFECT OF THE INVENTION (I) According to the present invention, a method or an apparatus obtains the amount of luminescence at a predetermined site by measuring the luminescence from a live sample into which a fusion gene is introduced, the fusion gene being obtained by fusing a targeting base sequence that directs a photoprotein to the predetermined site in the sample and a luminescence-related gene which expresses the photoprotein. The fusion gene is obtained by further fusing a fluorescence-related gene which expresses a fluorescence protein with the targeting base sequence, and the luminescence-related gene. The method or the apparatus includes the steps of capturing a fluorescent image of the sample into which the fusion gene is introduced, determining whether the photoprotein is localized at the predetermined site based on the captured fluorescent image, and measuring the luminescence from the sample when the localization is determined as the determined result. This allows for determining whether, when the luminescence from the predetermined site in the live sample is measured, the photoprotein is localized at the predetermined site in the sample itself.

According to another aspect of the present invention, the method or the apparatus includes, when live samples into which the fusion gene is introduced are present in an area to be captured, capturing a fluorescent image of the samples, determining whether the photoprotein is localized at the predetermined site in each sample based on the fluorescent image, capturing a luminescent image of the samples, selecting a sample for measurement from the samples in which the localization is determined by superimposing the captured fluorescent image and the captured luminescent image, and measuring the luminescence from the selected sample. This produces an effect that individual samples are distinguished from one another and the luminescence from the predetermined site can be measured in a single sample.

According to the present invention, the amount of luminescence from the predetermined site in the sample is obtained sequentially by repeatedly performing the capture of a fluorescent image, the determination of the localization, the capture of a luminescent image, the selection of the sample for measurement, and the measurement of the luminescence. This produces an effect that changes in luminescence at the predetermined site in a sample can be measured sequentially.

According to the present invention, fusion genes to be introduced into the samples are prepared in advance so that each combination of a targeted site to which the photoprotein is directed by the targeting base sequence, a luminescent color of luminescence emitted from the photoprotein, and a fluorescent color of fluorescence emitted from the fluorescence protein is different. The method or the apparatus includes separating luminescence from the sample in accordance with luminescent color, determining whether the photoprotein is localized at the predetermined site for each fluorescent color, specifying luminescence from the site where the localization is determined among the multiple luminescence separated when the localization is determined as the determined result, and measuring the specified luminescence. For example, this produces an effect in which the luminescence from multiple sites in one sample can be measured at the same time.

According to the present invention, the sample is any one of a tissue, a cell, and an individual, which allows for using various samples.

According to the present invention, the sample is a cell, the predetermined site is mitochondria, the targeting base sequence is a mitochondrial targeting signal, the photoprotein is luciferase, and the fluorescence protein is a green fluorescent protein. ATP at the predetermined site in the selected sample is quantified based on the measured amount of luminescence, and then the amount of ATP at the predetermined site in the samples is quantified sequentially by repeatedly performing the capture of a fluorescent image, the determination of the localization, the capture of a luminescent image, the selection of the sample for measurement, the measurement of the luminescence, and further quantification of ATP. This produces an effect that changes of the amount of ATP in mitochondria of a particular cell can be measured sequentially.

(II) According to the present invention, in living cells into which a luminescence-related gene which expresses a photoprotein, a fluorescence-related gene which expresses a fluorescence protein, and a gene to be analyzed are introduced, luminescence intensity of luminescence emitted from the cells is measured, fluorescence intensity emitted from the cells is measured, and the amount of expression of the gene to be analyzed is measured based on the measured luminescence intensity or the measured fluorescence intensity. The cell is a cell into which a cell cycle-related gene which is expressed at a predetermined stage of the cell cycle is introduced in addition to the luminescence-related gene, the fluorescence-related gene, and the gene to be analyzed. A stage of the cell cycle is identified by determining whether the cell cycle-related gene is expressed or not based on the measured fluorescence intensity when luminescence intensity is used to measure the amount of expression, and the measured luminescence intensity when fluorescence intensity is used to measure the amount of expression. This produces an effect that when the amount of expression of the gene to be analyzed introduced into cells is measured, stages of the cell cycle can be identified in the cell without performing the synchronized culture method, resulting in reducing the procedural burden on experimenters. Further, this produces an effect in which the relationship between the gene to be analyzed and the stage of the cell cycle can be evaluated for each cell. Specifically, this produces an effect in which as for the gene to be analyzed whose direct involvement in the cell cycle is unknown, it is possible to obtain change in expression which is caused by administration of a medicine or temperature changes, and the stage of the cell cycle, which allows for verifying the relation between the gene to be analyzed and the cell cycle. Further, this produces an effect in which as for the gene to be analyzed considered to be directly involved in the cell cycle, both the amount of expression of the gene to be analyzed and the stage of the cell cycle can be obtained, thereby enabling to evaluate whether the gene to be analyzed is useful as a cell-cycle marker.

According to the present invention, when multiple cells are present in an area to be captured, a fluorescent image of the cells is captured and a luminescent image of the cells is captured. Luminescence intensity of luminescence emitted from each cell is measured based on the captured luminescent image, and fluorescence intensity emitted from each cell is measured based on the captured fluorescent image, so that the amount of expression of gene to be analyzed in each cell is measured based on the measured luminescence intensity or the measured fluorescence intensity. The stage of the cell cycle is identified by determining whether the cell cycle-related gene is expressed in each cell based on the measured fluorescence intensity when luminescence intensity is used to measure the amount of expression, and on the measured luminescence intensity when fluorescence intensity is used to measure the amount of expression. This produces an effect that the amount of expression of the gene to be analyzed in each cell of the cells can be measured, and the stage of the cell cycle can be identified for each cell. Further, this produces an effect in which the relationship between the gene to be analyzed and the stage of the cell cycle can be evaluated for each cell.

According to the present invention, the cells for measurement are selected from among the cells whose stage is identified and the amount of expression of the gene to be analyzed introduced into the selected cells is measured based on the measured luminescence intensity or the measured fluorescence intensity. This produces an effect that individual cells are distinguished from one another to measure the amount of expression of the gene to be analyzed in a single cell, and the stage of the cell cycle can be identified.

According to the present invention, the amount of expression of the gene to be analyzed is measured sequentially by repeatedly performing the capture of a luminescent image, the capture of a fluorescent image, the measurement of luminescence intensity, the measurement of fluorescence intensity, the identification of the stage, the selection of cells, and the measurement of the amount of expression while the stage of the cell cycle is identified in the selected cells. This produces an effect that change in expression of the gene to be analyzed can be measured sequentially in a single cell while the stage of the cell cycle is identified.

According to the present invention, in measurement of the amount of expression, the amount of expression of the gene to be analyzed is measured in the selected cell based on the measured fluorescence intensity, and a site of the expression of the gene to be analyzed in the cell is identified based on the captured fluorescent image. This produces an effect which allows for not only the evaluation of the relationship between the gene to be analyzed and the stage of the cell cycle, but also the identification of a site of the expression of the gene to be analyzed in a cell.

Further, according to the present invention, in living cells into which a luminescence-related gene which expresses a photoprotein and a gene to be analyzed are introduced, luminescence intensity of luminescence emitted from the cells is measured, and the amount of expression of the gene to be analyzed is measured on the basis of the measured luminescence intensity. The cell is stained with a fluorescent substance at the predetermined site (specifically, nucleus, cell membrane, cytoplasm, etc.), a fluorescent image of the cell is captured, and the stage of the cell cycle is identified by determining whether the shape of a cell is changed or not based on the captured fluorescent image. This produces an effect that when the amount of expression of the gene to be analyzed introduced into cells is measured, the stage of the cell cycle can be identified in the cells without performing the synchronized culture method, resulting in reducing the procedural burden on experimenters. Further, this produces an effect in which the relationship between the gene to be analyzed and the stage of the cell cycle can be evaluated.

Specifically, this produces an effect in which as for the gene to be analyzed whose direct involvement in the cell cycle is unknown, change in expression which is caused by administration of a medicine or temperature changes can be obtained in addition to the stage of the cell cycle, which allows for verifying the relation between the gene to be analyzed and the cell cycle. Further, this produces an effect in which as for the gene to be analyzed considered to be directly involved in the cell cycle, both the amount of expression of the gene to be analyzed and the stage of the cell cycle can be obtained, thereby enabling to evaluate whether the gene to be analyzed is useful as a cell-cycle marker or not.

According to the present invention, when cells are present in an area to be captured, a luminescent image of the cells is captured, and a fluorescent image of the cells is captured. Luminescence intensity of luminescence emitted from each cell is measured based on the captured luminescent image, and the amount of expression of gene to be analyzed in each cell is measured based on the measured luminescence intensity. The stage of the cell cycle is identified by determining whether the shape of the cell is changed or not based on the captured fluorescent image. This produces an effect that the amount of expression of the gene to be analyzed in each of the cells is measured and the stage of the cell cycle can be identified for each cell. Further, this produces an effect in which the relationship between the gene to be analyzed and the stage of the cell cycle can be evaluated for each cell.

According to the present invention, the cells for measurement are selected from among the cells whose stages are identified, and the amount of expression of gene to be analyzed introduced into the selected cells is measured based on the measured luminescence intensity. This produces an effect that individual cells are distinguished from one another, the amount of expression of the gene to be analyzed is measured in a single cell, and the stage of the cell cycle can be identified.

According to the present invention, the amount of expression of gene to be analyzed is measured sequentially by repeatedly performing the capture of a luminescent image, the capture of a fluorescent image, the measurement of luminescence intensity, the identification of the stage, the selection of cells, and the measurement of the amount of expression while the stage of the cell cycle is identified in the selected cells. This produces an effect that change in expression of the gene to be analyzed can be measured sequentially in a single cell while the stage of the cell cycle is identified.

(III) In the measuring apparatus according to the present invention, the observation of weak luminescence and fluorescence can be individually performed for the same specimen held by the holding unit and the observation of weak luminescence can be switched to the observation of fluorescence immediately depending on the results of the observation of weak luminescence.

Figure 1:
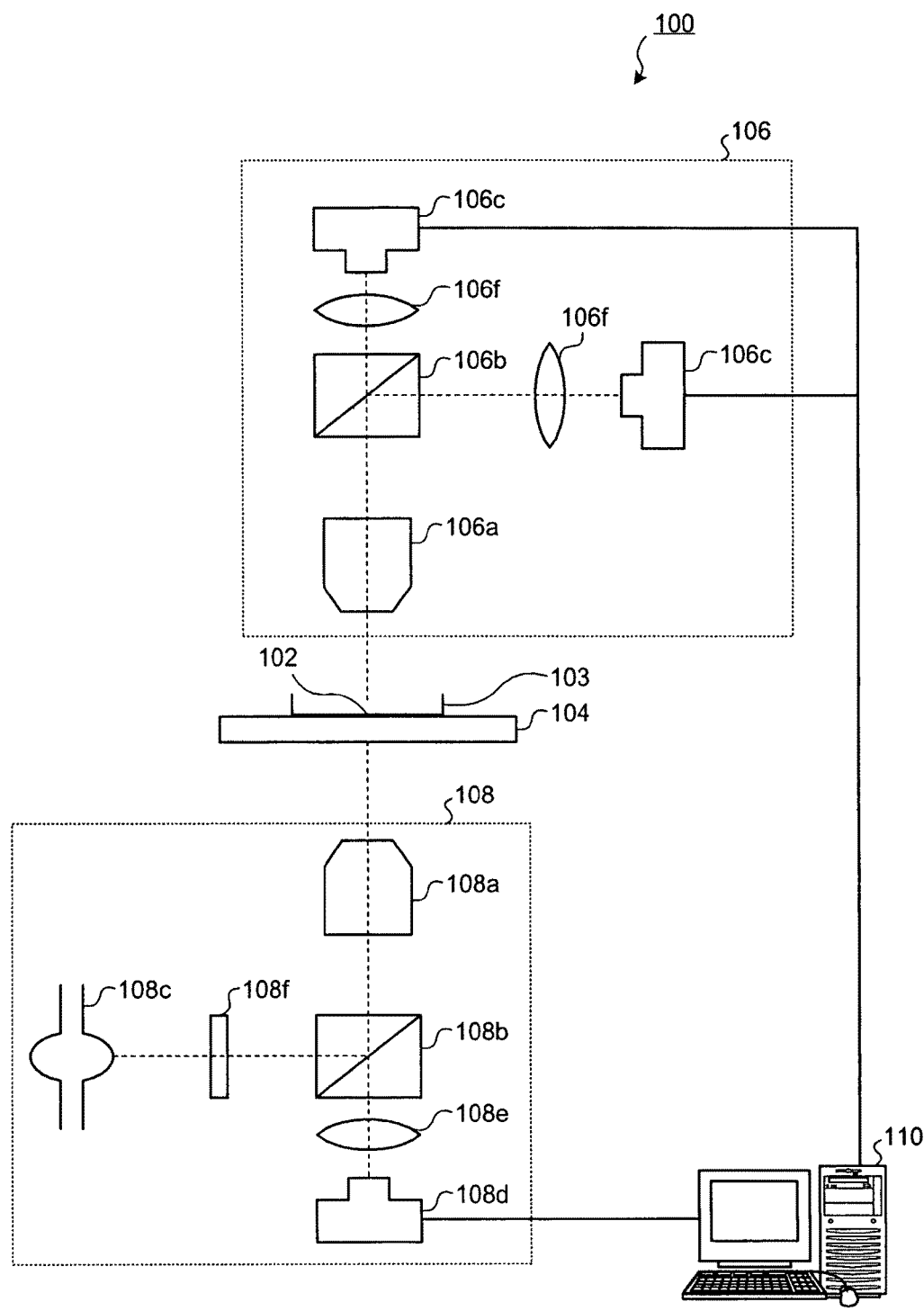
FIG. 1 is a diagram of an example of the entire configuration of a predetermined site luminescence measuring apparatus 100.

EXPLANATIONS OF LETTERS OR NUMERALS 100 predetermined site luminescence measuring apparatus
102 sample
103 container
104 stage
106 luminescent image capturing unit
   106a objective lens (for observation of luminescence)
   106b dichroic mirror
   106c CCD camera
   106d split image unit
   106e filter wheel
   106f imaging lens
108 fluorescent image capturing unit
   108a objective lens (for observation of fluorescence)
   108b dichroic mirror
   108c light source
   108d CCD camera
   108e imaging lens
   108f shutter
   108g spectral filter for excitation
   108h optical fiber
   108i condenser lens
   108j filter for luminescence and fluorescence spectra
110 information communication terminal
112 controlling unit
   112a fluorescent image capture instructing unit
   112b fluorescent image acquiring unit
   112c determining unit
   112d luminescent image capture instructing unit
   112e luminescent image acquiring unit
   112f selecting unit
   112g luminescence measuring unit
   112h related substance quantifying unit
114 clock generating unit 116 storage unit
118 communication interface unit
120 input/output interface unit
122 input unit
124 output unit
1000 expression amount measuring apparatus
1020 cell
1030 container
1040 stage
1060 luminescent image capturing unit
1060a objective lens (for observation of luminescence)
1060b dichroic mirror
1060c CCD camera
1060d split image unit
1060e filter wheel
1080 fluorescent image capturing unit
1080a objective lens (for observation of fluorescence)
1080b dichroic mirror
1080c xenon lamp
1080d CCD camera
1100 information communication terminal
1120 controlling unit
   1120a fluorescent image capture instructing unit
   1120b luminescent image capture instructing unit
   1120c fluorescent image acquiring unit
   1120d luminescent image acquiring unit
   1120e determining unit
   1120f fluorescence measuring unit
   1120g luminescence measuring unit
   1120h stage identifying unit
   1120i selecting unit
   1120j expression measuring unit
1140 clock generating unit
1160 storage unit
1180 communication interface unit
1200 input/output interface unit
1220 input unit
1, 11 objective lens
2, 12, 32 imaging lens
3, 13 imaging device
4 excitation light source
5 lens
6 fluorescence cube
6a excitation filter
6b absorption filter
6c dichroic mirror
7, 17 holding unit
7a holding member
7b, 17b movable stage
8, 18 stage driving unit
9 monitor
14 rotary drive unit
15a, 15b fixed shaft
21, 22, 23, 24, 25, 26 casing
33, 43 shutter
34 mirror
35 optical path switch driving unit
44 white light source
45 illuminating lens system
45a collector lens
45b condenser lens
46 illumination driving unit
100a, 200, 300, 400, 500, 600, 700, 800, 900 microscope apparatus
101, 201 fluorescence microscope unit
102a, 202 weak luminescence microscope unit
103a transmitted illumination unit
104a, 105 fluorescent lighting unit
PC1~PC9 controlling apparatus
S specimen

BEST MODES FOR CARRYING OUT THE INVENTION (I) Hereinbelow, embodiments of a predetermined site luminescence measuring method and a predetermined site luminescence measuring apparatus in the present invention will be described in detail on the basis of the drawings. However, the present invention is not limited by these embodiments.

First, the configuration of a predetermined site luminescence measuring apparatus 100 that realizes the present invention will be described with reference to FIGS. 1 to 3. FIG. 1 is a diagram of an example of the entire configuration of the predetermined site luminescence measuring apparatus 100.

Figure 14:
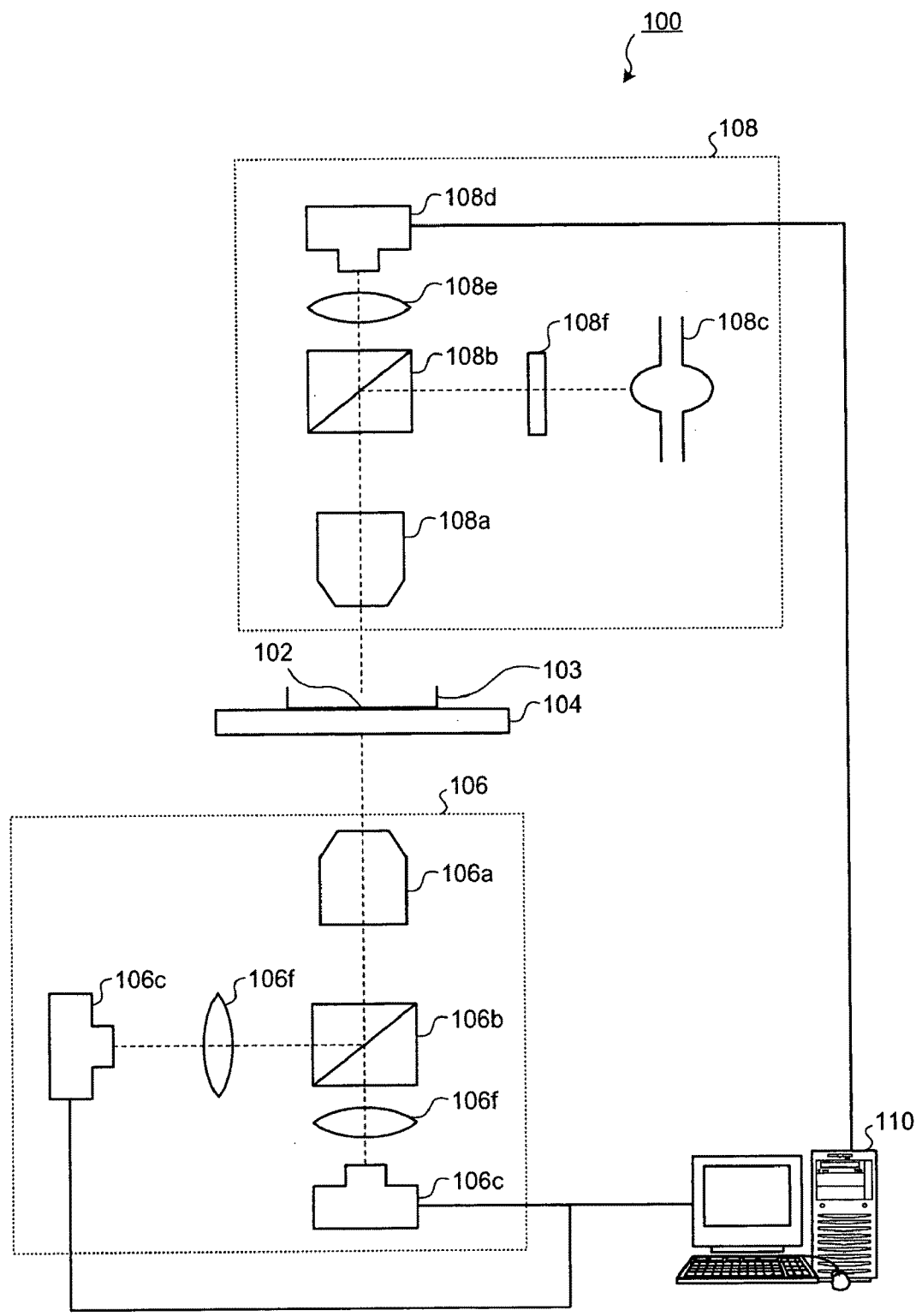
FIG. 14 is a diagram of an example of the entire configuration of the predetermined site luminescence measuring apparatus 100.

As shown in FIG. 1, the predetermined site luminescence measuring apparatus 100 includes a sample 102, a container 103 accommodating the sample 102 (specifically, a petri dish, a slide glass, a microplate, a gel supporting matrix, particulate carriers, etc.), a stage 104 on which the container 103 is arranged, a luminescent image capturing unit 106, a fluorescent image capturing unit 108, and an information communication terminal 110. In the predetermined site luminescence measuring apparatus 100, as shown in the figure, an objective lens 106a included in the luminescent image capturing unit 106 and an objective lens 108a included in the fluorescent image capturing unit 108 are arranged in vertically opposed positions across the sample 102, the container 103, and the stage 104. As shown in FIG. 14, the arrangement of the luminescent image capturing unit 106 and the fluorescent image capturing unit 108 may be replaced. Disturbance light from upper side of the sample which is caused by opening and closing a cover can be completely blocked by placing the luminescent image capturing unit 106 for measuring luminescence that is weaker than fluorescence on the downside, and an S/N ratio of a luminescent image can be increased. The fluorescent image capturing unit 108 that is a separate body from the luminescent image capturing unit 106 may be a laser scanning optical system.

Referring to FIG. 1 again, the sample 102 is a sample into which a fusion gene is introduced. The fusion gene is obtained by fusing a targeting base sequence that directs a photoprotein to a predetermined site (for example, mitochondria or cytoplasm, nucleus) in the sample 102, a luminescence-related gene that expresses the photoprotein, and a fluorescence-related gene that expresses a fluorescence protein. The sample 102 is a living sample such as a test sample, a tissue, a cell, and an individual. Specifically, the sample 102 may be a sample into which a plasmid vector containing the fusion gene is introduced.

The luminescent image capturing unit 106 is specifically an upright luminescence microscope and captures a luminescent image of the sample 102. As shown in the figure, the luminescent image capturing unit 106 includes an objective lens 106a, a dichroic mirror 106b, a CCD camera 106c, and an imaging lens 106f. Specifically, the objective lens 106a has a value not less than 0.01 found by (Numerical Aperture/magnification)$^2$. The dichroic mirror 106b is used to separate the luminescence emitted from the sample 102 according to color and measures the amount of the luminescence according to color using two-color luminescence. The CCD camera 106c captures the luminescent image and bright-field image of the sample 102 that are projected on the chip surface of the CCD camera 106c through the objective lens 106a, the dichroic mirror 106b, and the imaging lens 106f. The CCD camera 106c is connected to the information communication terminal 110 to enable either wired or wireless communication. Here, when samples 102 are present in an area to be captured, the CCD camera 106c may capture the luminescent image and bright-field image of the samples 102 that are in the area to be captured. The imaging lens 106f forms an image (specifically, the image of the sample 102) that is impinged on the imaging lens 106f through the objective lens 106a and the dichroic mirror 106b. FIG. 1 depicts one example where luminescent images corresponding to two luminescence separated by the dichroic mirror 106b are separately captured by the two CCD cameras 106c. When one luminescence is used, the luminescent image capturing unit 106 may include the objective lens 106a, one CCD camera 106c, and the imaging lens 106f.

Figure 2:
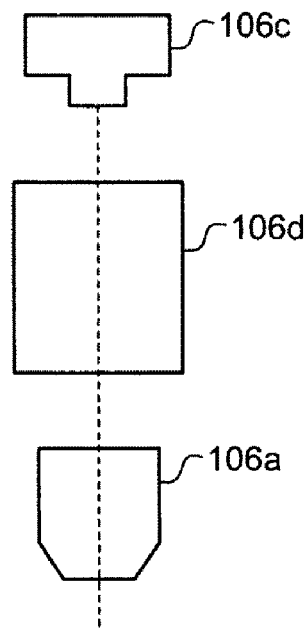
FIG. 2 is a diagram of an example of the configuration of a luminescent image capturing unit 106 of the predetermined site luminescence measuring apparatus 100.

Here, when the amount of the luminescence is measured according to color using two-color luminescence, the luminescent image capturing unit 106 may include, as shown in FIG. 2, the objective lens 106a, the CCD camera 106c, a split image unit 106d, and the imaging lens 106f. The CCD camera 106c may capture a luminescent image (split image) and a bright-field image of the sample 102 that are projected on the chip surface of the CCD camera 106c through the split image unit 106d and the imaging lens 106f. As with the dichroic mirror 106b, the split image unit 106d is used to separate the luminescence emitted from the sample 102 according to color and used when the amount of the luminescence according to color using two-color luminescence is measured.

Figure 3:
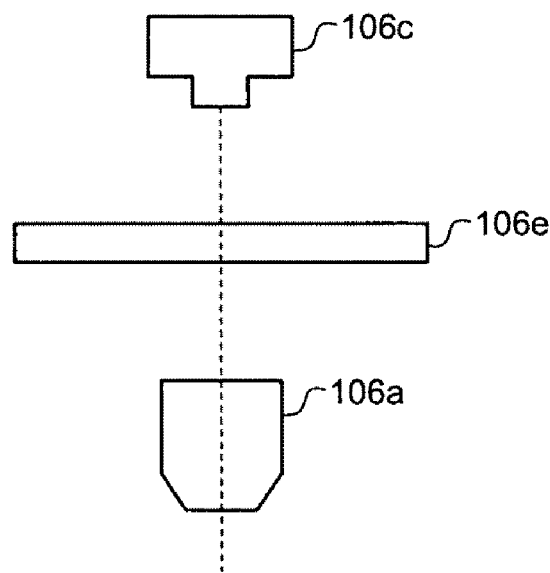
FIG. 3 is a diagram of another example of the configuration of the luminescent image capturing unit 106 of the predetermined site luminescence measuring apparatus 100.

Further, when the amount of the luminescence is measured according to color using plural-color luminescence (namely, when multicolored luminescence is used), the luminescent image capturing unit 106 may include, as shown in FIG. 3, the objective lens 106a, the CCD camera 106c, a filter wheel 106e, and the imaging lens 106f. The CCD camera 106c may capture a luminescent image and a bright-field image of the sample 102 that are projected on the chip surface of the CCD camera 106c through the split image unit 106d and the imaging lens 106f. The filter wheel 106e is used to replace the filter to separate the luminescence emitted from the sample 102 according to color and used when the amount of the luminescence according to color using plural-color luminescence is measured.

Referring to FIG. 1 again, the fluorescent image capturing unit 108 is specifically an inverted fluorescence microscope and captures a fluorescent image of the sample 102. As shown in the drawing, the fluorescent image capturing unit 108 includes an objective lens 108a, a dichroic mirror 108b, a light source 108c, a CCD camera 108d, an imaging lens 108e, and a shutter 108f. Specifically, objective lens 108a has a value not less than 0.01 found by (Numerical Aperture/magnification)$^2$. The dichroic mirror 108b transmits the fluorescence from the sample 102 and changes the direction of excitation light so as to irradiate the sample 102 with the excitation light emitted from the light source 108c. The light source 108c is provided to emit excitation light, and examples thereof include lamps such as xenon lamps and halogen lamps, laser, LED, and the like. The CCD camera 108d captures the fluorescent image and bright-field image of the sample 102 that are projected on the chip surface of the CCD camera 108d through the objective lens 108a, the dichroic mirror 108b, and the imaging lens 108e. Further, the CCD camera 108d is connected to the information communication terminal 110 to enable either wired or wireless communication. Here, when samples 102 are present in an area to be captured, the CCD camera 108d may capture the fluorescent image and bright-field image of samples 102 that are in the area to be captured. The imaging lens 108e forms an image (specifically, the image of the sample 102) that is impinged on the imaging lens 108e through the objective lens 108a and the dichroic mirror 108b. The shutter 108f switches the excitation light emitted from the light source 108c. In other words, the shutter 108f switches irradiating the sample 102 with the excitation light by transmitting or intercepting the excitation light emitted from the light source 108c.

Here, the luminescent image capturing unit 106 and the fluorescent image capturing unit 108 may be specifically an inverted luminescence microscope and an inverted fluorescence microscope, respectively. The stage 104 may be a rotation stage.

Figure 15:
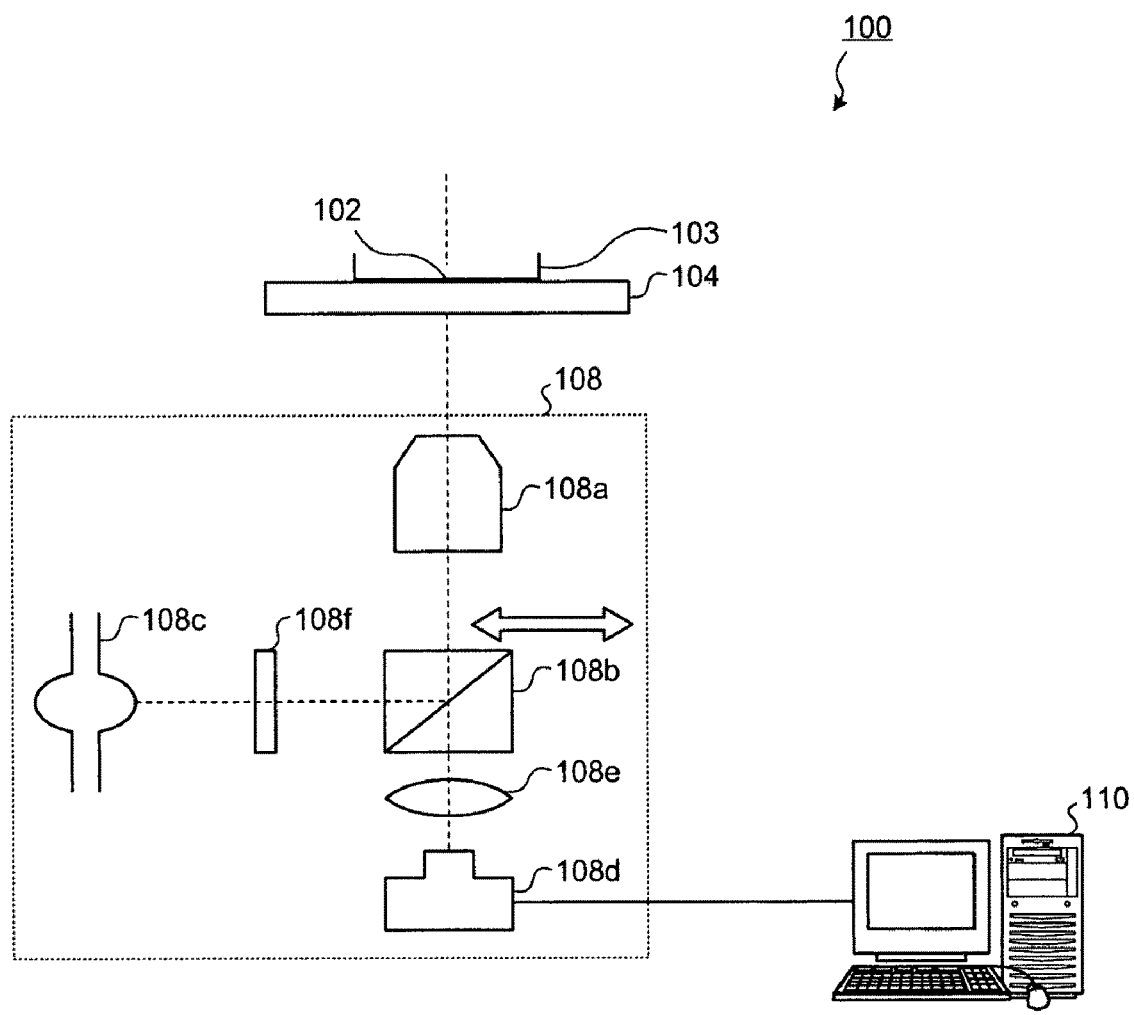
FIG. 15 is a diagram of an example of the entire configuration of the predetermined site luminescence measuring apparatus 100.

The predetermined site luminescence measuring apparatus 100 as shown in FIGS. 1 and 14 is configured such that the luminescent image capturing unit 106 and the fluorescent image capturing unit 108 are provided separately. However, the predetermined site luminescence measuring apparatus 100 may be configured such that the fluorescent image capturing unit 108 only is provided as shown in FIG. 15. In other words, the predetermined site luminescence measuring apparatus 100 may be configured so as to perform both fluorescent observation and luminescent observation by the fluorescent image capturing unit 108 only. When the fluorescence and luminescence observation are performed by using the predetermined site luminescence measuring apparatus 100 that is shown in FIG. 15, the predetermined site luminescence measuring apparatus 100 is preferably configured such that switching of the shutter 108f is performed automatically or manually in capturing a luminescent image (in performing luminescence detection) and the dichroic mirror 108b can be moved to the position off an optical path (shown by the dotted line in FIG. 15) automatically or manually. This allows for reduction of noise in the luminescent image. In the predetermined site luminescence measuring apparatus 100 shown in FIG. 15, the objective lens 108a preferably satisfies the condition "the value found by (Numerical Aperture/magnification)$^2$ is 0.01 or more".

Further, the predetermined site luminescence measuring apparatus 100 shown in FIG. 16, may be configured to irradiate the sample 102 with excitation light from above and perform the observation of fluorescence and luminescence from below the sample 102. Here, among the configuration of the predetermined site luminescence measuring apparatus 100 shown in FIG. 16, only the configuration which has not been described so far will be described. A spectral filter for excitation 108g separates the excitation light emitted from the light source 108c into multiple excitation light with different wavelength regions. An optical fiber 108h conducts each of the excitation light separated by the spectral filter for excitation 108g to the sample 102. A condenser lens 108i is used to uniformly illuminate the sample 102 and collects each of the excitation light conducted by the optical fiber 108h. A filter for luminescence and fluorescence spectra 108j separates the fluorescence and luminescence emitted from the sample 102 depending on the differences in the intensity or the wavelengths. In the predetermined site luminescence measuring apparatus 100 shown in FIG. 16, the objective lens 108a preferably satisfies the condition "the value found by (Numerical Aperture/magnification)$^2$ is 0.01 or more".

Figure 4:
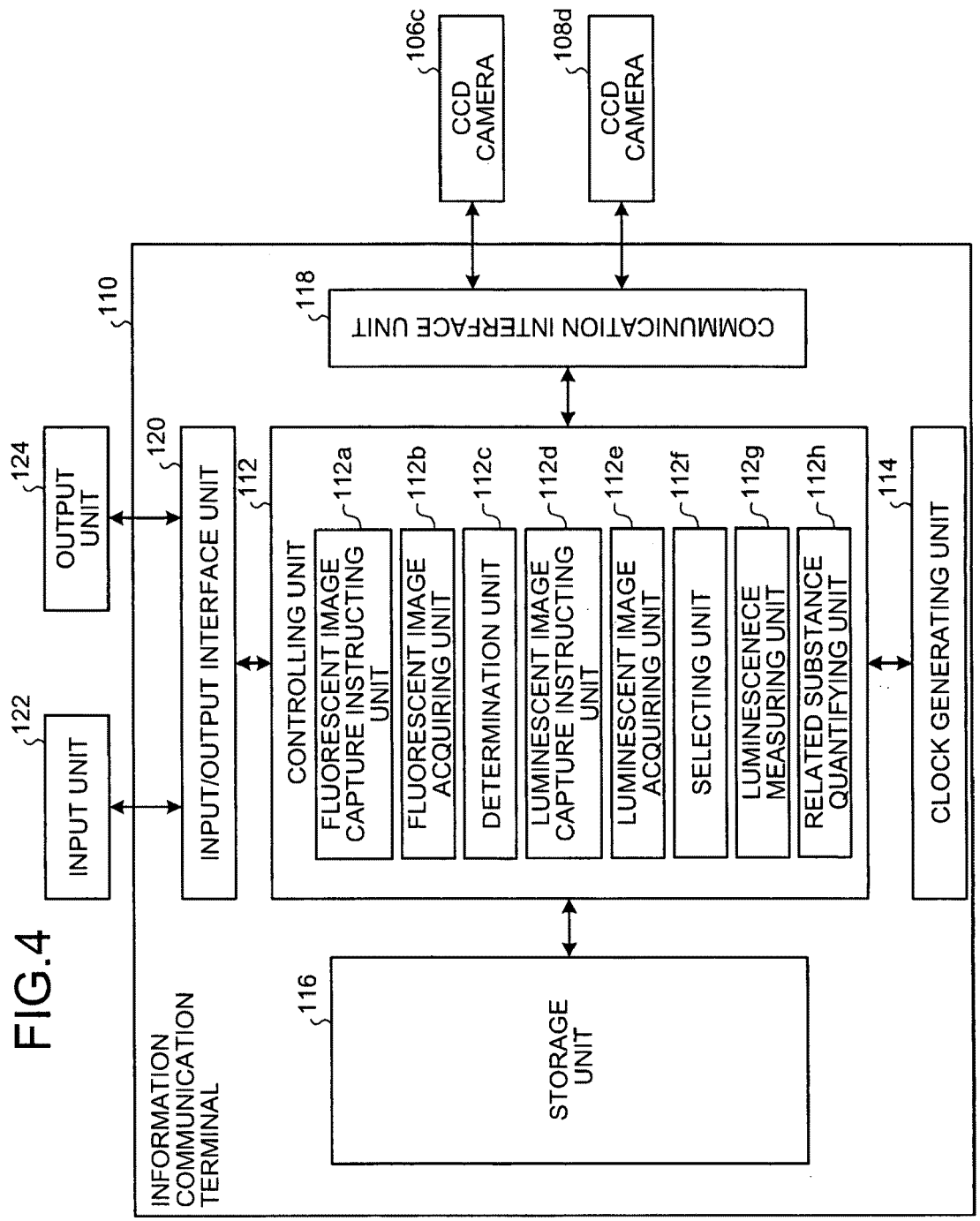
FIG. 4 is a block diagram of an example of the configuration of an information communication terminal 110 of the predetermined site luminescence measuring apparatus 100.

Referring to FIG. 1 again, information communication terminal 110 is specifically a personal computer. As shown in FIG. 4, the information communication terminal 110 includes, when classified roughly, a controlling unit 112, a clock generating unit 114 that generates a clock for the system, a storage unit 116, a communication interface unit 118, an input/output interface unit 120, an input unit 122, and an output unit 124. These respective units are connected through a bus.

The storage unit 116 is storage means, and usable examples thereof include memory devices such as RAM and ROM; fixed disk devices such as hard disks; flexible disks; optical disks; and the like. The storage unit 116 stores data obtained by processing of each unit in the controlling unit 112.

The communication interface unit 118 mediates communications in the information communication terminal 110, the CCD camera 106c, and the CCD camera 108d. That is, the communication interface unit 118 has a function of communicating data with other terminals via wired or wireless communication lines.

The input/output interface unit 120 is connected to the input unit 122 or the output unit 124. Here, in addition to a monitor (including household-use televisions), a speaker or a printer can be used as the output unit 124 (hereinafter, the output unit 124 is sometimes described as a monitor). Further, a monitor which cooperates with a mouse to realize a pointing device function can be used as the input unit 122 in addition to a microphone, a keyboard, and a mouse.

The controlling unit 112 has an internal memory to store a control program such as OS (Operating System), a program in which various kinds of procedures are defined, and required data, and performs various processing based on these programs. The controlling unit 112 includes, when classified roughly, a fluorescent image capture instructing unit 112a, a fluorescent image acquiring unit 112b, a the determining unit 112c, a luminescent image capture instructing unit 112d, a luminescent image acquiring unit 112e, a selecting unit 112f, a luminescence measuring unit 112g, and a related substance quantifying unit 112h.

The fluorescent image capture instructing unit 112a instructs the CCD camera 108d to capture a fluorescent image and a bright-field image through the communication interface unit 118. The fluorescent image acquiring unit 112b obtains a fluorescent image and a bright-field image captured by the CCD camera 108d through the communication interface unit 118.

The determining unit 112c determines whether a fusion gene is introduced into the sample 102 and also determines whether the photoprotein is localized at the predetermined site based on the fluorescent image and bright-field image obtained by the fluorescent image acquiring unit 112b. Here, when samples 102 are found in the fluorescent image and bright-field image obtained by the fluorescent image acquiring unit 112b, the determining unit 112c, based on the fluorescent image and bright-field image, determines whether a fusion gene is introduced into the sample 102 for each sample 102 and also determines whether the photoprotein is localized at the predetermined site for each sample 102.

The luminescent image capture instructing unit 112d instructs the CCD camera 106c to capture a luminescent image and a bright-field image through the communication interface unit 118. The luminescent image acquiring unit 112e obtains the luminescent image and bright-field image captured by the CCD camera 106c through the communication interface unit 118.

The selecting unit 112f superimposes the fluorescent image and bright-field image obtained by the fluorescent image acquiring unit 112b as well as the luminescent image and bright-field image obtained by the luminescent image acquiring unit 112e and then selects the sample 102 for measurement from the samples 102 whose results show the localization determined by the determining unit 112c.

The luminescence measuring unit 112g measures the luminescence from the samples 102 whose results show the localization determined by the determining unit 112c or the sample 102 selected by the selecting unit 112f based on the luminescent image. The related substance quantifying unit 112h quantifies the amount of a substance related directly or indirectly to changes in the amount of luminescence based on the amount of luminescence measured by the luminescence measuring unit 112g. For example, when the photoprotein is luciferase, the related substance quantifying unit 112h quantifies the amount of ATP, the substance related directly or indirectly to changes in the luminescence amount of the luciferase. Namely, the related substance quantifying unit 112h can be used as ATP quantifying means that quantifies ATP based on the amount of luminescence measured by the luminescence measuring unit 112g.

Figure 5:
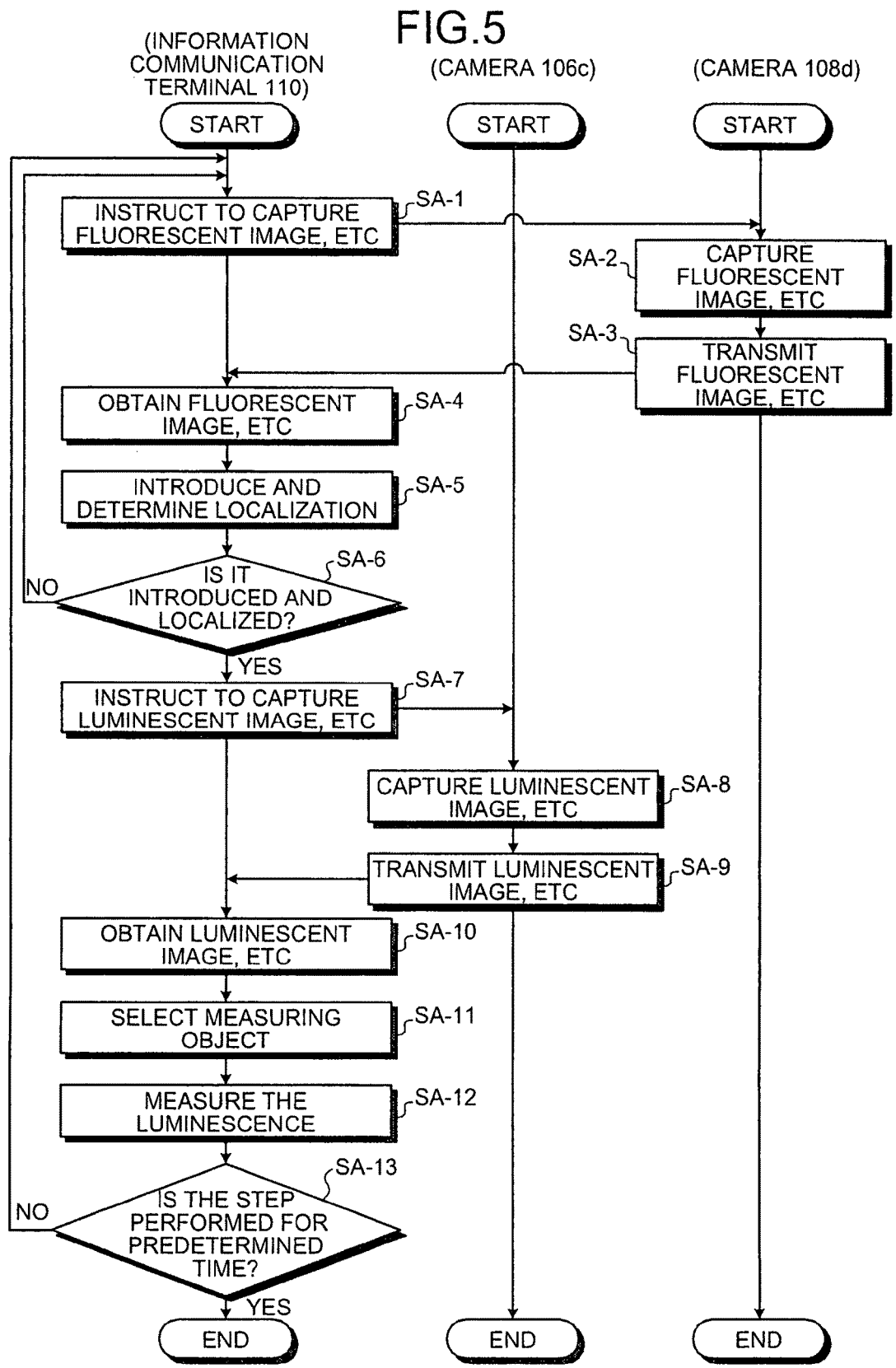
FIG. 5 is a flow chart of an example of a processing that is performed by the predetermined site luminescence measuring apparatus 100.

In the above configuration, one example of the processing performed by the predetermined site luminescence measuring apparatus 100 will be described with reference to FIG. 5. Hereinafter, description will be given to one example of the processing when the same fusion gene is introduced into samples 102 and then the luminescence in the predetermined site in a particular sample among the samples 102 is measured sequentially.

First, the information communication terminal 110 instructs the CCD camera 108d to capture a fluorescent image and a bright-field image through the communication interface unit 118 in the processing of the fluorescent image capturing instruction unit 112a (step SA-1). Next, the CCD camera 108d captures the fluorescent image and bright-field image of the samples 102 that are in the area to be captured (step SA-2: see FIG. 6); and transmitting them to the information communication terminal 110 (step SA-3). In this regard, the sample 102 is irradiated with excitation light only when capturing a fluorescent image. Next, the information communication terminal 110 obtains the fluorescent image and bright-field image captured by the CCD camera 108d through the communication interface unit 118 in processing of the fluorescent image acquiring unit 112b, and stores them in a predetermined storage area of the storage unit 116 (step SA-4).

Figure 6:
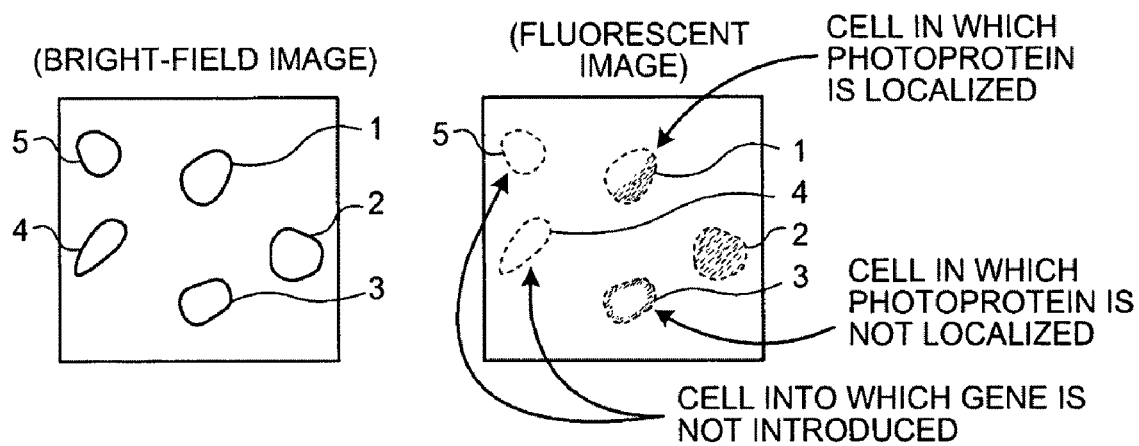
FIG. 6 is a view of an example of a bright-field image and a fluorescent image captured by a fluorescent image capturing unit 108.

Next, the information communication terminal 110 determines whether a fusion gene is introduced into each sample 102 by comparing the fluorescent image with the bright-field image in processing of the determining unit 112c, and determines whether the photoprotein is localized at the predetermined site for each sample 102 in the sample 102 into which the fusion gene is determined to be introduced (step SA-5). This makes it possible to identify, as shown in FIG. 6, a cell (cell 1) in which the gene is introduced and the photoprotein is localized at the predetermined site from among, for example, the samples 102 (cells 1 to 5).

Figure 7:
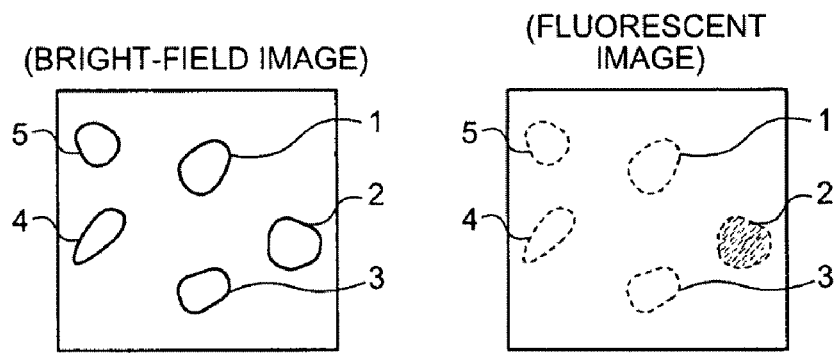
FIG. 7 is a view of an example of a bright-field image and a luminescent image captured by a luminescent image capturing unit 106.

Next, when the sample 102 in which the gene is introduced and the photoprotein is localized at the predetermined site is present (step SA-6: Yes), the information communication terminal 110 instructs the CCD camera 106c to capture a luminescent image and a bright-field image through the communication interface unit 118 in the processing of the luminescent image capture instructing unit 112d (step SA-7). Next, the CCD camera 106c captures the luminescent image and bright-field image of samples 102 that are in the area to be captured (step SA-8: see FIG. 7), and transmits them to the information communication terminal 110 (step SA-9). The luminescent image shown in FIG. 7 indicates one example when luminescence of the cell 2 is the strongest.

Next, the information communication terminal 110 obtains the luminescent image and bright-field image captured by the CCD camera 106c through the communication interface unit 118 in processing of the luminescent image acquiring unit 112e, and in processing of the controlling unit 112, obtains a time clock (corresponding to T1 in FIG. 8 which will be described later) from the clock generating unit 114, and stores the luminescent image, the bright field, and the time clock in a predetermined storage area of the storage unit 116 correspondingly to the fluorescent image and bright-field image which have already been stored, (step SA-10).

Figure 8:
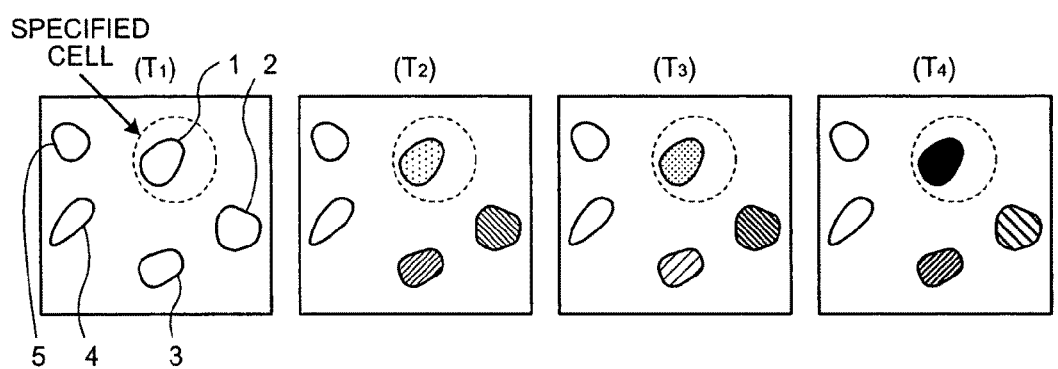
FIG. 8 is a view of an example of overlapped images captured by the luminescent image capturing unit 106 and the fluorescent image capturing unit 108 in chronological order.

Next, the information communication terminal 110 superimposes the bright-field image, fluorescent image, and luminescent image, and selects (identifies) a sample for measurement from the samples where the localization determined by the determining unit 112c in processing of the selecting unit 112f (step SA-11). In the example shown in FIG. 6, the cell into which the gene is introduced and a photoprotein is localized at the predetermined site is the cell 1 only. Therefore, the cell 1 is automatically identified in step SA-11 as shown in FIG. 8.

Next, the information communication terminal 110 measures, in processing of the luminescence measuring unit 112g, the luminescence corresponding to the selected sample 102 (luminescence intensity) based on a luminescent image, stores the identification information that identifies the selected sample 102 (for example, the cell 1 in FIG. 8) and the amount of luminescence correspondingly to the fluorescent image, luminescent image, bright-field image, and time clock which have already been stored, in a predetermined storage area of the storage unit 116 (step SA-12).

Figure 9:
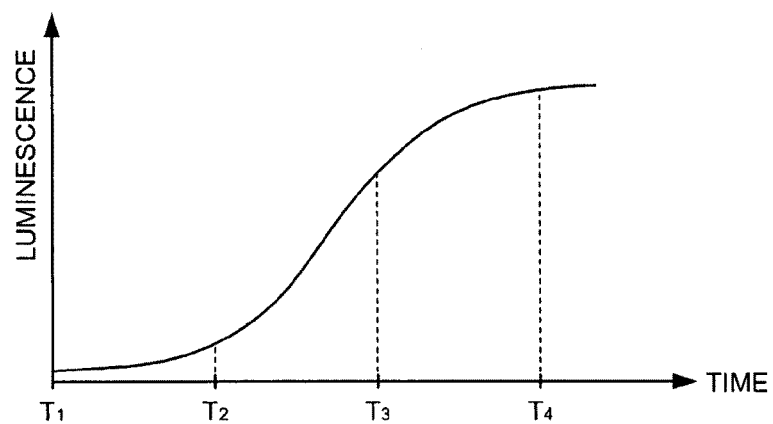
FIG. 9 is a graph of an example of changes over time in luminescence intensity of a specified cell.

As shown in FIG. 9, the information communication terminal 110 sequentially (for example, per time clocks $T_1$ to $T_4$ shown in FIGS. 8 and 9) obtains changes of the luminescence amount in the predetermined site of the selected sample 102 (for example, the cell 1 shown in FIGS. 6, 7, and 8) by repeatedly performing the above-mentioned steps SA-1 to SA-12, for example, at the time interval that is set up in advance predetermined times in processing of the controlling unit 112 (SA-13).

As described in detail above, according to the predetermined site luminescence measuring apparatus 100, a fusion gene to be introduced into the sample 102 is obtained by fusing the targeting base sequence, the luminescence-related gene, and a fluorescence-related gene which expresses a fluorescence protein. A fluorescent image of the sample 102 into which the fusion gene is introduced is captured, it is determined whether a photoprotein is localized at the predetermined site or not based on the captured fluorescent image, and the luminescence from the sample 102 is measured when the localization is determined as the determined result. This allows for determining whether, when the luminescence from the predetermined site in live samples 102 is measured, the photoprotein is localized at the predetermined site in the samples 102 themselves. Localization of a photoprotein in live samples into which a fusion gene is introduced is determined and the luminescence from the sample is measured, so that the amount of luminescence from the sample corresponds to the amount of luminescence from the predetermined site clearly. Therefore, it is possible to ensure reliability in which the measured luminescence amount is obtained from the predetermined site. For example, when the sample 102 is a cell, exact statistical analysis can be carried out without counting the cell into which no luminescence component is incorporated. Further, the predetermined site luminescence measuring apparatus 100 can be preferably used in, for example, examinations of various types of reactions (for example, drug stimulation, light exposure, etc.) or treatments.

According to the predetermined site luminescence measuring apparatus 100, when multiple live samples 102 into which the fusion gene is introduced are present in the area to be captured, a fluorescent image of the samples 102 is captured, it is determined whether or not a photoprotein is localized at the predetermined site for each sample 102 based on the fluorescent image, and a luminescent image of the samples 102 is captured. The sample 102 for measurement is selected from the samples 102 whose results show the localization determined by superimposing the captured fluorescent image and the captured luminescent image. Then, the luminescence from the selected sample 102 is measured. Thus, individual samples 102 are distinguished from one another, and the luminescence at the predetermined site can be measured in a single sample 102. Alternatively, it is possible to determine the localization of a photoprotein in the sample 102 themselves for analysis and the luminescence intensity emitted from the sample 102 by obtaining the fluorescence and luminescence as images. Thus, analysis can be performed without the influence of different physiological states of individual cells due to the efficiency of gene transduction or the cell cycle. Here, in the predetermined site luminescence measuring apparatus 100 according to the embodiment as shown in FIG. 5, for example, determines whether or not the photoprotein is localized at the predetermined site after capturing a fluorescent image, and captures a luminescent image when the localization is determined. However, the capture of a luminescent image may be performed together with the capture of a fluorescent image. In other words, the predetermined site luminescence measuring apparatus 100 may determine the localization after capturing the fluorescent image and luminescent image. Specifically, the predetermined site luminescence measuring apparatus 100 may, when multiple live samples 102 into which the fusion gene is introduced are present in the area to be captured, capture the fluorescent image and luminescent image of the samples 102, determines whether or not the photoprotein is localized at the predetermined site for each sample 102 based on the fluorescent image, selects the sample 102 for measurement from the samples 102 where the localization is determined by superimposing the captured fluorescent image and the captured luminescent image, and measures the luminescence from the selected sample 102.

Further, according to the predetermined site luminescence measuring apparatus 100, the amount of luminescence from the predetermined site in samples 102 is obtained sequentially by repeatedly performing the capture of a fluorescent image, the determination of the localization, the capture of a luminescent image, the selection of the sample 102 for measurement, and the measurement of the luminescence. Thus, it is possible to measure sequentially changes of the amount of luminescence from the predetermined site, for example, in particular samples 102.

Here, in the predetermined site luminescence measuring apparatus 100, multiple fusion genes to be introduced into the sample are present. The genes may be produced in advance so that each combination of a targeted site to which a photoprotein is directed by the targeting base sequence, a luminescent color of luminescence emitted from the photoprotein, and a fluorescent color of fluorescence emitted from the fluorescence protein is different. In this case, the predetermined site luminescence measuring apparatus 100 may separate the luminescence from the sample 102 in accordance with luminescent color, determine whether or not a photoprotein is localized at the predetermined site for each fluorescent color, specify the luminescence from the site where the localization of photoprotein is determined among multiple luminescence separated when the localization is determined as a result, and measure the specified luminescence. This makes it possible, for example, to measure the luminescence from multiple sites in one sample 102 at the same time, or to measure the luminescence from multiple sites in the sample 102 for each sample 102 at the same time.

Specifically, when the sample 102 is a cell, two fusion genes to be introduced into cell may be prepared. One of the fusion genes may be prepared in the combination of a targeted site to which green luciferase is directed by a mitochondrial targeting signal, a luminescent color (green) of luminescence emitted from the green luciferase, and a fluorescent color (green) of fluorescence emitted from GFP, and the other one may be produced in the combination of a luminescent color (red) of luminescence emitted from red luciferase which is expressed in cytoplasm, and a fluorescent color (cyanogen) of fluorescence emitted from CFP. In this case, the predetermined site luminescence measuring apparatus 100 may separate the luminescence from the cell in accordance with luminescent color (green, red); determine whether or not green luciferase is localized in mitochondria by the fluorescent color (green) emitted from GFP based on the captured fluorescent image as well as determine whether red luciferase is localized in cytoplasm by the fluorescent color (cyanogen) emitted from CFP; specify the luminescence from the site where the localization is determined among two luminescence (green, red) separated when the localization is determined as a result; and measure the specified luminescence. In other words, a mitochondrial targeting signal as a targeting base sequence, green luciferase as a photoprotein, and GFP as a fluorescence protein may be selected for an intracellular mitochondria. On the other hand, for cytoplasm in the cells, a targeting base sequence is not used and red luciferase as photoprotein and CFP as a fluorescence protein may be selected, and changes of the amount of luminescence in mitochondria and cytoplasm (further, the amount of ATP etc.) may measured individually and at the same time as changes of luminescence intensity.

Further, as for the predetermined site luminescence measuring apparatus 100, the amount of the substance related directly or indirectly to the increased or lessened luminescence may be quantified based on the measured luminescence amount. Specifically, when the photoprotein is luciferase, for example, the amount of ATP that is a substance related directly or indirectly to the increased or lessened luciferase may be quantified. This makes it possible to, for example, measure sequentially changes of the amount of a related substance (for example, ATP etc.) at the predetermined site in particular samples 102.

As another embodiment, for example, a method may include producing cells containing the fluorescence protein and photoprotein in which the expression amount and/or the localization site is changed for each cell cycle stage, and sequentially measuring the fluorescence and luminescence which are emitted from the cells, thereby to confirm the cell cycle by changes of the expression amount of a fluorescence protein and/or changes of localization site, and sequentially measure changes of the amount of luminescence of cells.

When multiple nerve cells are used, a fusion gene to be introduced into nerve cells may be produced by fusing a luminescence-related gene which expresses a photoprotein, a targeting base sequence that directs a photoprotein to another nerve cell, and a fluorescence-related gene which expresses a fluorescence protein. A process in which a photoprotein is transferred to another nerve cell from the nerve cell into which the fusion gene is introduced is confirmed by the fluorescent color emitted from the nerve cell, so that changes of the amount of luminescence in the nerve cell may be measured sequentially in the transferring process.

(Additional Remark)

There is provided a method for measuring fluorescence and luminescence, including:

a fluorescence measuring step of measuring fluorescence intensity emitted from a sample into which a fusion gene is introduced, the fusion gene being obtained by fusing a fluorescence-related gene which expresses a fluorescence protein and a luminescence-related gene which expresses a photoprotein including;

a position specifying step of specifying a position of the sample based on the fluorescence intensity measured by the fluorescence measuring step;

a luminescence measuring step of measuring luminescence intensity of luminescence emitted from the sample; and a luminescence amount quantifying step of quantifying the luminescence amount based on the luminescence intensity measured by the luminescence measuring step.

[II] Hereinbelow, embodiments of an expression amount measuring method in the present invention will be specifically described on the basis of the drawings. However, the present invention is not limited by these embodiments.

Figure 20:
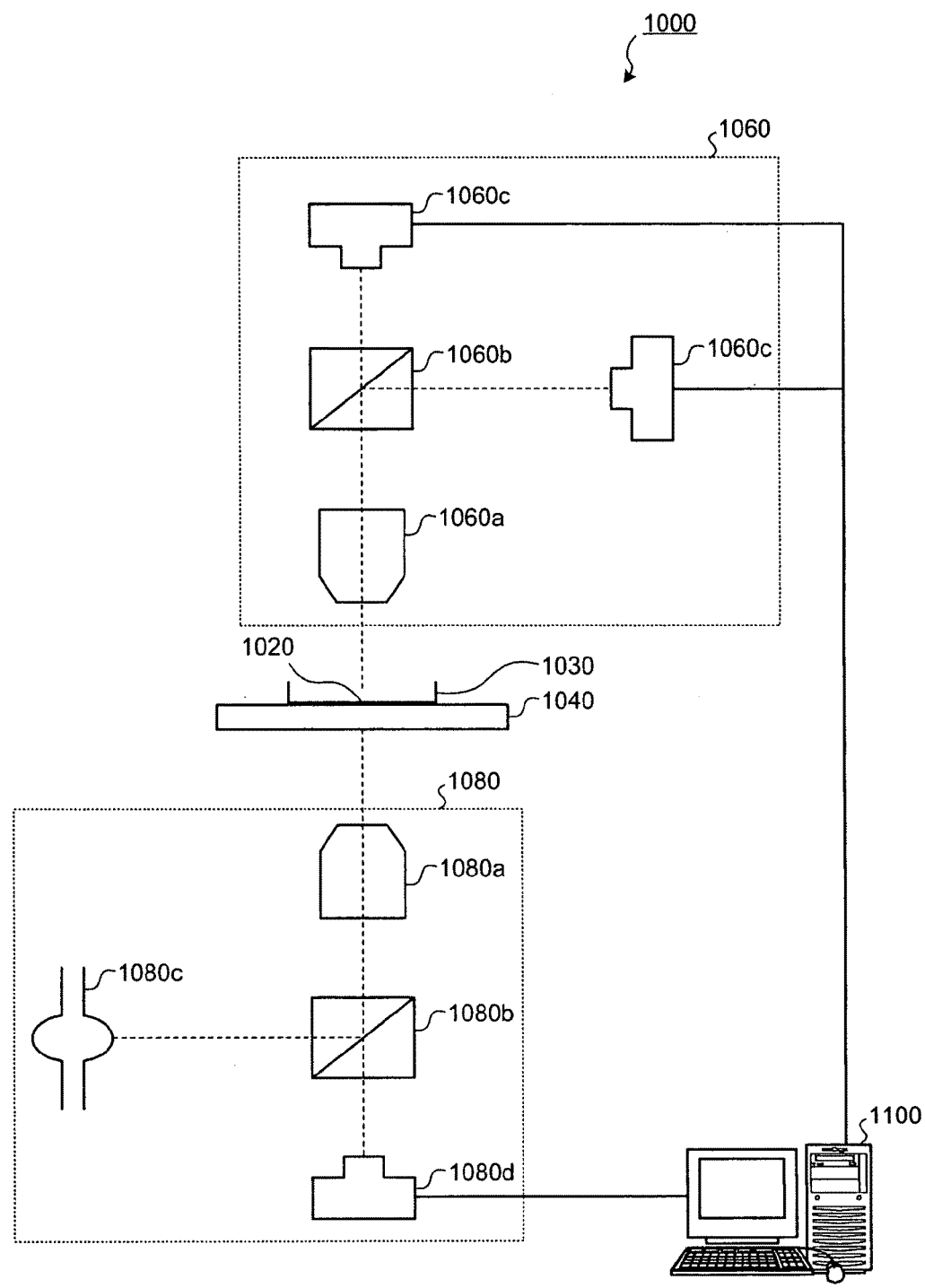
FIG. 20 is a diagram of an example of the entire configuration of an expression amount measuring apparatus 1000.

First, the configuration of an expression amount measuring apparatus 1000, that is an apparatus to perform the present invention, will be described with reference to FIGS. 20 to 22. FIG. 20 is a diagram of an example of the entire configuration of the expression amount measuring apparatus 1000.

As shown in FIG. 20, the expression amount measuring apparatus 1000 includes a cell 1020, a container 1030 accommodating the cell 1020 (specifically, a petri dish, a slide glass, a microplate, a gel supporting matrix, a particulate carrier, etc.), a stage 1040 on which the container 1030 is arranged, a luminescent image capturing unit 1060, a fluorescent image capturing unit 1080, and an information communication terminal 1100. In the expression amount measuring apparatus 1000, as shown in the figure, an objective lens 1060a included in the luminescent image capturing unit 1060 and an objective lens 1080a included in the fluorescent image capturing unit 1080 are arranged in vertically opposed positions across the cell 1020, the container 1030, and the stage 1040. The arrangement of the luminescent image capturing unit 1060 and the fluorescent image capturing unit 1080 may be replaced.

The cell 1020 may be a living cell into which a cell cycle-related gene expressed at the specific stage of the cell cycle is introduced in addition to a luminescence-related gene which expresses a photoprotein (specifically, luciferase), a fluorescence-related gene which expresses a fluorescence protein (specifically, GFP), and a gene to be analyzed. Here, the term "luminescence" used herein is a concept including bioluminescence and chemiluminescence.

The cell 1020 may be a living cell into which a fusion gene is introduced, the fusion gene being obtained by fusing the luminescence-related gene and the fluorescence-related gene, the gene to be analyzed, and the cell cycle-related gene. Specifically, the cell 1020 may be a living cell into which a vector obtained by fusing the luminescence-related gene and the fluorescence-related gene with the gene to be analyzed and the cell cycle-related gene is introduced. Further, the number of the genes to be analyzed introduced in combination with a luminescence related gene or a fluorescence related gene into the cell 1020 may be plural. In other words, plural pairs of a gene to be analyzed and a luminescence-related gene or a fluorescence-related gene may be introduced into the cell 1020. This allows for identifying the stage of the cell cycle and measuring the amount of expression of multiple genes to be analyzed introduced into the cell 1020.

When the stage of the cell cycle is identified by fluorescence and the amount of expression of the gene to be analyzed is measured by luminescence, the cell 1020 may be a living cell into which a fluorescence-related gene and a cell cycle-related gene are introduced in association with each other, and a luminescence-related gene and a gene to be analyzed are introduced in association with each other. Specifically, the cell 1020 may be a living cell into which a vector obtained by fusing a fluorescence-related gene with a cell cycle-related gene (specifically, a fluorescence-related gene introducing vector) is introduced and a vector obtained by fusing a luminescence-related gene with a gene to be analyzed (specifically, a luminescence-related gene introducing vector) is introduced. Alternatively, the vector into which a cell cycle-related gene promoter is incorporated may be introduced into the cell 1020. Specifically, a GFP sensor (manufactured by Amersham Bioscience) into which the Cyclin B1 promoter known as a cell-cycle marker is incorporated may be introduced into the cell 1020. The cell 1020 may be fluorescently labeled by introducing a HaloTag (registered trademark) vector (manufactured by Promega KK) therein and adding a HaloTag (registered trademark) ligand (manufactured by Promega KK) thereto. Alternatively, a luciferase vector into which the gene promoter for analysis is incorporated may be introduced into the cell 1020 to give expression thereof. Further, the cell 1020 may be labeled with luciferase by introducing a HaloTag (registered trademark) vector (manufactured by Promega KK) therein and adding a HaloTag (registered trademark) ligand (manufactured by Promega KK) thereto.

When the stage of the cell cycle is identified by fluorescence and the amount of expression of the gene to be analyzed is measured by luminescence, the cell 1020 may be a living cell into which a luminescence-related gene and a gene to be analyzed are introduced and which is stained with fluorescent substances at the predetermined site thereof (specifically, nucleus, cell membrane, cytoplasm, etc.). Specifically, the cell 1020 may be a living cell into which a fusion gene obtained by fusing a luminescence-related gene with a gene to be analyzed (specifically, a vector obtained by fusing a luminescence-related gene with a gene to be analyzed) is introduced and which is stained with fluorescent substances at the predetermined site thereof (specifically, nucleus, cell membrane, cytoplasm, etc.). Here, nuclei of cells 1020 may be stained with a live cell nuclear staining reagent "DRAQ5" (manufactured by Biostatus Limited). Further, cell membranes of cells 1020 may be stained with "PKH LinkerKits" (manufactured by SIGMA) (where in this case, cells in which the stage of the cell cycle can be identified by the shape (specifically, PC12 etc.) are used).

When the stage of the cell cycle is identified by luminescence and the amount of expression of the gene to be analyzed is measured by fluorescence, the cell 1020 may be a living cell into which a luminescence-related gene and a cell cycle-related gene are introduced in association with each other, and a fluorescence-related gene and a gene to be analyzed are introduced in association with each other. Specifically, the cell 1020 may be a living cell into which a vector obtained by fusing a luminescence-related gene with a cell cycle-related gene (specifically, a luminescence-related gene containing vector) is introduced and a vector obtained by fusing a fluorescence-related gene with a gene to be analyzed (specifically, a fluorescence-related gene containing vector) is introduced. Alternatively, the vector into which a cell cycle-related gene promoter is incorporated may be introduced into the cell 1020. Specifically, a luciferase vector into which the Cyclin B1 promoter is incorporated is produced, which is then introduced into the cell 1020. Further, the cell 1020 may be labeled with luciferase by introducing a HaloTag (registered trademark) vector (manufactured by Promega KK) therein and adding a HaloTag (registered trademark) ligand (manufactured by Promega KK) thereto. Alternatively, a fluorescent protein vector into which the gene promoter for analysis is incorporated may be introduced into the cell 1020 to give expression thereof. The cell 1020 may be fluorescently labeled by introducing a HaloTag (registered trademark) vector (manufactured by Promega KK) therein and adding a HaloTag (registered trademark) ligand (manufactured by Promega KK) thereto. Furthermore, a β-lactamase gene as a reporter gene may be introduced into the cell 1020.

Usable examples of the cell cycle-related gene include cycline (specifically, Cyclin A1, Cyclin A2, Cyclin B1, Cyclin B2, Cyclin B3, Cyclin C, Cyclin D1, Cyclin D2, Cyclin D3, Cyclin E1, Cyclin E2, Cyclin F, Cyclin G1, Cyclin G2, Cyclin H, Cyclin I, Cyclin T1, Cyclin T2a, Cyclin T2b, etc.), cycline kinases (specifically, CDK2, CDK28, etc.), and the like. Usable examples of the gene to be analyzed include the cell cycle-related gene described above, circadian rhythm-regulated genes such as period genes, Kai genes, timeless genes, per genes, and clock genes, other genes whose relationship to the cell cycle is unknown, and the like.

Describing FIG. 20 again, the luminescent image capturing unit 1060 is specifically an upright luminescence microscope and captures a luminescent image of the cell 1020. As shown in the drawing, the luminescent image capturing unit 1060 includes an objective lens 1060a, a dichroic mirror 1060b, and a CCD camera 1060c. Specifically, the objective lens 1060a has a value not less than 0.01 found by (Numerical Aperture/magnification)$^2$. The dichroic mirror 1060b is used to separate luminescence emitted from the cell 1020 according to color and measure luminescence intensity according to color using two-color luminescence. The CCD camera 1060c captures the luminescent image and bright-field image of the cell 1020 that are projected on the chip surface of the CCD camera 1060c through the objective lens 1060a. The CCD camera 1060c is connected to the information communication terminal 1100 to enable either wired or wireless communication. Here, when cells 1020 are present in an area to be captured, the CCD camera 1060c may capture the luminescent image and bright-field image of the cells 1020 that are in the area to be captured. FIG. 20 depicts one example where luminescent images corresponding to two luminescence separated by the dichroic mirror 1060b are separately captured by two CCD cameras 1060c. When one luminescence is used, the luminescent image capturing unit 1060 may include the objective lens 1060a and one CCD camera 1060c.

Figure 21:
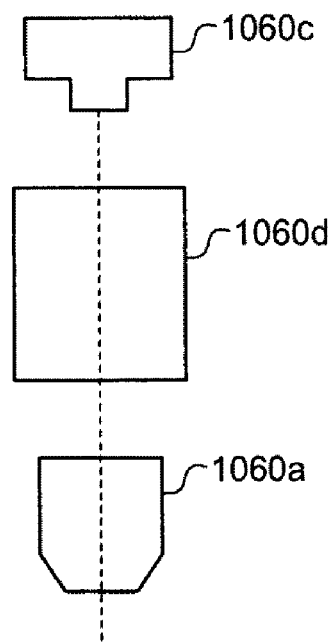
FIG. 21 is a diagram of an example of the configuration of a luminescent image capturing unit 1060 of the expression amount measuring apparatus 1000.

Here, when the luminescence intensity is measured according to color using two-color luminescence, the luminescent image capturing unit 1060 may include, as shown in FIG. 21, the objective lens 1060a, the CCD camera 1060c, and a split image unit 1060d. The CCD camera 1060c may capture the luminescent image (split image) and bright-field image of the cell 1020 that are projected on the chip surface of the CCD camera 1060c through the split image unit 1060d. As with the dichroic mirror 1060b, the split image unit 1060d is used to separate the luminescence emitted from the cell 1020 according to color and measure luminescence intensity according to color using two-color luminescence.

Figure 22:
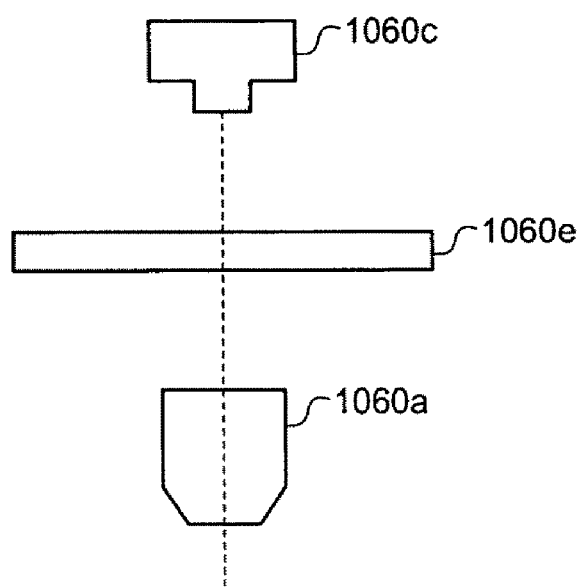
FIG. 22 is a diagram of another example of the configuration of the luminescent image capturing unit 1060 of the expression amount measuring apparatus 1000.

Further, when the luminescence intensity is measured according to color using plural-color luminescence (namely, when multicolored luminescence is used), the luminescent image capturing unit 1060 may include, as shown in FIG. 22, the objective lens 1060a, the CCD camera 1060c, and a filter wheel 1060e. The CCD camera 1060c may capture the fluorescent image and bright-field image of the cell 1020 that are projected on the chip surface of the CCD camera 1060c through the filter wheel 1060e. The filter wheel 1060e is used to replace the filter to separate the luminescence emitted from the cell 1020 according to color and measure luminescence intensity according to color using plural-color luminescence.

Referring to FIG. 20 again, the fluorescent image capturing unit 1080 is specifically an inverted fluorescence microscope and captures a fluorescent image of the cell 1020. As shown in the drawing, the fluorescent image capturing unit 1080 includes the objective lens 1080a, a dichroic mirror 1080b, a xenon lamp 1080c, and a CCD camera 1080d. The CCD camera 1080d captures the fluorescent image and bright-field image of the cell 1020 that are projected on the chip surface of the CCD camera 1080d through the objective lens 1080a. The CCD camera 1080d is connected to the information communication terminal 1100 to enable either wired or wireless communication. Here, when cells 1020 are present in an area to be captured, the CCD camera 1080d may capture the fluorescent image and bright-field image of the cells 1020 that are in the area to be captured. The dichroic mirror 1080b transmits the fluorescence from the cell 1020 and changes the direction of excitation light so as to irradiate the cell 1020 with the excitation light emitted from the xenon lamp 1080c. The xenon lamp 1080c emits excitation light.

Here, the luminescent image capturing unit 1060 and the fluorescent image capturing unit 1080 may be specifically an inverted luminescence microscope and an inverted fluorescence microscope, respectively. The stage 1040 may be a rotation stage.

Figure 23:
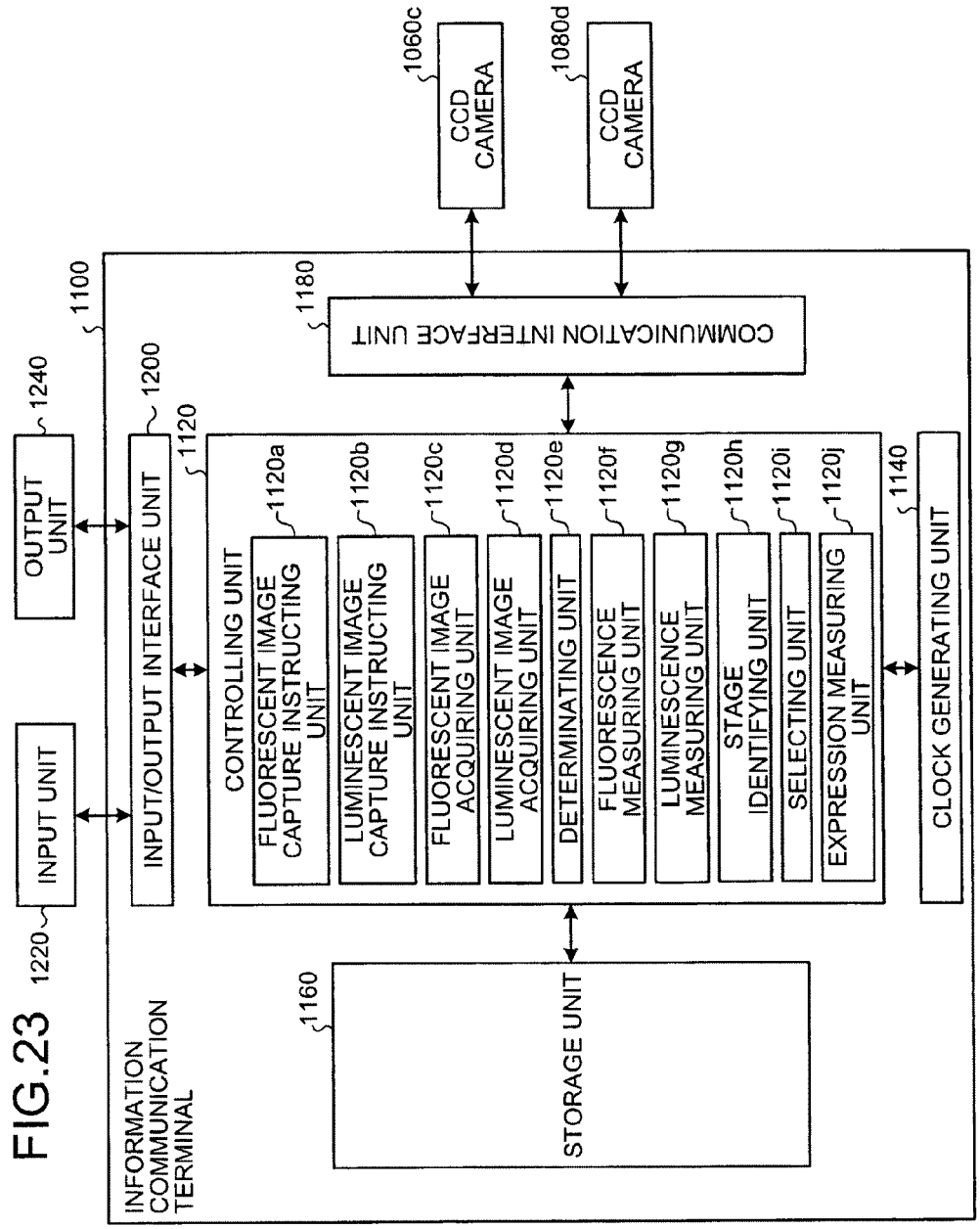
FIG. 23 is a block diagram of an example of the configuration of an information communication terminal 1100 of the expression amount measuring apparatus 1000.

The information communication terminal 1100 is specifically a personal computer. As shown in FIG. 23, the information communication terminal 1100 includes, when classified roughly, a controlling unit 1120, a clock generating unit 1140 that generates a clock for the system, a storage unit 1160, a communication interface unit 1180, an input/output interface unit 1200, an input unit 1220, and an output unit 1240. These respective units are connected through a bus.

The storage unit 1160 is storage means, and usable examples thereof include memory devices such as RAM and ROM; fixed disk devices such as hard disks; flexible disks; and optical disks. The storage unit 1160 stores data obtained by processing of each unit in the controlling unit 1120.

The communication interface unit 1180 mediates communications in the information communication terminal 1100, the CCD camera 1060c, and the CCD camera 1080d. That is, the communication interface unit 1180 has a function of communicating data with other terminals via wired or wireless communication lines.

The input/output interface unit 1200 is connected to the input unit 1220 or the output unit 1240. Here, in addition to a monitor (including household-use televisions), a speaker or a printer can be used as the output unit 1240 (hereinafter, the output unit 1240 is sometimes described as a monitor). Further, a monitor which cooperates with a mouse to realize a pointing device function can be used as the input unit 1220 in addition to a microphone, a keyboard, and a mouse.

The controlling unit 1120 has an internal memory to store a control program such as OS (Operating System), a program in which various kinds of procedures are defined, and required data, and performs various processing based on these programs. The controlling unit 1120 includes, when classified roughly, a fluorescent image capture instructing unit 1120a, a luminescent image capture instructing unit 1120b, a fluorescent image acquiring unit 1120c, a luminescent image acquiring unit 1120d, a determining unit 1120e, a fluorescence measuring unit 1120f, a luminescence measuring unit 1120g, a stage identifying unit 1120h, a selecting unit 1120i, and an expression measuring unit 1120j.

The fluorescent image capture instructing unit 1120a instructs the CCD camera 1080d to capture a fluorescent image or a bright-field image through the communication interface unit 1180. The luminescent image capture instructing unit 1120b instructs the CCD camera 1060c to capture a luminescent image or a bright-field image through the communication interface unit 1180. The fluorescent image acquiring unit 1120c obtains the fluorescent image and bright-field image captured by the CCD camera 1080d through the communication interface unit 1180. The luminescent image acquiring unit 1120d obtains the luminescent image and bright-field image captured by the CCD camera 1060c through the communication interface unit 1180.

The determining unit 1120e determines whether respective genes are introduced or not into each cell 1020 based on the fluorescent image and/or the luminescent image. The fluorescence measuring unit 1120f individually measures fluorescence intensity emitted from each cell 1020 based on the fluorescent image captured by the CCD camera 1080d. The luminescence measuring unit 1120g individually measures luminescence intensity of luminescence emitted from each cell 1020 based on the luminescent image captured by the CCD camera 1060c.

The stage identifying unit 1120h identifies the stage of the cell cycle for each cell 1020 by determining whether a cell cycle-related gene is expressed or not in each cell 1020 on the basis of the fluorescence intensity measured by the fluorescence measuring unit 1120f or the luminescence intensity measured by the luminescence measuring unit 1120g. When identifying a living cell 1020 into which a luminescence-related gene and a gene to be analyzed are introduced and which is stained with a fluorescent substance at the predetermined site (specifically, nucleus, cell membrane, cytoplasm, etc.), the stage of the cell cycle may be identified by determining whether or not the shape of the cell 1020 is changed based on the fluorescent image captured by the CCD camera 1080d. The selecting unit 1120i selects the cells 1020 for measurement from among the cells 1020 whose stages are identified by the stage identifying unit 1120h.

The expression measuring unit 1120j measures the amount of expression of the gene to be analyzed based on the measured fluorescence intensity by the fluorescence measuring unit 1120f when luminescence intensity is used in the stage identifying unit 1120h in the selected cells 1020 by the selecting unit 1120i, and measures the amount of expression of the gene to be analyzed based on the measured luminescence intensity by the luminescence measuring unit 1120g when fluorescence intensity or fluorescent image is used in the stage identifying unit 1120h. In this regard, the expression measuring unit 1120j may measure the amount of expression of the gene to be analyzed in cells 1020 or the selected cells 1020 by the selecting unit 1120i based on the measured fluorescence intensity by the fluorescence measuring unit 1120f, and may identify expression sites in cells 1020 of the gene to be analyzed based on the captured fluorescent image by the CCD camera 1080d.

Figure 24:
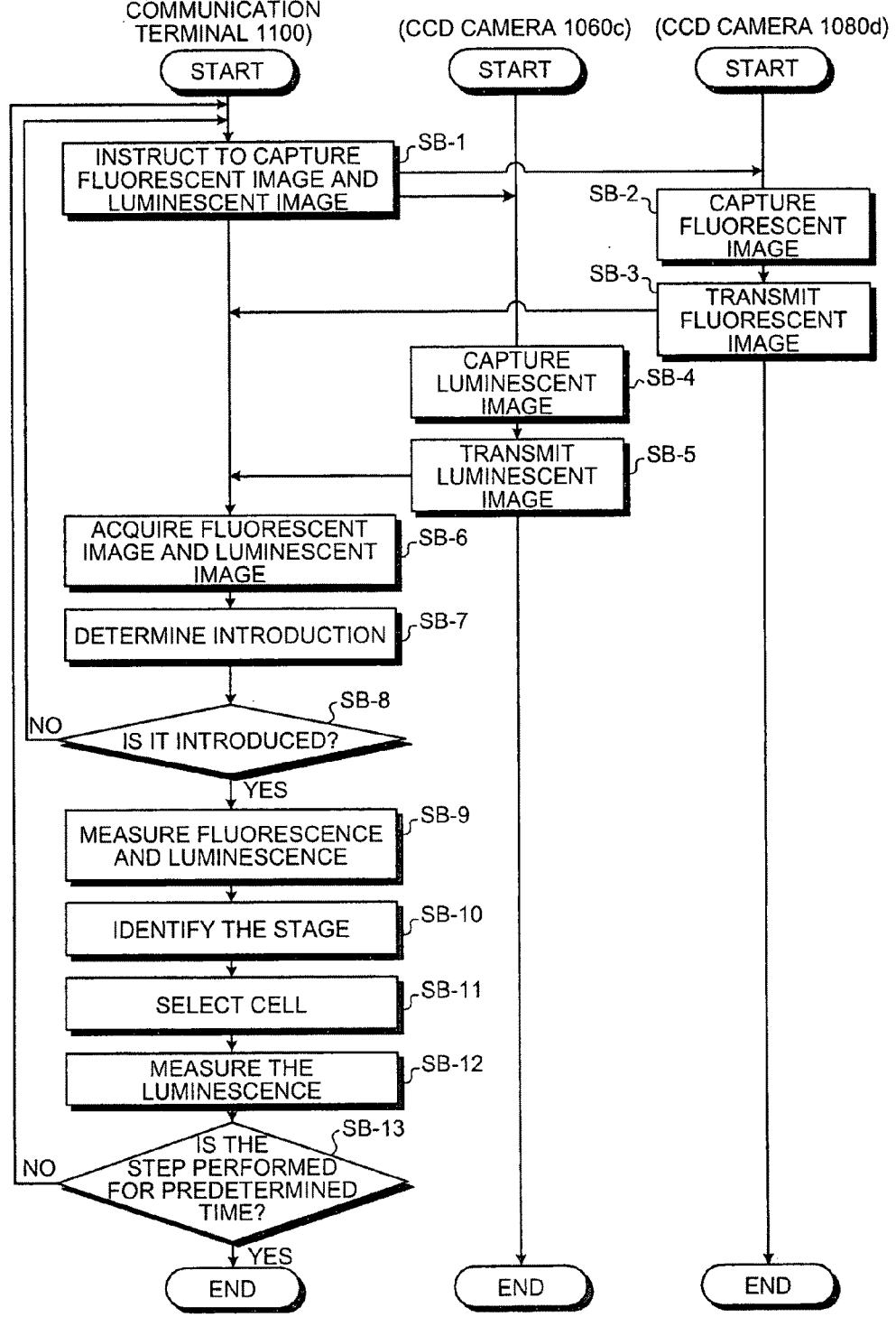
FIG. 24 is a flow chart of an example of a processing that is performed by the expression amount measuring apparatus 1000.

In the above configuration, one example of the processing performed by the expression amount measuring apparatus 1000 will be described with reference to FIG. 24. That is, a vector obtained by fusing a luminescence-related gene and a cell cycle-related gene and a vector obtained by fusing a fluorescence-related gene and a gene to be analyzed are introduced into cells 1020. While the stage of the cell cycle in a specific cell 1020 among the cells 1020 is identified by the luminescence intensity, the amount of expression of the gene to be analyzed is measured by the fluorescence intensity sequentially, and the expression site in the cell 1020 of the gene to be analyzed is identified by a fluorescent image sequentially.

First, the information communication terminal 1100 instructs the CCD camera 1080d to capture a fluorescent image through the communication interface unit 1180 in processing of the fluorescent image capturing instruction unit 1100a, and instructs the CCD camera 1060c to capture a luminescent image through the communication interface unit 1180 in processing of the luminescent image capture instructing unit 1120b (step SB-1). Next, the CCD camera 1080d captures a fluorescent image of the cells 1020 that are in the area to be captured (step SB-2), and transmits it to the information communication terminal 1100 (step SB-3). On the other hand, the CCD camera 1060c captures a luminescent image of the cells 1020 that are in the area to be captured (step SB-4), and transmits it to the information communication terminal 1100 (step SB-5). The instruction to capture a fluorescent image and the instruction to capture a luminescent image may be performed at different times or different time intervals. For example, a luminescent image to be used for identifying the stage of the cell cycle may be captured every several hours, and a fluorescent image to be used for measuring the amount of expression of the gene to be analyzed may be captured every several minutes. Additionally, the cell 1020 is irradiated with excitation light only when capturing a fluorescent image.

Next, the information communication terminal 1100 includes:
(a) obtaining a fluorescent image through the communication interface unit 1180 in processing of the fluorescent image acquiring unit 1120c;
(b) obtaining a luminescent image through the communication interface unit 1180 in processing of the luminescent image acquiring unit 1120d;
(c) obtaining a time clock from the clock generating unit 1140 in processing of the controlling unit 1120; and
(d) storing correspondingly the fluorescent image, luminescent image, and the time clock which are obtained and storing them in a predetermined storage area of the storage unit 1160 (step SB-6).

Next, the information communication terminal 1100 determines whether a vector is introduced or not into each cell 1020 based on the fluorescent image and/or the luminescent image in the processing of the determining unit 1120e (step SB-7). When at least one cell 1020 into which a vector is introduced is present (step SB-8: Yes), the information communication terminal 1100 measures fluorescence intensity of the fluorescence emitted from each cell 1020 by processing of the fluorescence measuring unit 1120f based on the fluorescent image, and measures luminescence intensity of the luminescence emitted from each cell 1020 by processing of the luminescence measuring unit 1120g based on the luminescent image (step SB-9).

Next, the information communication terminal 1100 identifies the stage of the cell cycle for each cell 1020 by determining whether the cell cycle-related gene is expressed or not in each cell 1020 based on the luminescence intensity in the processing of the stage identifying unit 1120h (step SB-10). In this regard, when a vector which is fused with a fluorescence-related gene and a cell cycle-related gene as well as a vector which is fused with a luminescence-related gene and a gene to be analyzed are introduced into cells 1020, the stage of the cell cycle may be identified for each cell 1020 by determining whether a cell cycle-related gene is expressed or not in each cell 1020. When a vector which is fused with a luminescence-related gene and the gene to be analyzed is introduced into cells 1020 and the predetermined site (specifically, nucleus, cell membrane, cytoplasm, etc.) are stained with fluorescent substances, the stage of the cell cycle may be identified by determining whether or not the shape of the cell 1020 is changed based on the fluorescent image for each cell 1020.

Next, the information communication terminal 1100 selects the cell 1020 for measurement from among the cells 1020 whose stages are identified at step SA-10 in the processing of the selecting unit 1120i (step SB-11). Then, the information communication terminal 1100 measures the amount of expression of the gene to be analyzed in the selected cells 1020 at step SB-11 based on the measured fluorescence intensity, and identifies expression sites of the gene to be analyzed in the cells 1020 based on the captured fluorescent image in the processing of the expression measuring unit 1120j (step SB-12). When the fluorescence intensity or the fluorescent image is used in SB-10, the expression amount of the gene to be analyzed may be measured based on the luminescence intensity in step SB-12.

The information communication terminal 1100 repeatedly performs the above-mentioned processing steps SB-1 to step SB-12 at the time interval that is set up in advance predetermined times in processing of the controlling unit 1120, and stopping the processing when the step is performed for predetermined times (step SB-13: Yes).

Here, only the image capture and acquisition of a luminescent image and a fluorescent image are repeatedly performed, so that measurement of luminescence intensity, measurement of fluorescence intensity, identification of the stage, selection of the cell 1020, and measurement of the expression amount may be performed at the time of analysis. That is, only the luminescent image and fluorescent image which are original data required for analysis are obtained collectively, and then measurement of luminescence intensity, measurement of fluorescence intensity, identification of the stage, selection of the cell 1020, and measurement of the expression amount may be performed at the time of analysis. Specifically, selection of the cell 1020 and measurement of the expression amount may be performed at the time of analysis after obtaining of a luminescent image and a fluorescent image. Further, identification of the stage and selection of the cell 1020 may be performed at the time of analysis after obtaining a luminescent image and a fluorescent image. Furthermore, selection of the cell 1020 may be performed at the time of analysis after obtaining a luminescent image and a fluorescent image.

After obtaining a fluorescent image, the cell 1020 for measurement may be selected and a luminescent image may be obtained.

As described in detail above, according to the expression amount measuring apparatus 1000, in living cells 1020 into which a luminescence-related gene, a fluorescence-related gene, and a gene to be analyzed are introduced, the luminescence intensity of the luminescence emitted from cells 1020 is measured, the fluorescence intensity of the fluorescence emitted from cells 1020 is measured, and the amount of expression of a gene to be analyzed is measured based on the measured luminescence intensity or the measured fluorescence intensity. In this case, the cells are cells into which the cell cycle-related gene is introduced in addition to the luminescence-related gene, the fluorescence-related gene, and the gene to be analyzed. The stage of the cell cycle is identified by determining whether a cell cycle-related gene is expressed or not based on the measured fluorescence intensity when luminescence intensity is used to measure the amount of expression, or based on the measured luminescence intensity when fluorescence intensity is used to measure the amount of expression. Thus, when the amount of expression of the gene to be analyzed introduced into cells 1020 is measured, the stage of the cell cycle can be identified in cells 1020 without performing the synchronized culture method, resulting in reducing the procedural burden on experimenters. Further, that produces an effect in which the relationship between the gene to be analyzed and the stage of the cell cycle can be evaluated. Specifically, with reference to the gene to be analyzed whose direct involvement in the cell cycle is unknown, change in expression which is caused by administration of a medicine or temperature changes can be obtained in addition to the stage of the cell cycle, which allows for verifying the relation between the gene to be analyzed and the cell cycle. Further, with reference to the gene to be analyzed considered to be directly involved in the cell cycle, both the amount of expression of the gene to be analyzed and the stage of the cell cycle can be obtained, thereby enabling to evaluate whether the gene to be analyzed is useful as a cell-cycle marker. When living cells 1020 into which a luminescence-related gene that expresses a photoprotein and the gene to be analyzed are introduced and stained with fluorescent substances at the predetermined site (specifically, nucleus, cell membrane, cytoplasm, etc.), the expression amount measuring apparatus 1000 may measure the luminescence intensity of the luminescence emitted from the cell 1020 and measure the amount of expression of the gene to be analyzed based on the measured luminescence intensity and capture the fluorescent image of the cell 1020 and identify the stage of the cell cycle by determining whether or not the shape of the cell 1020 is changed based on the fluorescent image captured by the CCD camera 1080*d*. In this regard, with exception of the method for confirming incorporation of a luminescence inducing protein gene, fluorochrome may be used in place of a fluorescence fusion gene, while the number of times as for the image capture for a fluorochrome can be decreased compared to the case of the image capture only for fluorescence in order to minimize the effect of phototoxicity by excitation light. Further, the expression amount measuring apparatus 1000 can be preferably used in, for example, examinations of various types of reactions (for example, drug stimulation, light exposure, etc.) or treatments.

Here, cells at various stages have been handled as a group of data in performing the reporter assay. The cell cycle includes multiple consecutive reactions consisting of the growth of cells, the DNA duplication, the distribution of chromosomes, the cell division, and the like.

Therefore, it is just conceivable that the expression of various genes varies depending on each stage of the cell cycle. Consequently, use of the expression amount measuring apparatus 1000 provides the following effect. When with reference to the gene to be analyzed whose direct involvement in the cell cycle is unknown, change in expression which is caused by a certain stimulation such as administration of a medicine, temperature changes, or the like is detected, and more detailed analysis results can be obtained by matching to data on the stage of the cell cycle. When the expression amount measuring apparatus 1000 is used, the stage of the cell cycle as for the gene whose direct involvement in the cell cycle is suggested can be discriminated for each cell. Thus, operation such as the synchronized culture that has conventionally been performed is not needed and only the cell whose stage is desired to analyze can be selected and observed.

According to the expression amount measuring apparatus 1000, when cells 1020 are present in an area to be captured, a fluorescent image of the cells 1020 is captured and a luminescent image of cells 1020 is captured. Luminescence intensity of the luminescence emitted from each cell 1020 is respectively measured based on the captured luminescent image, and fluorescence intensity of the fluorescence emitted from each cell 1020 is respectively measured based on the captured fluorescent image. Then, the amount of expression of the gene to be analyzed for each cell 1020 is measured based on the measured luminescence intensity or the measured fluorescence intensity. The stage of the cell cycle is identified for each cell 1020 by determining whether a cell cycle-related gene is expressed or not in each cell 1020 based on the measured fluorescence intensity when luminescence intensity is used to measure the amount of expression, or based on the measured luminescence intensity when fluorescence intensity is used to measure the amount of expression. This allows for measuring the amount of expression of the gene to be analyzed, in each of the cells 1020 and identifying the stage of the cell cycle for each cell 1020. Further, this produces an effect in which the relationship between the gene to be analyzed and the stage of the cell cycle can be evaluated for each cell 1020. Living cells 1020 are identified in which a luminescence-related gene that expresses a photoprotein and the gene to be analyzed are introduced and are stained with fluorescent substances at the predetermined site (specifically, nucleus, cell membrane, cytoplasm, etc.). In this case, the expression amount measuring apparatus 1000 captures a luminescent image of the cells 1020 in the area, captures a fluorescent image of the cells 1020, measures luminescence intensity of the luminescence emitted from each cell 1020, and measures the expression amount of the gene to be analyzed based on the measured luminescence intensity, so as to identify the stage of the cell cycle for each cell 1020 by determining whether the shape of the cell 1020 is changed or not for each cell 1020 based on the fluorescent image captured by the CCD camera 1080*d*. Alternatively, comparative evaluation of cells with the same conditions may be performed by comparing for each cell cycle stage.

According to the expression amount measuring apparatus 1000, the cell 1020 for measurement is selected from among cells 1020 whose stages are identified, and the amount of expression of the gene to be analyzed introduced into the selected cell 1020 is measured based on the measured luminescence intensity or the measured fluorescence intensity. Thus, individual cells 1020 are distinguished from one another, and the amount of expression of the gene to be analyzed is measured in a single cell 1020 and the stage of the cell cycle can be identified.

According to the expression amount measuring apparatus 1000, the amount of expression of the gene to be analyzed is measured sequentially by repeatedly performing the capture of a luminescent image, the capture of a fluorescent image, the measurement of luminescence intensity, the measurement of fluorescence intensity, the identification of the stage, the selection of cells 1020, and the measurement of the amount of expression while the stage of the cell cycle is identified in the selected cells 1020. Thus, change in expression of the gene to be analyzed can be measured sequentially in a single cell 1020 while the stage of the cell cycle is identified. When a luminescence-related gene which expresses a photoprotein and a gene to be analyzed are introduced and living cells 1020 which are stained with fluorescent substances at the predetermined site (specifically, nucleus, cell membrane, cytoplasm, etc.) are used, the expression amount measuring apparatus 1000 may measure the amount of expression of the gene to be analyzed sequentially by repeatedly performing the capture of a luminescent image, the capture of a fluorescent image, the measurement of luminescence intensity, the identification of the stage, the selection of cells 1020, and the measurement of the amount of expression while the stage of the cell cycle is identified in the selected cells 1020. Alternatively, a moving image (or frame advance) in which the cell cycle is matched or one image may be displayed by viewing an image on the time-lapse image in which different cells in the same visual field are captured at the time depending on each cell cycle or one image at the same time.

According to the expression amount measuring apparatus 1000, in measurement of the amount of expression, the amount of expression of the gene to be analyzed is measured in the selected cells 1020 based on the measured fluorescence intensity and expression sites in cells 1020 of the gene to be analyzed are identified based on the captured fluorescent image. This allows for not only the evaluation of the relationship between the gene to be analyzed and the stage of the cell cycle, but also the identification of the expression site in the cell 1020 of the gene to be analyzed.

Further, the use of expression amount measuring apparatus 1000 allows for evaluation of, for example, anticancer drug and its lead compound. Particularly, it can monitor whether an anticancer drug has a harmful effect on the efficiency of cell division or whether its lead compound affects the transcriptional activity of genes to be analyzed at the same time. Furthermore, the use of the expression amount measuring apparatus 1000 allows for examination of, for example, the relationship between the cell cycle and morphology of cells. Especially, it is known that the cellular morphology as for PC12 cell varies depending on the stage of the cell cycle and differentiation stage. Detailed stage identification by cell morphology can be performed in other neuroid cells and the cell morphology itself can be used as a phase marker of the cell cycle or differentiation. Further, when the expression amount measuring apparatus 1000 is used, for example, the expression period of the gene which can be involved in the cell cycle and their localization are identified by detecting the fluorescence while the cell cycle is monitored by detecting the luminescence. This allowed for evaluating whether there is a relationship between the gene to be analyzed and the cell cycle, and the usefulness of the gene to be analyzed as cell-cycle markers.

(III) Hereinbelow, exemplary embodiments of the microscope unit and microscope apparatus as the measuring apparatus according to the present invention will be described in detail with reference to the accompanying drawings. However, the present invention is not limited by these embodiments. In addition, it should be noted that the same numeral references are applied to the same parts in the description of the drawings.

First Embodiment

Figure 25:
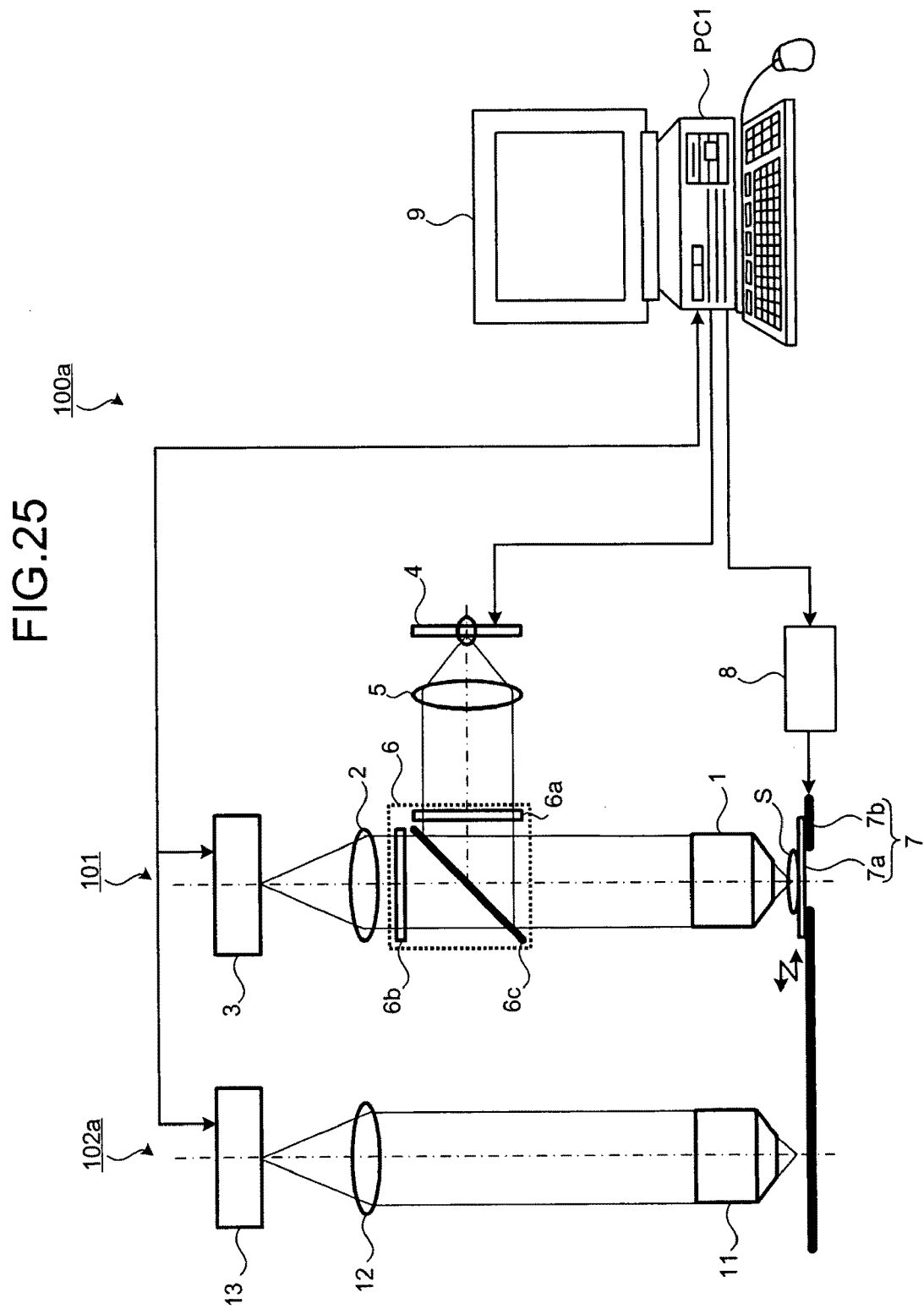
FIG. 25 is a diagram of the configuration of a microscope apparatus according to a first embodiment of the present invention.

First, a microscope apparatus according to a first embodiment of the present invention will be described. FIG. 25 is a schematic diagram of the configuration of the microscope apparatus according to the first embodiment of the invention. As shown in FIG. 25, a microscope apparatus 100a according to the first embodiment includes a fluorescence microscope unit 101 that performs the observation of fluorescence, a weak luminescence microscope unit 102a that observes weak luminescence, a holding unit 7 as holding means which holds a specimen S in which a luminescent label and a fluorescent label are given, a monitor 9 that displays such as a specimen image of the specimen S captured by respective microscope units 101 and 102a, and a control device PC1 that controls all processing and movement of the microscope apparatus 100a. The fluorescence microscope unit 101 and the weak luminescence microscope unit 102a are arranged adjacent each other.

The fluorescence microscope unit 101 includes: a fluorescence imaging optical system of high magnification that has an objective lens 1 as a fluorescence objective lens and an imaging lens 2 as a fluorescence imaging lens: an imaging device 3 as fluorescence imaging means that captures a fluorescent specimen image which is the specimen image of the specimen S formed by the fluorescence imaging optical system; an excitation light source 4 that emits excitation light that excites the specimen S; a lens 5 that concentrates the excitation light from the excitation light source 4, and a fluorescence cube 6 as a fluorescence unit.

The objective lens 1 has a large numerical aperture on the side of the specimen, and converts the fluorescence emitted from each point of the luminescent label given to the specimen S into a substantially parallel pencil of rays. The imaging lens 2 concentrates the fluorescence converted into a substantially parallel pencil of rays by the objective lens 1 and forms a fluorescent specimen image that is the specimen image of the specimen S. The fluorescence imaging optical system forms a fluorescent specimen image at high magnification of 40 times or more. The imaging device 3 has a solid state image sensor such as CCD and CMOS, and captures a fluorescent specimen image that is formed on the imaging surface of the solid state image sensor and then produces image data to output it to control device PC1.

The fluorescence cube 6 integrally includes an excitation filter 6a as an excitation light transmitting filter that selectively transmits excitation light for exciting the specimen S, an absorption filter 6b as a fluorescence transmitting filter that selectively transmits the fluorescence emitted from the specimen S excited by the excitation light, and a dichroic mirror 6c that reflects the excitation light and transmits fluorescence. The excitation filter 6a is a band pass filter that extracts the excitation light of a predetermined wavelength band from the lights of various wavelengths emitted from the excitation light source 4. The absorption filter 6b is a long wave pass filter with a predetermined cutoff wavelength. Here, the absorption filter 6b may be a band pass filter that extracts the fluorescence of a predetermined wave range. The band pass filter is effective when the wavelengths of the weak luminescence and fluorescence emitted from the specimen S are close.

The excitation light source 4 is realized by a mercury lamp, a xenon lamp, a laser, and the like. As excitation light irradiating means, the excitation light source 4 and the lens 5 reflect the excitation light emitted from the excitation light source 4 through the excitation filter 6a by the dichroic mirror 6c and irradiate the specimen S with it. In this regard, the excitation light source 4 lights up and out in accordance with instructions from the control device PC1.

The weak luminescence microscope unit 102a includes a weak luminescence imaging optical system of low magnification that has an objective lens 11 as a weak luminescence objective lens and an imaging lens 12 as a weak luminescence imaging lens, and an imaging device 13 as weak luminescence capturing means that captures a weak luminescent specimen image which is the specimen image of the specimen S formed by the weak luminescence imaging optical system.

The objective lens 11 has a large numerical aperture on the side of the specimen, and converts weak luminescence that is self-emitted from each point of the luminescent label that is given to the specimen S into a substantially parallel pencil of rays. The imaging lens 12 concentrates the weak luminescence converted into a substantially parallel pencil of rays by the objective lens 11 and forms a weak luminescent specimen image that is the specimen image of the specimen S. The weak luminescence imaging optical system forms the weak luminescent specimen image at an imaging magnification lower than that of the fluorescence imaging optical system. Here, it is desirable that the weak luminescence imaging optical system satisfies $(NAo/\beta)^2 \geqq 0.01$ when the numerical aperture (NA) on the side of the specimen is defined as NAo and the imaging magnification is defined as $\beta$.

The imaging device 13 has a solid state image sensor, such as CCD and CMOS, and captures the weak luminescent specimen image that is formed on the imaging surface of the solid state image sensor and then produces image data to outputs it to the control device PC1. In this regard, the solid state image sensor included in the imaging device 13 is a highly-sensitive monochrome CCD and it is preferable to use a cooled CCD (at about 0° C.).

The holding unit 7 has a holding member 7a such as a prepared slide, a slide glass, a microplate, a gel supporting matrix, a particulate carrier, and an incubator on which the specimen S is directly placed, and a movable stage 7b that two-dimensionally moves the specimen S together with the holding member 7a. The movable stage 7b is driven by a stage driving unit 8 in accordance with instructions from the control device PC1.

The control device PC1 is realized by a processor, such as a computer with CPU, and electrically connects the imaging devices 3 and 13, the excitation light source 4, the stage driving unit 8, and the monitor 9, thereby to control the movement of the respective structural parts. Particularly, as image capture switch controlling means, the control device PC1 controls the image capture switching processing that switches between the capture of a weak luminescent specimen image by the weak luminescence microscope unit 102a and the capture of a fluorescent specimen image by the fluorescence microscope unit 101 on the basis of the image characteristic of the weak luminescent specimen image captured by the imaging device 13.

Figure 26:
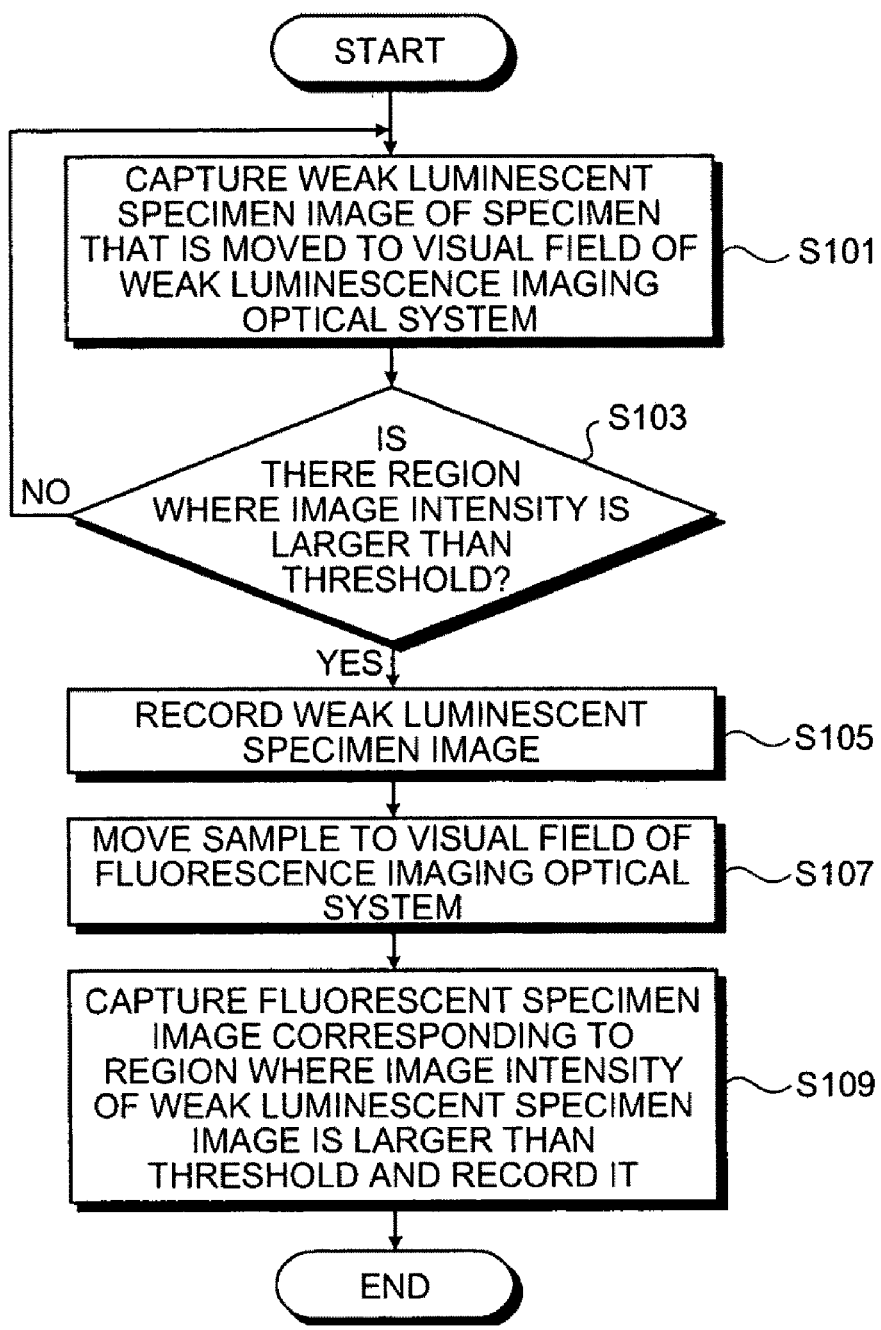
FIG. 26 is a flow chart of the procedure for an image switching processing in which the microscope apparatus shown in FIG. 25 switches between observation of weak luminescence and observation of fluorescence.

Here, the image capture switching processing controlled by the control device PC1 will be described. FIG. 26 is a flow chart of the procedure for image capture switching processing. As shown in FIG. 26, the control device PC1 captures the weak luminescent specimen image of the specimen S that is moved to a visual field of the weak luminescence imaging optical system by the movable stage 7b (step S101). On the basis of the captured result, the control device PC1 determines whether or not there is a region where the image intensity as the image characteristic of a weak luminescent specimen image is larger than a preset threshold in a weak luminescent specimen image (step S103). When it is determined that there is no region where the image intensity is larger than the threshold (step S103: No), the control device PC1 repeatedly performs the processing from step S101.

On the other hand, when it is determined that there is a region where the image intensity is larger than the threshold (step S103: Yes), the control device PC1 records the weak luminescent specimen image captured by step S101 (step S105); and moves the specimen S to the visual field of the fluorescence imaging optical system by the movable stage 7b (step S107). The control device PC1 causes the imaging device 3 to capture the fluorescent specimen image corresponding to the region where the image intensity of the weak luminescent specimen image is larger than the threshold, and record it (step S109); and then the image capture switching processing is ended. In this regard, it is preferable that when daily observation of the specimen S is performed, the control device PC1 may make a control to move the specimen S to the visual field of the weak luminescence imaging optical system again by the movable stage 7b after step S109, and repeat the processing from step S101. Further, the capture in step S109 may be either time-lapse capture or one image. Alternatively, a moving image (or frame advance) in which the cell cycle is matched or one image may be displayed by viewing an image on the time-lapse image in which different cells in the same visual field are captured at the time depending on each cell cycle or one image at the same time.

In steps S105 and S109, the control device PC1 stores the captured weak luminescent specimen image and fluorescent specimen image in a storage unit such as RAM that is included therein. In steps S101 and S109, the control device PC1 may successively display the captured weak luminescent specimen image and fluorescent specimen image on the monitor 9. Further, it is preferable that the control device PC1 turns off the excitation light source 4 between steps S101 to S105, that is, while the weak luminescence of the specimen S is observed by the weak luminescence microscope unit 102a, and controls to turn on the excitation light source 4 when fluorescence of the specimen S is observed by step S109. Alternatively, a shading device such as a shutter is provided on the optical path from the excitation light source 4 to the fluorescence unit 6, and the control device PC1 may be configured to control the irradiation of excitation light by opening and closing the shading device instead of switching to turn on/off the excitation light source 4 as non-irradiating means.

In this regard, the control device PC1 is configured to determine the switch to fluorescent observation on the basis of the image intensity of partial region in a weak luminescent specimen image in step S103. It may be configured to determine the switch on the basis of the image intensity of the whole weak luminescent specimen image. The control device PC1 may obtain such image intensity, for example, as the cumulative image intensity from a predetermined time point up to the current time point or as the instantaneous image intensity at the current time. In this regard, when entire image intensity of the weak luminescent specimen image is obtained, a light-sensitive element such as a photomultiplier may be used in place of the imaging device 13.

As described above, according to the microscope apparatus in the first embodiment, the microscope apparatus includes the fluorescence microscope unit 101 for fluorescent observation and the weak luminescence microscope unit 102a for weak luminescent observation, which are adjacently arranged, and the movable stage 7b that moves the specimen S to each of the visual fields of the fluorescence imaging optical system and the weak luminescence imaging optical system. With this configuration, it is possible to switch the fluorescent observation and the weak luminescent observation properly and to switch from the observation of weak luminescence to the observation of fluorescence immediately depending on the image intensity as the image characteristic of the weak luminescent specimen image.

While weak luminescence imaging optical system has been described as an infinity-corrected optical system that forms a specimen image by the objective lens 11 and the imaging lens 12, it may be configured as a finite-corrected optical system that forms a specimen image by only the objective lens.

The observation of weak luminescence is switched to the observation of fluorescence on the basis of the image characteristics, such as the image intensity of the weak luminescent specimen image in the image capture switching processing mentioned above. The observation of weak fluorescence may be switched to the observation of luminescence on the basis of the image characteristics, such as image intensity of the fluorescent specimen image when the intensity of excitation light with which the specimen S is irradiated or the intensity of fluorescence which is emitted from the specimen S is weak in the observation of fluorescence and the damage to the specimen S caused by excitation light and fluorescence is relatively little.

Second Embodiment

Next, a second embodiment of the present invention will be described. In the first embodiment mentioned above, the specimen S is moved to each of the visual fields of the fluorescence imaging optical system and the weak luminescence imaging optical system by the movable stage 7b. On the other hand, in the second embodiment, the specimen S is arranged in each visual field by moving the fluorescence imaging optical system and the weak luminescence imaging optical system.

Figure 27:
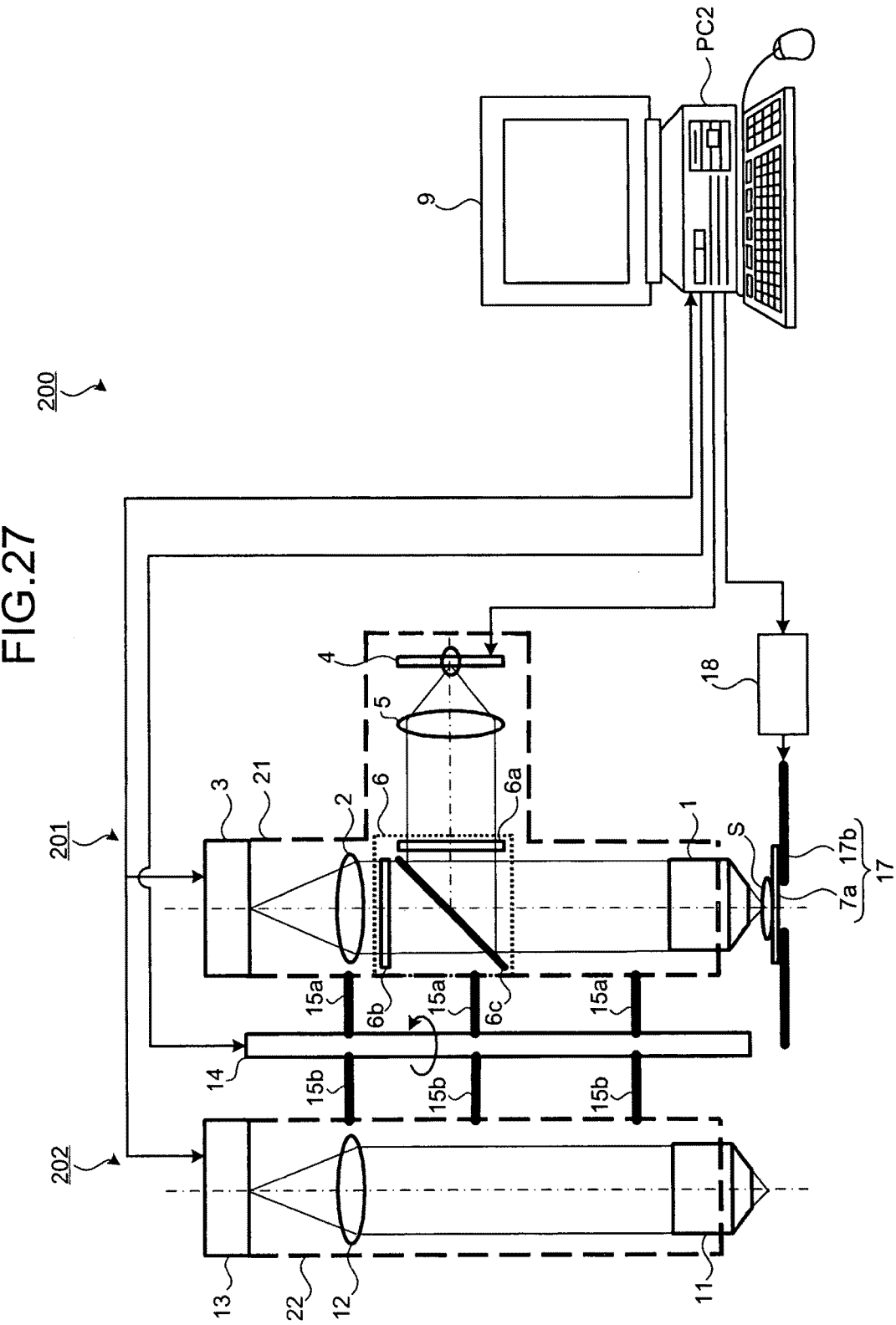
FIG. 27 is a diagram of the configuration of a microscope apparatus according to a second embodiment of the present invention.

FIG. 27 is a schematic diagram of the configuration of a microscope apparatus according to the second embodiment of the invention. As shown in FIG. 27, a microscope apparatus 200 in the second embodiment has a fluorescence microscope unit 201 and a the weak luminescence microscope unit 202 as with the microscope apparatus 100a, and further has a rotary drive unit 14, a fixed shaft 15a, and a fixed shaft 15b as optical system moving means in an intermediate position between the microscope units 201 and 202. Furthermore, the microscope apparatus 200 has a holding unit 17 having a movable stage 17b that has a smaller range of movement in place of the holding unit 7 included in the microscope apparatus 100a, and has a control device PC2 instead of the control device PC1. Other configurations are the same as those of the first embodiment, and the same numeral references are applied to the same structural parts.

The fluorescence microscope unit 201 includes a casing 21 that integrally holds each of the same structural parts as the fluorescence microscope units 101. The weak luminescence microscope unit 202 includes a casing 22 that integrally holds each of the same structural parts as the weak luminescence microscope unit 102a.

The rotary drive unit 14 includes an axis of rotation that passes through the midpoint of a line segment connecting substantially central points of the visual fields of a fluorescence imaging optical system included in the fluorescence microscope unit 201 and a weak luminescence imaging optical system included in the weak luminescence microscope unit 202, the axis of rotation being substantially parallel to the optical axis of each optical system. The rotary drive unit 14 rotates and moves the fluorescence microscope unit 201 and the weak luminescence microscope unit 202 held by the multiple fixed shafts 15a and 15b around the axis of rotation. Here, the fixed shafts 15a and 15b hold the casings 21 and 22, respectively.

The movable stage 17b moves the specimen S in an area approximately equal to the visual field of the weak luminescence imaging optical system. Further, the movable stage 17b is driven by a stage driving unit 18 in accordance with instructions from the control device PC2.

The control device PC2 controls the movement of the imaging devices 3 and 13, the excitation light source 4, and the stage driving unit 18 in the same manner as the control device PC1, and controls the movement of the rotary drive unit 14. The control device PC2 controls the rotary drive unit 14 to switch the arrangements of the fluorescence microscope unit 201 and the weak luminescence microscope unit 202 in switching the observation of weak luminescence to the observation of fluorescence.

Thus, according to the microscope apparatus 200 in the second embodiment, the fluorescence microscope unit 201 and the weak luminescence microscope unit 202 are rotated and moved by the rotary drive unit 14, and the observation of fluorescence is switched to the observation of weak luminescence. Therefore, the observation of fluorescence and the observation of weak luminescence can be switched immediately even when the specimen which cannot be moved at high speed, for example, the specimen immersed in a culture solution, is observed.

In this regard, in the microscope apparatus 200, the whole of each microscope unit 201, 202 is rotated and moved by the rotary drive unit 14. It may be configured that the imaging devices 3 and 13 are shared with one imaging device and the arrangement may be mutually switched by rotating and moving the portion obtained by excluding the imaging device 3 from the fluorescence microscope unit 201 and the portion obtained by excluding the imaging device 13 from the weak luminescence microscope unit 202.

Figure 28:
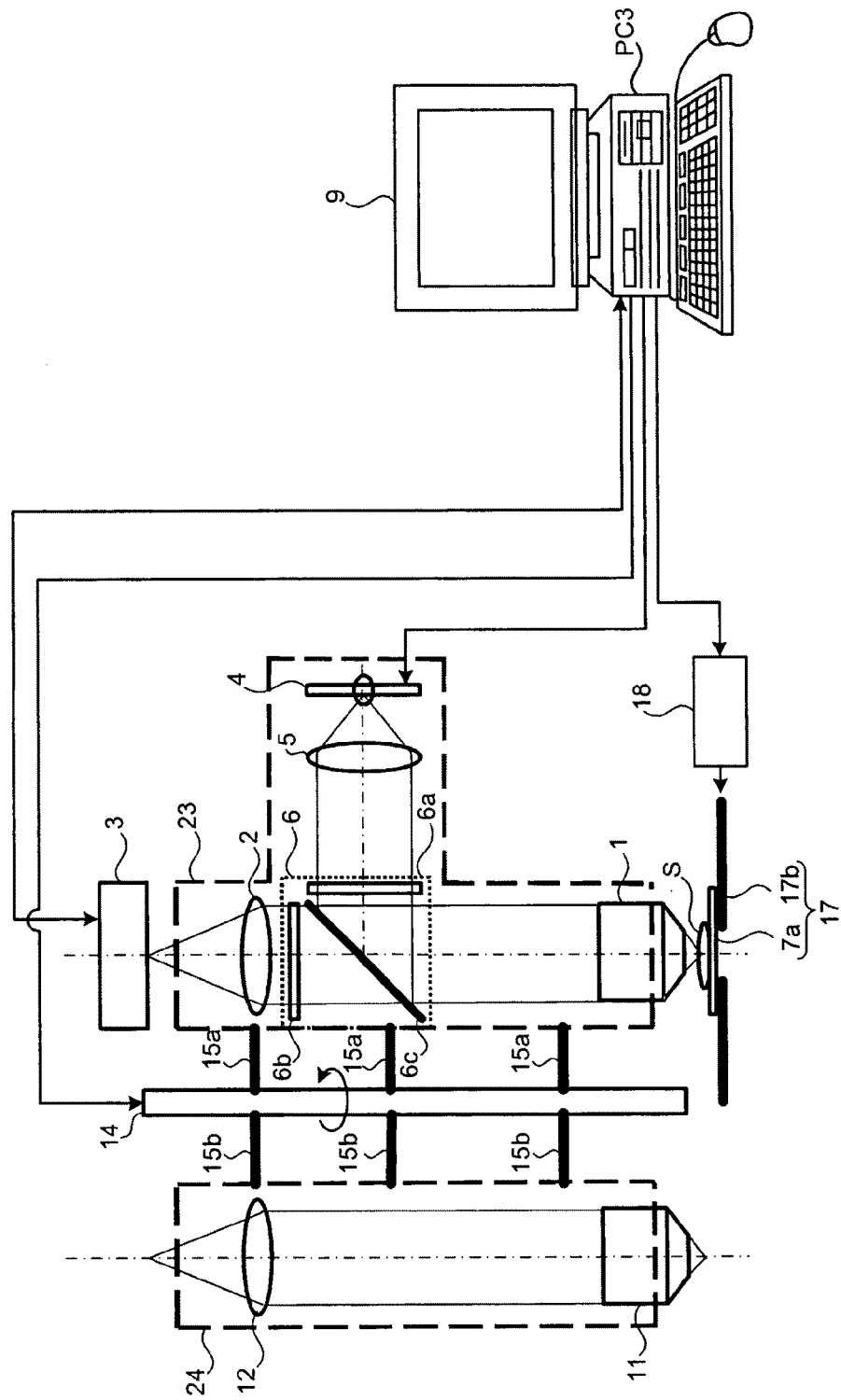
FIG. 28 is a diagram of the configuration of a modification of the microscope apparatus according to the second embodiment of the invention.

FIG. 28 is a schematic diagram of the configuration of a microscope apparatus thus configured. As shown in FIG. 28, a microscope apparatus 300 as the modification of the second embodiment removes the imaging device 13 from the microscope apparatus 200. The microscope apparatus 300 includes a casing 24 that integrally holds a weak luminescence imaging optical system in place of the casing 22 that integrally holds the whole weak luminescence microscope unit 202, and also includes a casing 23 that holds the portion obtained by excluding the imaging device 3 in place of the casing 21 that integrally holds the whole fluorescence microscope unit 201. The microscope apparatus 300 includes a control device PC3 in place of the control device PC2. Other configurations are the same as those of the microscope apparatus 200, and the same numeral references are applied to the same structural parts.

The control device PC3 controls the movement of the imaging device 3, the excitation light source 4, and the stage driving unit 18 as well as the movement of the rotary drive unit 14 in the same manner as the control device PC2. However, the control device PC2 switches the control of the imaging devices 3 and 13 depending on the observation of fluorescence and the observation of weak luminescence, while the control device PC3 controls the imaging device 3 to capture a specimen image in the case of both the observation of fluorescence and the observation of weak luminescence. At this time, the control device PC3 recognizes switching the range of the specimen image to be captured, the imaging magnification, and the like by the imaging device 3 depending on the observation of fluorescence and the observation of weak luminescence.

The rotary drive unit 14 holds the casings 23 and 24 by the fixed shafts 15a and 15b and switches the arrangement of the casings 23 and 24 in accordance with instructions from the control device PC3 depending on the observation of weak luminescence and the observation of fluorescence.

Thus, according to the microscope apparatus 300 as the modification of the second embodiment, the portion in which the imaging devices 3 and 13 are removed from the fluorescence microscope unit 201 and the weak luminescence microscope unit 202 is rotated and moved by the rotary drive unit 14, and the observation of fluorescence is switched to the observation of weak luminescence. Therefore, the weight of the moving section is reduced, so that movement and switching can be performed at a faster pace. Further, as for the microscope apparatus 300, the number of imaging devices is reduced compared with the microscope apparatuses 100a and 200. This allows for simplifying a circuit configuration related to the imaging device, reducing the processing load of the control device PC3, and speeding up the processing. An apparatus can be produced at low cost.

The microscope apparatuses 200 and 300 are configured such that the fluorescence microscope unit 201 and the weak luminescence microscope unit 202, or one part of each unit are rotated and moved by the rotary drive unit 14, while the arrangement of each unit 201 and 202 may be switched by, not limiting to the rotational movement, for example, moving the fluorescence microscope unit 201 and the weak luminescence microscope unit 202 in parallel along the movable stage 17b.

Third Embodiment

Next, a third embodiment of the present invention will be described. In the first and second embodiments described above, the fluorescence imaging optical system and weak luminescence imaging optical system that are arranged on the same side with respect to the specimen S and are independent are included. On the other hand, in the third embodiment, the fluorescence imaging optical system and weak luminescence imaging optical system that share a portion of optical systems are included.

Figure 29:
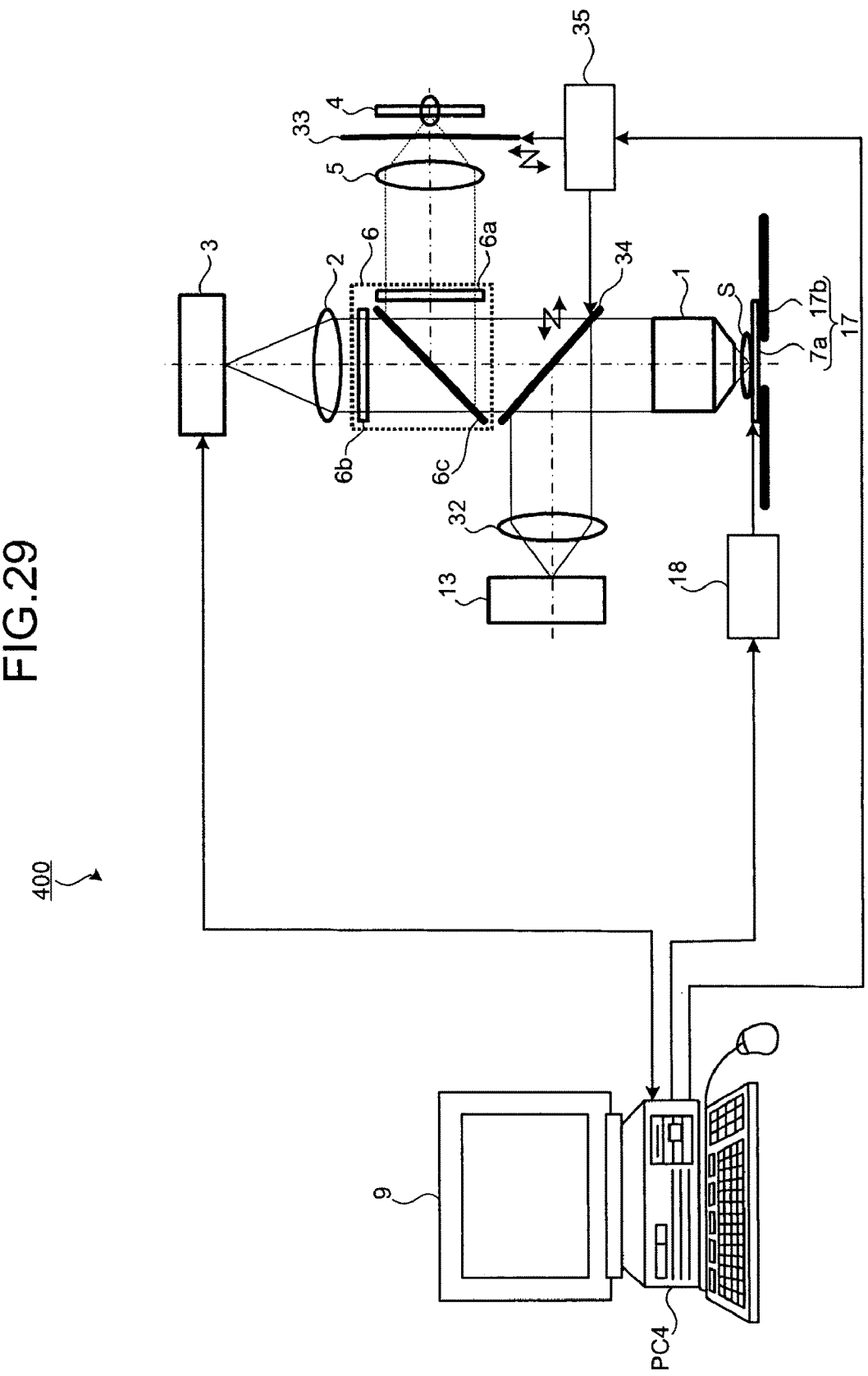
FIG. 29 is a diagram of the configuration of a microscope apparatus according to a third embodiment of the present invention.

FIG. 29 is a schematic diagram of the configuration of a microscope apparatus according to the third embodiment of the invention. As shown in FIG. 29, a microscope apparatus 400 according to the third embodiment shares the objective lenses of the fluorescence imaging optical system and the weak luminescence imaging optical system in which the microscope apparatus 100a separately includes and has an integrated microscope unit. Specifically, the microscope apparatus 400 includes the same microscope unit as the fluorescence microscope unit 101 included in the microscope apparatus 100a, and further includes a mirror 34 that is insertable and detachable between the objective lens 1 included in the microscope unit and the fluorescence cube 6. The microscope apparatus 400 also includes an imaging lens 32 in place of the imaging lens 12, and an imaging device 13 on the optical axis that is bent about 90 degrees leftwards in the drawing by the mirror 34.

Thus, the microscope apparatus 400 shares the objective lens 1 and has a fluorescence imaging optical system with the objective lens 1 and the imaging lens 2, and a weak luminescence imaging optical system with the objective lens 1 and the imaging lens 32. Further, the microscope apparatus 400 has the holding unit 17 and the stage driving unit 18 included in the microscope apparatus 200. The microscope apparatus 400 also has a shutter 33 as non-irradiating means between the excitation light source 4 and the lens 5, an optical path switch driving unit 35 that operates the shutter 33 and the mirror 34, and a control device PC4. Other configurations are the same as those of the first and second embodiments, and the same numeral references are applied to the same structural parts.

The control device PC4 controls the movement of the imaging devices 3 and 13 and the stage driving unit 18 in the same manner as the control device PC2, and controls the movement of the shutter 33 and the mirror 34 through the optical path switch driving unit 35. The control device PC4 removes the mirror 34 from between the objective lens 1 and the fluorescence cube 6, opens the shutter 33 and irradiates the specimen S with excitation light from the excitation light source 4 when switching from the observation of weak luminescence to the observation of fluorescence. On the other hand, the control device PC4 closes the shutter 33 so as to shield the excitation light from the excitation light source 4, does not irradiate the specimen S with the excitation light, inserts and arranges the mirror 34 on the optical path between the objective lens 1 and the fluorescence cube 6, and reflects the weak luminescence from the specimen S to the imaging lens 32 when switching from the observation of weak luminescence to the observation of fluorescence.

The imaging lens 32 has a focal length shorter than the imaging lens 2. The weak luminescence imaging optical system with the imaging lens 32 forms a weak luminescent specimen image at an imaging magnification lower than that of the fluorescence imaging optical system with the imaging lens 2. Further, it is desirable that the weak luminescence imaging optical system with the imaging lens 32 satisfies $(NAo'/\beta')^2 \geq 0.01$ when NA on the side of the specimen is defined as NAo' and an imaging magnification is defined as $\beta'$.

Thus, according to the microscope apparatus 400 in the third embodiment, it is configured to include a microscope unit that is integrated by the fluorescence imaging optical system and weak luminescence imaging optical system that share the objective lens. Therefore, miniaturization and simplification of the whole microscope apparatus can be achieved. Further, the moving section due to the switching of the observation of fluorescence and the observation of weak luminescence becomes a single optical element and the weight is reduced, so that movement and switching can be performed at a faster pace.

When the range of wavelengths of excitation light from the excitation light source 4 and fluorescence from the specimen S is different from the range of wavelengths of weak luminescence from the specimen S, a dichroic mirror that transmits excitation light and fluorescence and reflects weak luminescence may used in place of the mirror 34. In this case, the control device PC4 does not need to insert and detach a dichroic mirror in switching the fluorescent observation and the weak luminescent observation. When a dichroic mirror is used, the control device PC4 may control to perform the fluorescent observation and the weak luminescent observation at the same time.

Fourth Embodiment

Next, a fourth embodiment of the present invention will be described. In the first embodiment mentioned above, the fluorescence microscope unit 101 and the weak luminescence microscope unit 102a are arranged on the same side to the specimen S. On the other hand, in the fourth embodiment, the fluorescence microscope unit and the weak luminescence microscope unit are arranged on the opposite sides across the specimen S.

Figure 30:
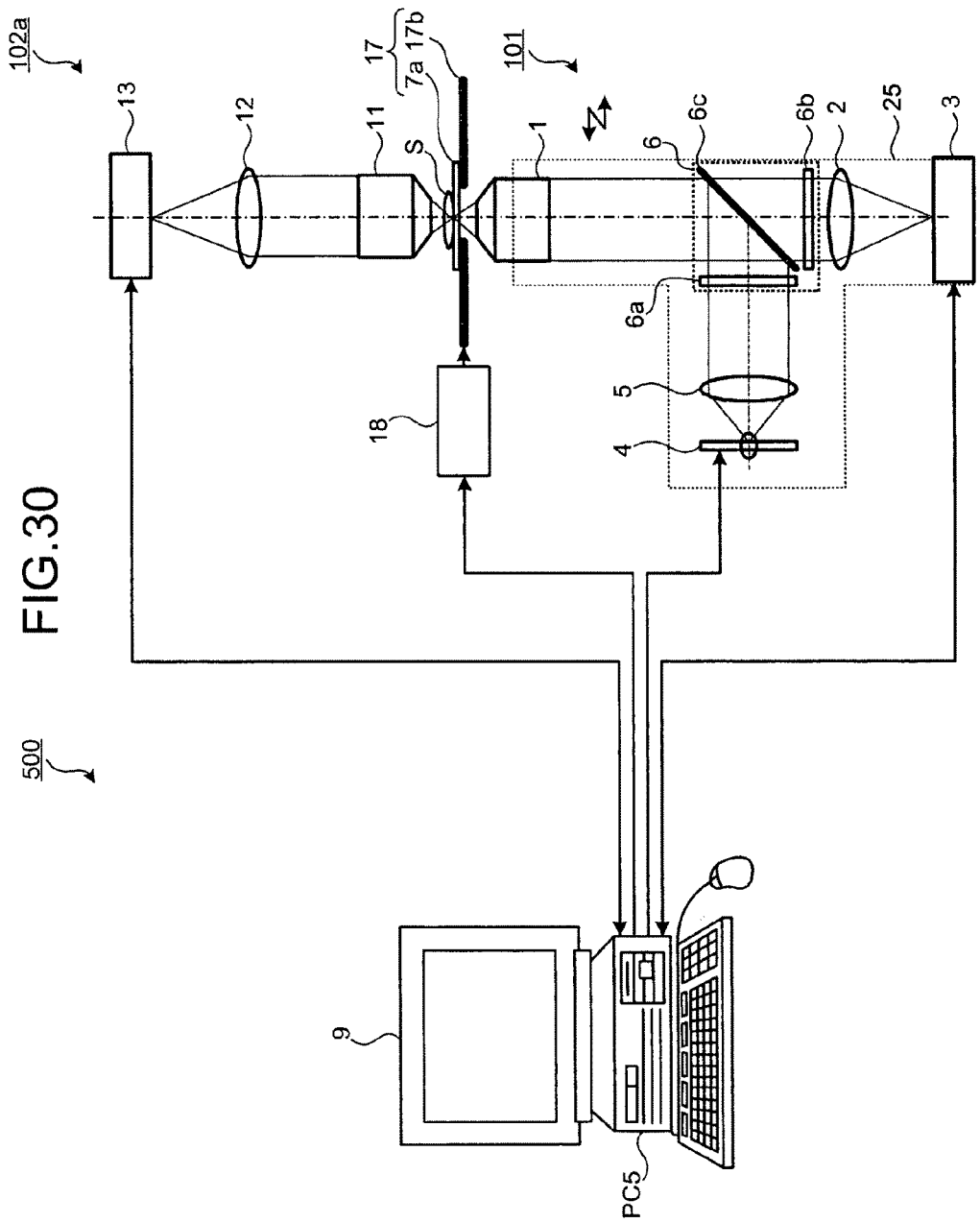
FIG. 30 is a diagram of the configuration of a microscope apparatus according to a fourth embodiment of the present invention.

FIG. 30 is a schematic diagram of the configuration of a microscope apparatus according to the fourth embodiment of the invention. As shown in FIG. 30, a microscope apparatus 500 according to the fourth embodiment includes the fluorescence microscope unit 101 and weak luminescence microscope unit 102a included in the microscope apparatus 100a and also includes the holding unit 1 and the stage driving unit 18 included in the microscope apparatus 200, and further includes a control device PC5 and a monitor 9. The same numeral references are applied to the same structural parts as that of the first and second embodiments.

In the microscope apparatus 500 shown in FIG. 30, the fluorescence microscope unit 101 is arranged on the downside of the specimen S (in the drawing) and the weak luminescence microscope unit 102a is arranged on the upside of the specimen S. Here, the up-and-down arrangement between respective units 101 and 102a may be reversed.

The control device PC5 controls the movement of the imaging devices 3 and 13, the excitation light source 4, and the stage driving unit 18 in the same manner as the control device PC2. When switching from the observation of weak luminescence to the observation of fluorescence, the control device PC5 turns on the excitation light source 4 to irradiate the specimen S with excitation light. When switching from the observation of fluorescence to the observation of weak luminescence, the control device PC 5 turns off the excitation light source 4 so as not to irradiate the specimen S with excitation light.

In this regard, a shading device such as a shutter 33 is provided on the optical path from the excitation light source 4 to the specimen S through the dichroic mirror 6c, and the control device PC5 may be configured to control irradiation and nonirradiation of excitation light by opening and closing the shading device instead of switching to turn on/off the excitation light source 4 as non-irradiating means.

Alternatively, when the range of wavelengths of excitation light from the excitation light source 4 and fluorescence from the specimen S is different from the range of wavelengths of weak luminescence from the specimen S, for example, a wavelength extracting filter that transmits weak luminescence and shields excitation light and fluorescence is provided between the imaging lens 12 and the imaging device 13. The control device PC5 may switch the observation of fluorescence and the observation of weak luminescence without turning off the excitation light source 4. Alternatively, in this case, the control device PC5 may control so that the observation of fluorescence and the observation of weak luminescence are performed at the same time.

Thus, according to the microscope apparatus 500 according to the fourth embodiment, the fluorescence microscope unit 101 and the weak luminescence microscope unit 102a are mutually arranged on the opposite sides across the specimen S. Consequently, the observation of fluorescence and the observation of weak luminescence can be switched immediately without mechanical driving.

The control device PC5 relatively may move the fluorescence microscope unit 101 to the weak luminescence microscope unit 102a along the movable stage 17b by a driving mechanism (not illustrated). In this case, while the wide range region of the specimen S is continued to be observed by the weak luminescence microscope unit 102a, an enlarged image of an arbitrary micro region in this wide range region can be observed by fluorescence microscope unit 101, and the observation of fluorescence and observation of weak luminescence can be performed without completely moving the specimen S.

Fifth Embodiment

Next, a fifth embodiment of the present invention will be described. In the first to fourth embodiments mentioned above, the specimen S is observed by weak luminescence and fluorescence from a luminescent label and a fluorescent label. On the other hand, in the fifth embodiment, the specimen S is observed by transmitted illumination.

Figure 31:
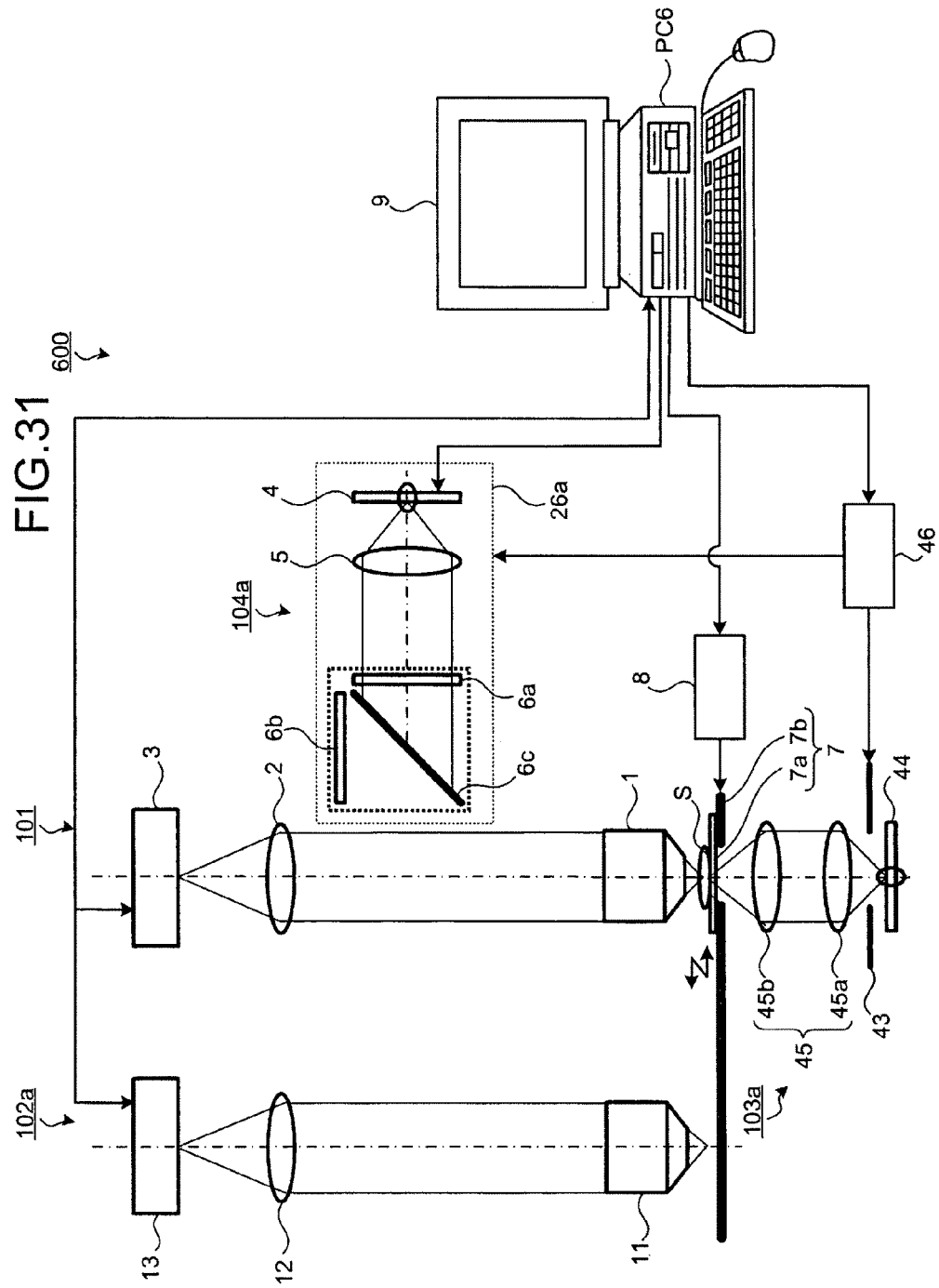
FIG. 31 is a diagram of the configuration of a microscope apparatus according to a fifth embodiment of the present invention.

FIG. 31 is a schematic diagram of the configuration of a microscope apparatus according to the fifth embodiment of the invention. As shown in FIG. 31, a microscope apparatus 600 according to the fifth embodiment includes a transmitted illumination unit 103a as illuminating means to perform transmitted illumination, an illumination driving unit 46 that drives a shutter 43 included in the transmitted illumination unit 103a, and a control device PC6 in place of the control device PC1 in addition to the microscope apparatus 100a in the first embodiment. Other configurations are the same as those of the first embodiment, and the same numeral references are applied to the same structural parts.

The transmitted illumination unit 103a includes a white light source 44 such as a halogen lamp that emits white light for transmitted illumination, a shutter 43 that switches irradiation and nonirradiation of white light, and an illuminating lens system 45 that concentrates white light from the white light source 44 on the specimen S and it is arranged on the opposite side to the fluorescence microscope unit 101 to the specimen S. The illuminating lens system 45 has a collector lens 45a and a condenser lens 45b and performs critical illumination to the specimen S. In this regard, the illuminating lens system 45 may perform Koehler illumination to the specimen S.

The illumination driving unit 46 drives the shutter 43 and a fluorescent lighting unit 104a in accordance with instructions of the control device PC6. Here, the fluorescent lighting unit 104a has the excitation light source 4, a lens 5, and a fluorescence cube 6 that are integrally held by a casing 26. The illumination driving unit 46 switches irradiation and nonirradiation of white light to the specimen S by opening and closing the shutter 43, and moves the fluorescent lighting unit 104a so that the fluorescence cube 6 is inserted and detached on the optical path between the objective lens 1 and the imaging lenses 2.

The control device PC6 controls the movement of the imaging devices 3 and 13, the excitation light source 4, and the stage driving unit 8 in the same manner as the control device PC1, and controls the movement of the illumination driving unit 46. When switching from the observation of fluorescence to the observation of transmitted illumination, the control device PC6 moves the fluorescent lighting unit 104a so as to remove the fluorescence cube 6 from between the objective lens 1 and the imaging lens 2, turns off the excitation light source 4, and opens the shutter 43, thereby performing transmitted illumination. When switching from the observation of transmitted illumination to the observation of fluorescence, the control device PC6 closes the shutter 43 and moves the fluorescent lighting unit 104a so that the fluorescence cube 6 is arranged between the objective lens 1 and the imaging lenses 2, thereby turning on the excitation light source 4.

When switching from the observation of weak luminescence to the observation of transmitted illumination, the control device PC6 drives the movable stage 7b by the stage driving unit 8 in addition to the control when switching from the observation of fluorescence to the observation of transmitted illumination, and controls to move the specimen S to the visual field of the fluorescence imaging optical system. The control device PC6 may turn on and off the white light source 44 instead of opening and closing the shutter 43.

It is described that the transmitted illumination unit 103a performs illumination for bright field observation, but it is not limited to the bright field observation. The transmitted illumination unit 103a may perform illumination for dark field observation, differential interference observation, or phase difference observation. Alternatively, the illumination for these various observations may be switchably included in the unit. When illumination for differential interference observation is performed, the transmitted illumination unit 103a may include a polarizer and a polarized light separating prism on the light source side of the condenser lens 45b, and a fluorescence imaging optical system may be configured so that a polarization synthetic prism and an analyzer are arranged in the pupil side of the objective lens 1. It is preferable that when performing illumination for phase difference observation, the transmitted illumination unit 103a is configured to have a ring slit on the light source side of the condenser lens 45b, and the fluorescence imaging optical system is configured so that a phase plate is arranged at an almost pupil position of the objective lens 1 or the objective lens 1 is switched to the objective lens having a phase plate. Further, it is preferable that when performing illumination for dark field observation, the transmitted illumination unit 103a may be configured to have a ring slit, or the like on the light source side of the condenser lens 45b.

The transmitted illumination unit 103a is arranged responsive to the fluorescence imaging optical system in order to perform the observation by transmitted illumination at high magnification, while it may be arranged responsive to the weak luminescence imaging optical system in order to observe at low magnification. Alternatively, it may be arranged responsive to both these imaging optical systems, or the arrangement may be properly switched for each imaging optical system.

Meanwhile, the microscope apparatus 600 is configured such that the transmitted illumination unit 103a and the illumination driving unit 46 are further included in the configuration of the microscope apparatus 100a, but it is not limited thereto. For example, as shown in FIGS. 32 to 34, the transmitted illumination unit 103a and the illumination driving unit 46 or the illumination driving unit 47 may be further included in each configuration of the microscope apparatuses 200, 300, and 400.

Figure 32:
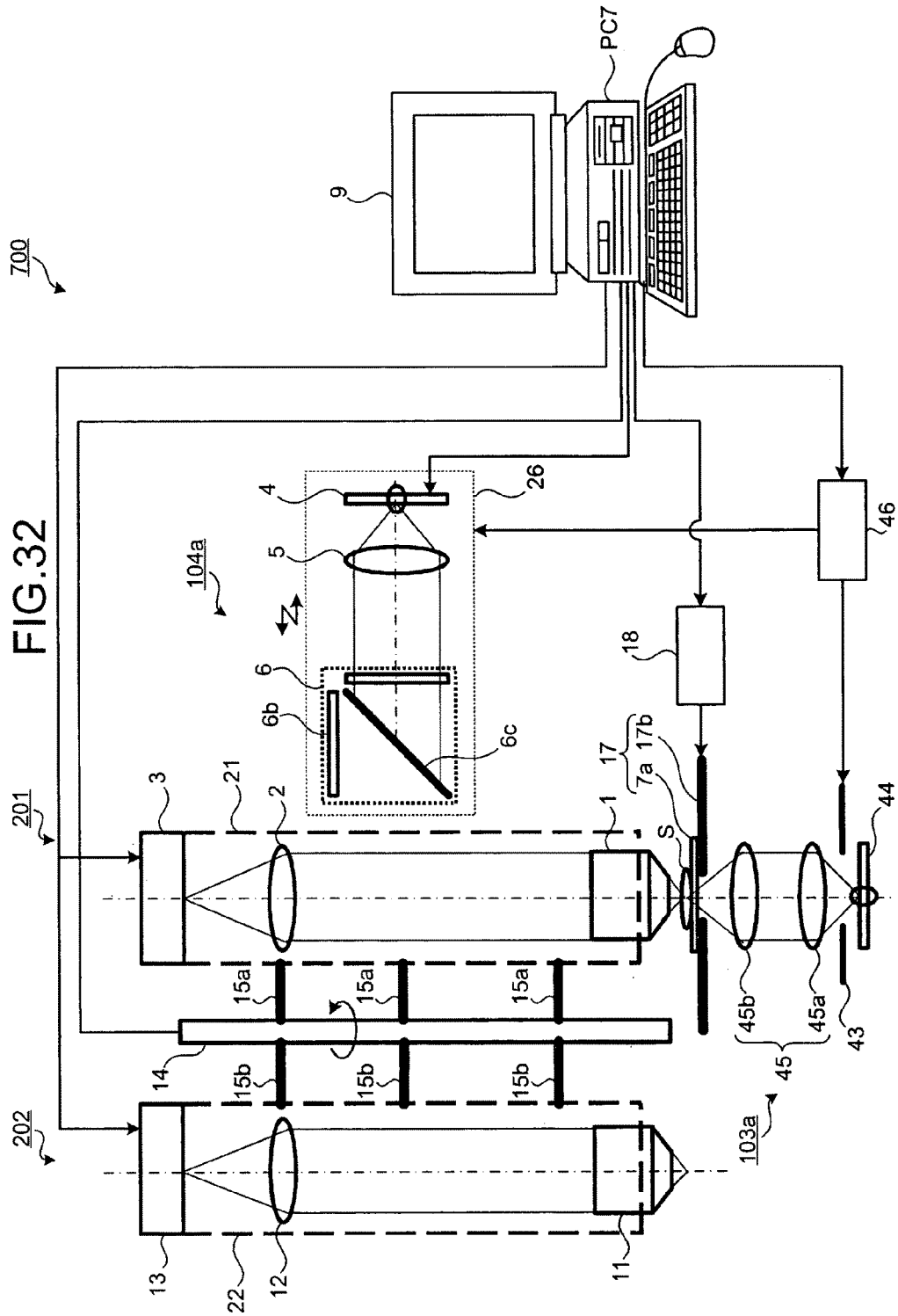
FIG. 32 is a diagram of the configuration of a modification of the microscope apparatus according to the fifth embodiment of the invention.

A microscope apparatus 700 shown in FIG. 32 is a case where the transmitted illumination unit 103a and the illumination driving unit 46 are further included in the configuration of the microscope apparatus 200. A control device PC7 controls the imaging devices 3 and 13, the excitation light source 4, the rotary drive unit 14, and the stage driving unit 18 in the same manner as the control device PC2, and controls the transmitted illumination unit 103a and the fluorescent lighting unit 104a by the illumination driving unit 46 in the same manner as the control device PC6.

Figure 33:
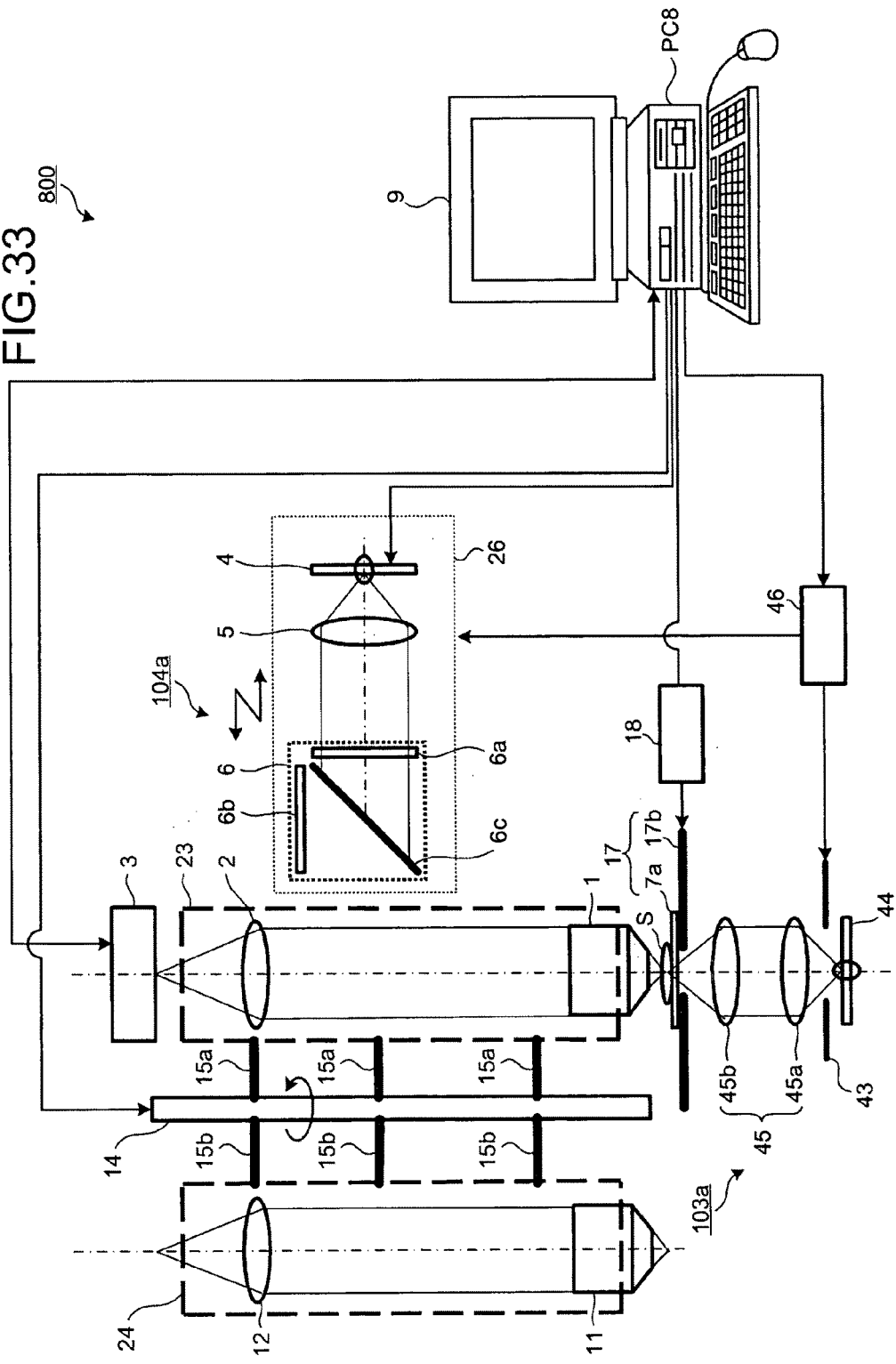
FIG. 33 is a diagram of the configuration of a modification of the microscope apparatus according to the fifth embodiment of the invention.

A microscope apparatus 800 shown in FIG. 33 is a case where the transmitted illumination unit 103a and the illumination driving unit 46 are further included in the configuration of the microscope apparatus 300. A control device PC8 controls the imaging devices 3, the excitation light source 4, the rotary drive unit 14, and the stage driving unit 18 in the same manner as the control device PC3, and controls the transmitted illumination unit 103a and the fluorescent lighting unit 104a by the illumination driving unit 46 in the same manner as the control device PC6.

Figure 34:
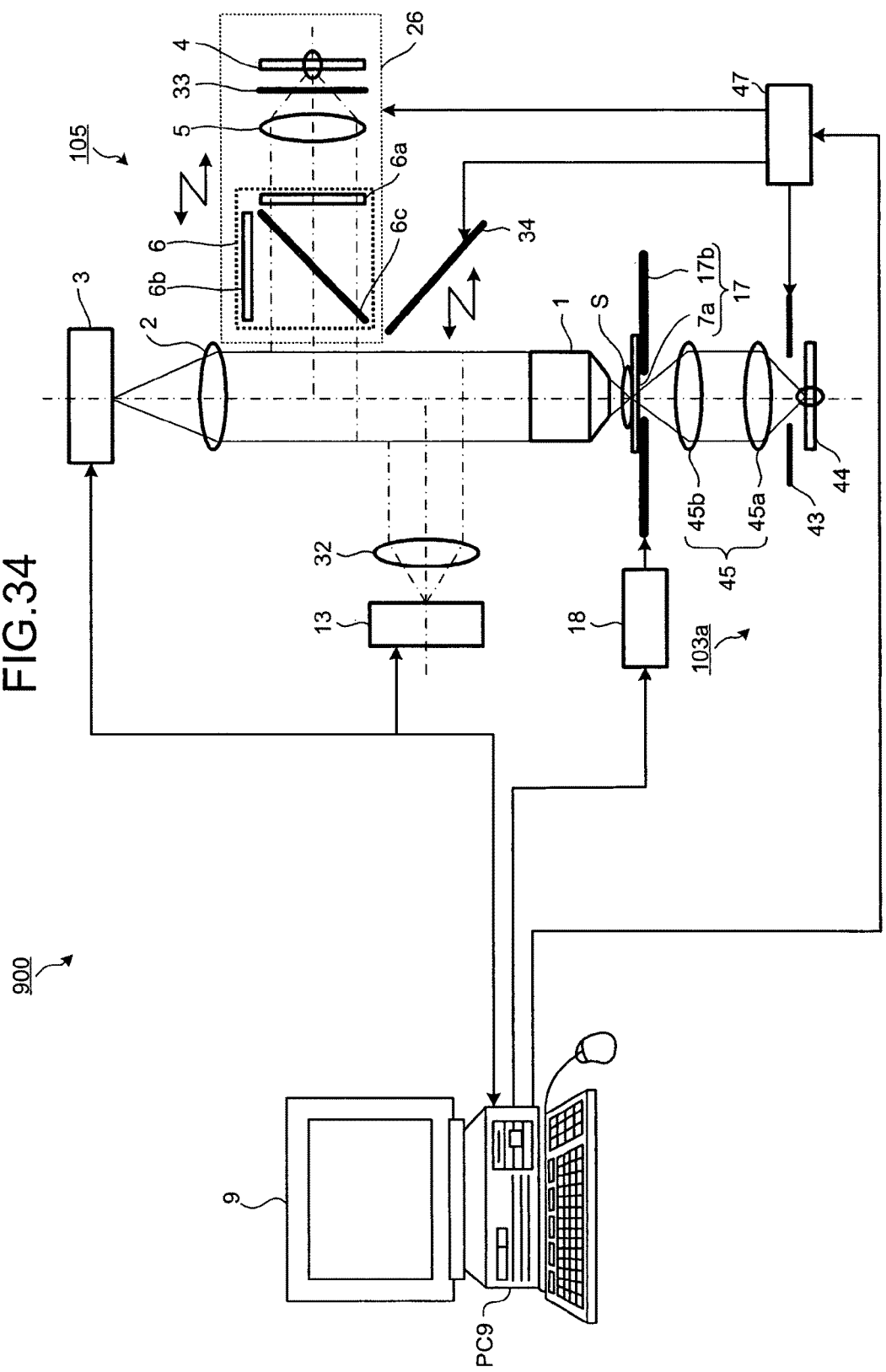
FIG. 34 is a diagram of the configuration of a modification of the microscope apparatus according to the fifth embodiment of the invention.

A microscope apparatus 900 shown in FIG. 34 is a case where the transmitted illumination unit 103a and the illumination driving unit 47 are further included in the configuration of the microscope apparatus 300. A control device PC9 controls the imaging devices 3 and 13, and the stage driving unit 18 in the same manner as the control device PC4, and controls the transmitted illumination unit 103a, the mirror 34, and the fluorescent lighting unit 105 by the illumination driving unit 47.

That is, when switching from the observation of fluorescence or the observation of weak luminescence to the observation of transmitted illumination, the control device PC9 moves the fluorescent lighting unit 105 so as to remove the fluorescence cube 6 from between the objective lens 1 and the imaging lens 2, and closes the shutter 33 not to irradiate with excitation light and opens the shutter 43 to perform transmitted illumination. When switching from the observation of transmitted illumination to the observation of fluorescence or weak luminescence, the control device PC9 closes the shutter 43 and moves the fluorescent lighting unit 105 or mirror 34 so that the fluorescence cube 6 or the mirror 34 is arranged between the objective lens 1 and the imaging lenses 2, thereby turning on the excitation light source 4. When the fluorescent observation is performed, the shutter 33 is opened to irradiate the specimen S with fluorescent light.

Thus, according to microscope apparatuses 600, 700, 800, and 900 in the fifth embodiment, the apparatuses are configured to correspond to at least one of a fluorescence imaging optical system and a weak luminescence imaging optical system, and include a transmitted illumination unit that performs transmitted illumination to the specimen S. Therefore, not only fluorescent and weak luminescent observations but also observations by various kinds of transmission illumination can be performed, and the specimen S can be observed from various angles.

The microscope apparatuses 100a, 200, 300, 400, 600, 700, 800, and 900 mentioned above are shown as upright microscope apparatuses, where they may be inverted microscope apparatuses. Further, the above-mentioned microscope apparatus can be preferably used in, for example, examinations of various types of reactions (for example, drug stimulation, or light exposure) or treatments.

As mentioned above, the embodiments have been described in detail. In the present invention, the term "luminescence" means that light may be generated by chemical reactions and the term includes particularly, bioluminescence and chemiluminescence as preferable examples. On the other hand, the term "fluorescence" means that light may be generated by excitation light. Here, BRET (bioluminescence resonance energy transfer) that is excited by the light energy due to bioluminescence is included in the term "luminescence" in the present invention since the dominant factor is the chemical reaction with a substrate solution. The luminescence generated from samples is an electromagnetic radiation with wavelengths between about 400 nm to about 900 nm that is less harmful to particularly living cells. In the image capture of the sample, it is necessary to use an optical power detector which detects a very low level light (usually, a single photon phenomenon) and can integrate with photon radiation until the construction of an image is attained. Examples of such a high sensitive photodetector include a camera or a camera group in which a single photon can be detected in unique background noise to the detection system after amplifying single photon phenomenon. For example, the CCD camera having an image sensor group like CCD can be illustrated. Generally, in some cases, a CCD camera is cooled with liquid nitrogen, and the like in order to obtain high sensitivity. It was confirmed by the present inventors that an image could be formed even when the cooling temperature is −5° C. to −20° C., preferably −5° C. to normal temperature in the case where an objective lens with a high numerical aperture (NA), especially, the optical condition represented by the square of numerical aperture (NA)/projecting magnification ($\beta$) is 0.01 or more is used. As a result of further examination, it is found out that when the square of the above-mentioned optical condition (NA/$\beta$) is 0.071 or more, a cell image that can be visually recognized 5 minutes or less or in some cases about 1 minute and can be analyzed can be provided. Generally, when the image capture time exceeds 30 minutes, it is difficult to obtain a clear luminescent image of live samples in many cases due to changes of the shape or the luminescence site. Therefore, the present invention provides the method and apparatus which obtain one luminescent image in a short time, particularly, 30 minutes or less, preferably, for 1 minute to 10 minutes and are advantageous to cooperate with fluorescence measurement that takes a short time to capture an image.

For example, as a related aspect, a series of images can be constructed by repeating the measurement of photon radiation or the image capture at the selected time interval when the localization of a fluorescent signal and/or the intensity of a luminescence signal serial is traced sequentially in order to record the distribution of the component compatible with the selected organism and/or the effect of a certain treatment to localization. The interval may be a short interval such as about several minutes, or a long interval such as about several days or several weeks. A luminescent image or a superposed image of fluorescence (or transmitted light) and luminescence can be expressed in various forms, such as a printed paper and an image in which graphics is processed.

As another related aspect, the present invention includes a method of monitoring the activity of a promoter induction event after detecting the presence of the promoter induction event in a transgenic animal or a chimera animal which are transformed with a construction containing the gene coding for a luminescent protein under the control of an inducible promoter. Examples of a promoter induction event include administration of the substance which directly activates the promoter, administration of the substance which stimulates the production of an endogenous promoter activator (for example, stimulation of the interferon produced by RNA virus infection), leaving in the state inducing the production of an endogenous promoter activator (for example, heat shock or stress), and the like.

As another aspect, the present invention also includes a method of identifying a compound for treatment which is effective in inhibiting that pathogenic infection becomes severe. In this method, a complex of a pathogen, a fluorescent component, and a luminescent component is administered to control animals and laboratory animals, or their cultured tissues (or cells) and the laboratory animals are treated with a candidate compound for treatment. After confirming the localization of a fluorescent signal in the samples to be measured by the above-mentioned method, a luminescent signal (bioluminescence or chemiluminescence) is continuously measured in the sample in which the localization is found. In this way, the therapeutic efficiency of the compound can be monitored.

Further, as another aspect, the present invention includes a method of passing a sample through media of various opacities, selecting the localized sample by a fluorescent signal, and then successively measuring the luminescence from the sample in which localization is confirmed. In this method, while an image can also be created by integrating a luminescent signal with photon which transmitted the medium, the method can be modified so that only the sample in which localization is confirmed is surgically removed from media (for example, organ tissue) and the luminescence of the removed sample is measured in suitable incubation atmosphere. The limited surgical operation (for example, biopsy) has the advantage that physical burden to original organisms (for example, mammals, especially humans) is reduced, and only required sample is placed in the stable environment for examination, so that the response to a variety of prospective medicines, the monitoring after the treatment, and preventive medicine test can be carried out for a long period of time.

As a further aspect, the present invention may include a method for measuring the concentration of the selected substance (for example, dissolved oxygen or calcium) at the predetermined site in a certain organism.

In the above description, according to the present invention, it is also possible to provide an analytical reagent for bioluminescence image analysis (or imaging analysis) as shown below. Especially, in the exemplary embodiments of the invention, a method, a reagent, and an apparatus for analyzing any biological activities (enzyme activity, immunological activity, molecular biological activity, genetic activity, and internal medicine activity etc.) of biological samples which mainly contain isolated cells or cell populations which do not contain opaque tissue, are provided. Here, the cells or cell populations which are isolated are stored in a storing container (for example, a well a petri dish, a microslide, a chip for microfluidics) that mainly consists of materials with high optical transparency for a long period of time. Therefore, unique reagents or reagent environments for minimizing the loss of intracellular activity or capturing without substantial inactivation are provided.

1. Reagents Regarding the Long-Term Use of Substrate and Handling Thereof.

When intracellular activity of the sample is maintained, for example, from several hours to 24 hours, from 2 to 6 days, 1 week to several weeks, or several weeks or more by a technique such as prolonged culture, handling with the following characteristics is important in order to produce luminescence. Some methods and/or reagents which will be described hereinbelow may be used alone. However, the invention is not limited thereto since in some cases, it is preferable to use several methods in combination.

(A First Handling Method)

Current reagents for bioluminescence, commercially available or reported, are substrates which can be used for observation up to 24 hours. However, when used for 24 hours or more, for example, several weeks, replenishment of a substrate is needed. A method of adding substrates to the culture medium in which cells or cell populations are placed at regular time intervals or in coincidence with the start of measurement is preferable. As a reagent kit suitable for adding several times, it is preferable to have holding means (container or bag) that includes a luminescent reagent containing a photoprotein that is enclosed in the same package and holding means (container or bag) that separately contains a substrate solution (or substrate-containing culture solution) with the amount corresponding to a luminescent reagent so as to be sufficient for using several times.

(A Second Handling Method)

In another aspect, PH adjustment is carried out over a long period of time. Thus, this method is a method of keeping concentration of $CO_2$ gas as gaseous environment at a constant concentration or more. More particularly, it is a method of maintaining a high concentration of gas which is higher level than the minimum level required for cells to survive. On the other hand, an apparatus is designed so that a sufficiently large volume of gaseous environment is stored in a storage container (for example, a gas tank) that stores a pressure more than atmospheric pressure and the gases travel from the container to cells (or cell populations) periodically or gradually. Preferably, the local movement of gaseous environment is set to the rate equivalent to the metabolic rate of cells (or cell populations) to gases.

(A Third Handling Method and Reagent)

HEPES, which is known to ensure a constant PH for a long time, is added. In the same manner as the case of the above-mentioned gaseous environment, HEPES can be supplied depending on the concentration of HEPES associated with the consumption rate of the solid, liquid, and gas which are consumed by cells (or cell populations). It is more preferable that HEPES is enclosed in a sustained-release capsule, publicly known, and an effective number of capsules is contained in a solution or a culture medium together with cells (or cell populations). The solution and culture medium which mainly contain a sustained-release capsule in which an effective amount of HEPES (or a compound for maintaining a PH equivalent to HEPES) is enclosed can become an effective reagent for achieving the objective of the present invention.

(A Fourth Handling Method, Apparatus or Reagent)

According to the spirit of the present invention, there is provided an apparatus for keeping warm and/or a medicament for adjusting internal temperature of cells or cell populations to the level that does not cause a fatal change.

(A Fifth Handling Method or Reagent)

This description relates to a method and/or a reagent for keeping the background of luminescence detections low over a long period of time. Namely, a method of removing a tissue fragment, a coloring matter (for example, a chromogenic dye substance, especially phenol red dye) as an element related to the increase in the background by bioluminescence (or chemiluminescence) can be provided, or a culture medium or solution in which such elements are sufficiently removed in advance can be provided as a reagent.

(A Sixth Handling Method or Reagent)

Passing a substrate through cells, particularly cell populations, is important in the stability of luminescence or measurement accuracy. As this method, a treatment that helps the substrate penetrate cell membrane (for example, a pressure shock or an electric shock) can be carried out continuously and intermittently or depending on the aging of cells. The substrate or special buffer solution which contains an additive which supports or facilitates the cell membrane permeability (for example, a surfactant as a membrane lytic substance, salts as membrane osmotic pressure modified substances) can be provided as a reagent. Preferably, these methods and/or reagents are set so that the permeability to a fresh extracellular substrate can be maintained without shortage of active substrates in cells during long-term measurements or the permeability is temporarily increased.

(A Seventh Handling Method)

This description relates to a method for achieving uniform staining. Magnetic beads are added in advance and then stirring is carried out for several hours or once a day. Usually, cells are stuck on the bottom of a container to be charged, and therefore it is preferable to first stir the upper layer of the container.

(An Eighth Handling Method or Reagent)

When long-term observations are carried out, byproducts are generated by repeatedly performing many luminescent reactions in the same cell (or cell population), which cause optical inhibition or chemical inhibition. This description relates to a method or reagent for eliminating influence of such inhibition. That is, the reaction byproducts generated by luminescent reaction are accumulated depending on the handling such as replenishment of a substrate. In order to remove the byproducts (pyrophoric acid) caused by this luminescent reaction, substances to eliminate byproducts (for example, metal ions which produce precipitation) are added.

(A Ninth Handling Method or Reagent)

This description relates to a method or reagent for regenerating luciferin as a luminescent component. After emitting light as a result of luciferase reaction, luciferin is converted to oxyluciferin. A method of supplying a reagent to convert oxyluciferin to luciferin to cells (or cell populations) in accordance with aging or loss of luciferin is provided. In the case of a firefly, it is known that the detected oxyluciferin is converted into nitrile 2 and then it reacts with cysteine in the body as used in the synthesis, thereby regenerating luciferin. It is also possible to provide a substrate containing a regenerative material to regenerate the decreased activity of such a luminescent component or a special buffer solution. Other examples of the substrate include coelenterazine.

(A Tenth Handling Method or Reagent)

This description relates to an encapsulation substrate as a novel reagent. A suitable substrate (for example, luciferin) is enclosed in a capsule that is eluted or released after a predetermined time or at regular time intervals in order to maintain a given concentration of the substrate. Further, a method for providing a substrate (for example, luciferin) which is not enclosed in a capsule and the same kind of substrate which is enclosed in a capsule at the same time, or a reagent which is a solution contained in the capsule in a mixed state can be provided. Furthermore, there is an advantage that a fresh substrate can be automatically provided at different release times by adding a reagent in which the same kind of substrate (for example, luciferin) is contained in two or more capsules with a different rate of gradual release (or contacting with a culture medium) together with cells (or cell populations) at the same time. In this way, the timing when excitation light is irradiated can be coordinated with the timing when substrate is released.

Example 1

Figure 10:
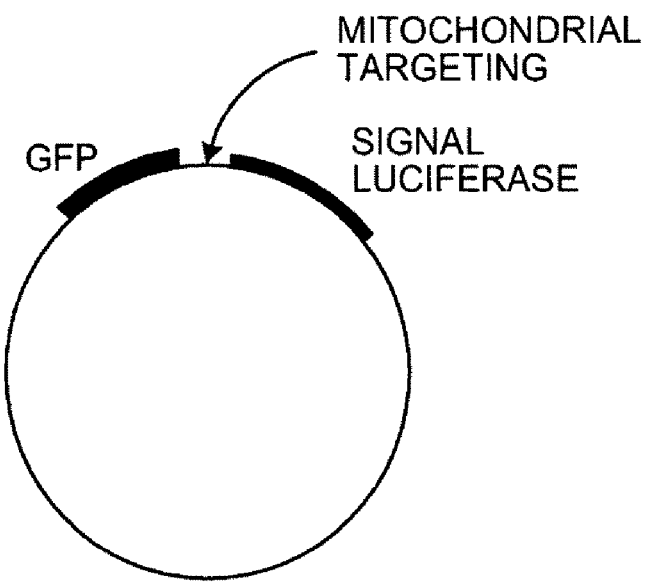
FIG. 10 is a view of a plasmid vector fused with GFP, a mitochondrial targeting signal, and luciferase.

Here, the amounts of luminescence and ATP from mitochondria in specific HeLa cells are measured sequentially in multiple HeLa cells into which the plasmid vector shown in FIG. 10 is introduced using the predetermined site luminescence measuring apparatus 100 in the embodiment described above.

First, an experimental protocol in Example 1 will be described.

(1) A fusion gene in which a fluorescence protein (GFP), a mitochondrial targeting signal, and luciferase are linked is prepared.

(2) A plasmid vector containing a fusion gene (refer to FIG. 10) is introduced into a HeLa cell.

Figure 11:
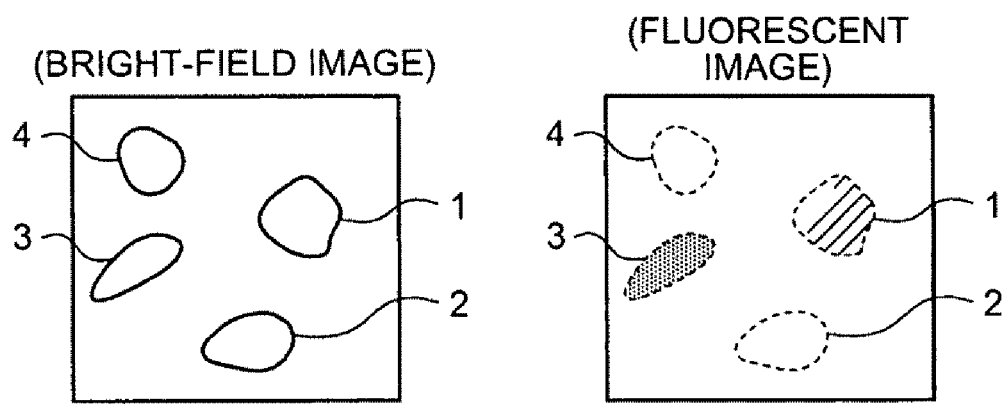
FIG. 11 is a view of a bright-field image and a fluorescent image of a HeLa cell into which the plasmid vector is introduced, which are captured by the fluorescent image capturing unit 108.

(3) Localization of luciferase in mitochondria is confirmed by determining whether GFP is localized in the mitochondria using the predetermined site luminescence measuring apparatus 100 (specifically, an inverted fluorescence microscope forming the apparatus) in the embodiment described above (refer to FIG. 11). FIG. 11 is a view of the bright-field image and fluorescent image of a HeLa cell into which the plasmid vector is introduced, which are captured by the fluorescent image capturing unit 108 forming the predetermined site luminescence measuring apparatus 100.

(4) Histamine is administered to HeLa cells to induce changes in the amount of ATP in mitochondria through $Ca^{2+}$.

Figure 12:
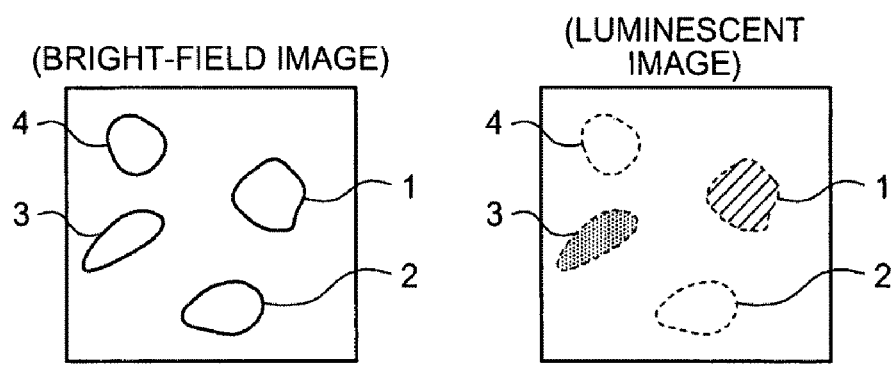
FIG. 12 is a view of a bright-field image and a luminescent image of a HeLa cell into which the plasmid vector is introduced, which are captured by the luminescent image capturing unit 106.

(5) The luminescence emitted from mitochondria is sequentially obtained as an image using the predetermined site luminescence measuring apparatus 100 in the embodiment described above (refer to FIG. 12). FIG. 12 is a view of the bright-field image and luminescent image of a HeLa cell into which the plasmid vector is introduced, which are captured by the luminescent image capturing unit 106 forming the predetermined site luminescence measuring apparatus 100.

(6) The cells to be measured are selected by superimposing a bright-field image on a fluorescence image or a luminescence image using the predetermined site luminescence measuring apparatus 100 in the embodiment described above.

Figure 13:
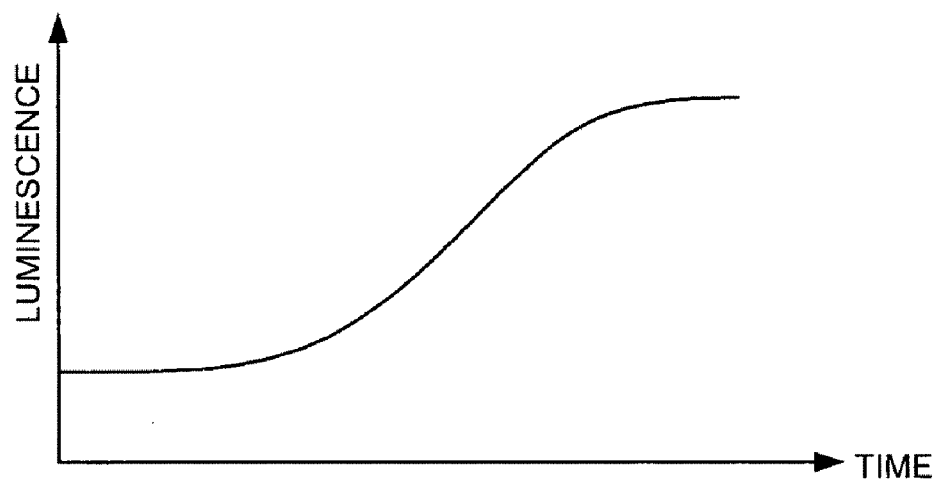
FIG. 13 is a graph of an example of changes over time in luminescence intensity of a specified HeLa cell.

(7) The luminescence intensity of the selected cells or regions is sequentially measured (refer to FIG. 13) and changes in the amount of ATP are monitored using the predetermined site luminescence measuring apparatus 100 in the embodiment described above. FIG. 13 is a view of changes over time in the luminescence intensity of the specified HeLa cell No. 1 which is measured with the predetermined site luminescence measuring apparatus 100.

Next, experimental results will be described. As shown in FIG. 11, as for the HeLa cell No. 1, it was found that the fusion gene was introduced by the plasmid vector and luciferase was localized in mitochondria. Further, as for in HeLa cells No. 2 and 4, it was found that a fusion gene was not introduced by the plasmid vector. Furthermore, as for a HeLa cell No. 3, it was found that a fusion gene was introduced by the plasmid vector, but luciferase was not localized in mitochondria. In this regard, a HeLa cell in which the introduction of a fusion gene by the plasmid vector and the localization of luciferase in mitochondria were both found was the HeLa cell No. 1 only, and therefore the HeLa cell for measurement was identified as the HeLa cell No. 1. As shown in FIG. 12, it was confirmed that luminescence from the HeLa cell No. 3 was the strongest, luminescence from the HeLa cell No. 1 was the second strongest, and the strength of luminescence from the HeLa cell No. 2 is equal to that from the HeLa cell No. 4. As shown in FIG. 13, the time course of the luminescence intensity from mitochondria of the HeLa cell No. 1 could be monitored by using the predetermined site luminescence measuring apparatus 100.

Example 2

In this Example, luminescence and fluorescence of the HeLa cells are observed in the HeLa cells into which luciferase genes and green fluorescence protein (GFP) genes were introduced using the predetermined site luminescence measuring apparatus 100 of the embodiment described above, as shown in FIG. 16.

First, an experimental protocol in Example 2 will be described.

(1) The luciferase gene and the green fluorescence protein (GFP) genes are tandemly arrayed and then a vector (EGFP-Luc: manufactured by Clonetech) is located, which is introduced into HeLa cells by the Lipofectin method.

(2) About 24 hours after the introduction of the vectors, 500 µM of luciferin is added to a culture solution (D-MEM, GIBCO: manufactured by Invitrogen) containing the HeLa cells into which the vectors are introduced.

Figure 16:
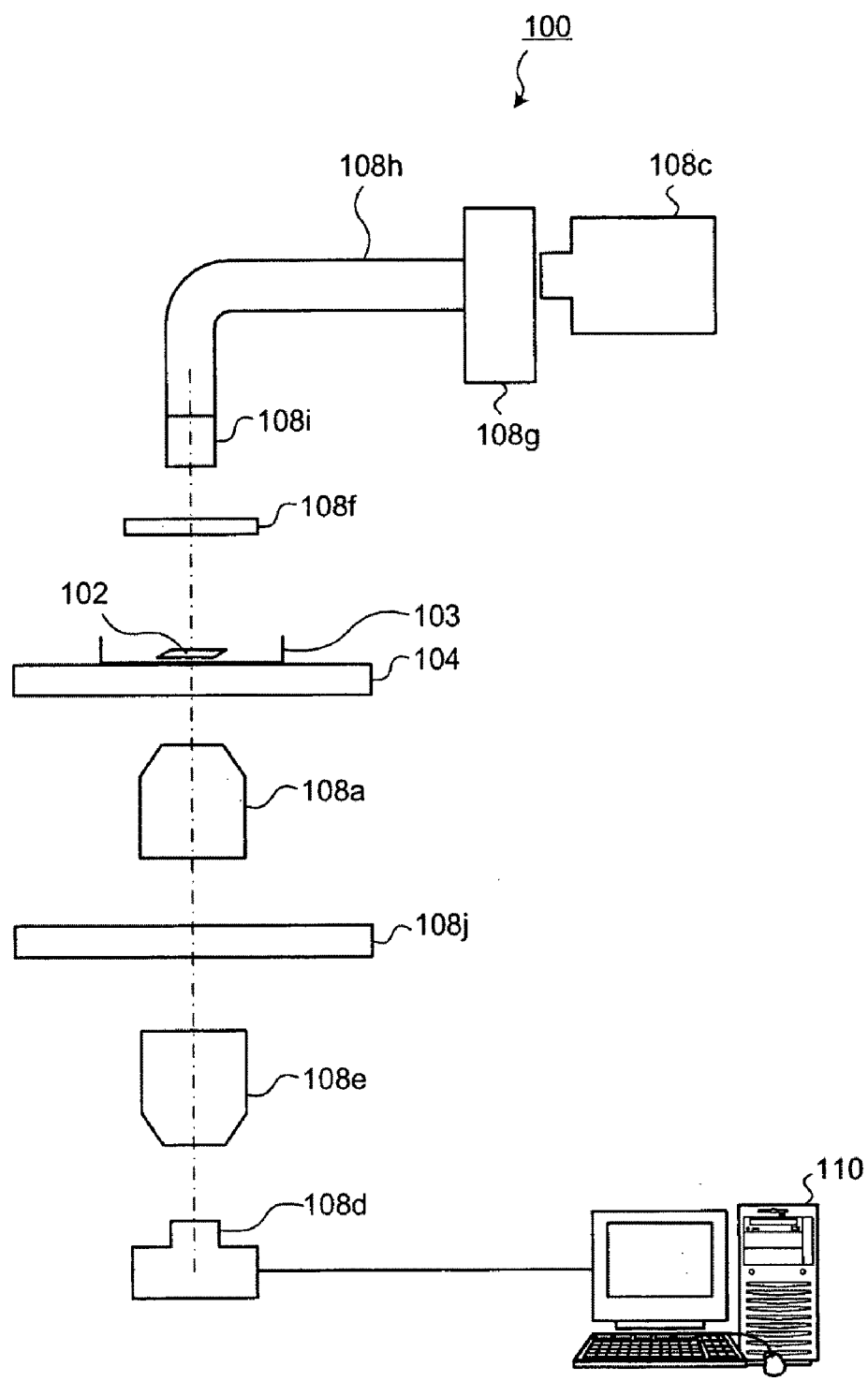
FIG. 16 is a diagram of an example of the entire configuration of the predetermined site luminescence measuring apparatus 100.

(3) A container to which the culture solution is added is placed on the stage 104 of the predetermined site luminescence measuring apparatus 100 as shown in FIG. 16 and then the bright-field image, fluorescent image, and luminescent image of the HeLa cells are captured using the predetermined site luminescence measuring apparatus 100. When a fluorescent image was captured, a spectral filter for excitation 108g and a filter for luminescence and fluorescence spectra 108j were placed and exposure time in the image capturing was 0.7 seconds. When capturing a luminescent image, the filter for luminescence and fluorescence spectra 108j was removed and the exposure time in the image capturing was 5 minutes. Here, in Example 2, "Uapo 20X: manufactured by Olympus Corporation" that has a focal length (f) of 9 mm and a Numerical Aperture (NA) of 0.75 was used as an objective lens 108a. Further, "LMPlanFL 10X: manufactured by Olympus Corporation" having a focal length (f) of 18 mm, a Numerical Aperture (NA) of 0.25, and the value of 0.035 found by "$(NA/\beta)^2$" was used as an imaging lens 108e. A halogen light source "LG-PSs: manufactured by Olympus Corporation" was used as a light source 108c. "DP-30BW: manufactured by Olympus Corporation" was used as a CCD camera 108d. "BP470-490: manufactured by Olympus Corporation" was used as the spectral filter for excitation 108g. Furthermore, "510AF23: manufactured by Omega" was used as the filter for luminescence and fluorescence spectra 108j.

Figure 17:
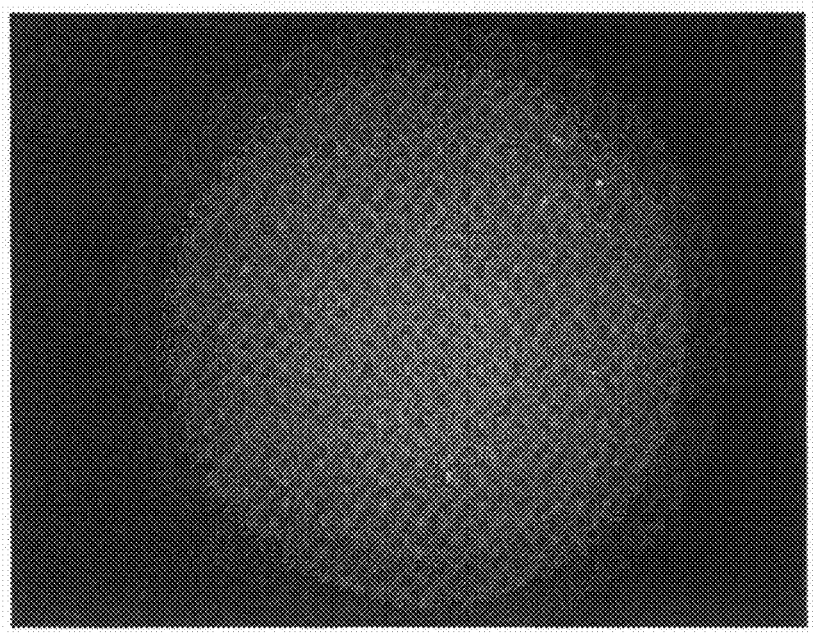
FIG. 17 is a view of a fluorescent image of a HeLa cell into which an EGFP-Luc gene is introduced.
Figure 18:
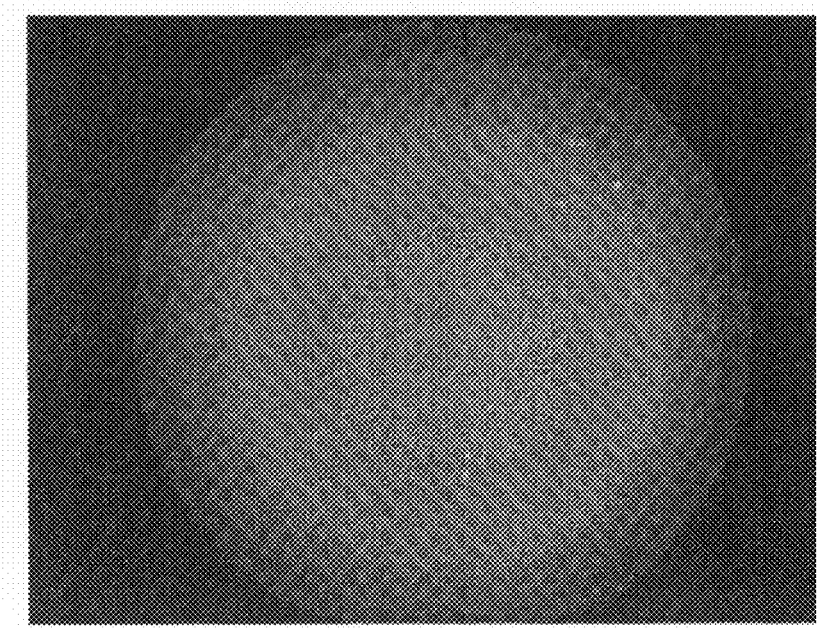
FIG. 18 is a view of an image obtained by overlapping a bright-field image and the fluorescent image of the HeLa cell into which the EGFP-Luc gene is introduced.
Figure 19:
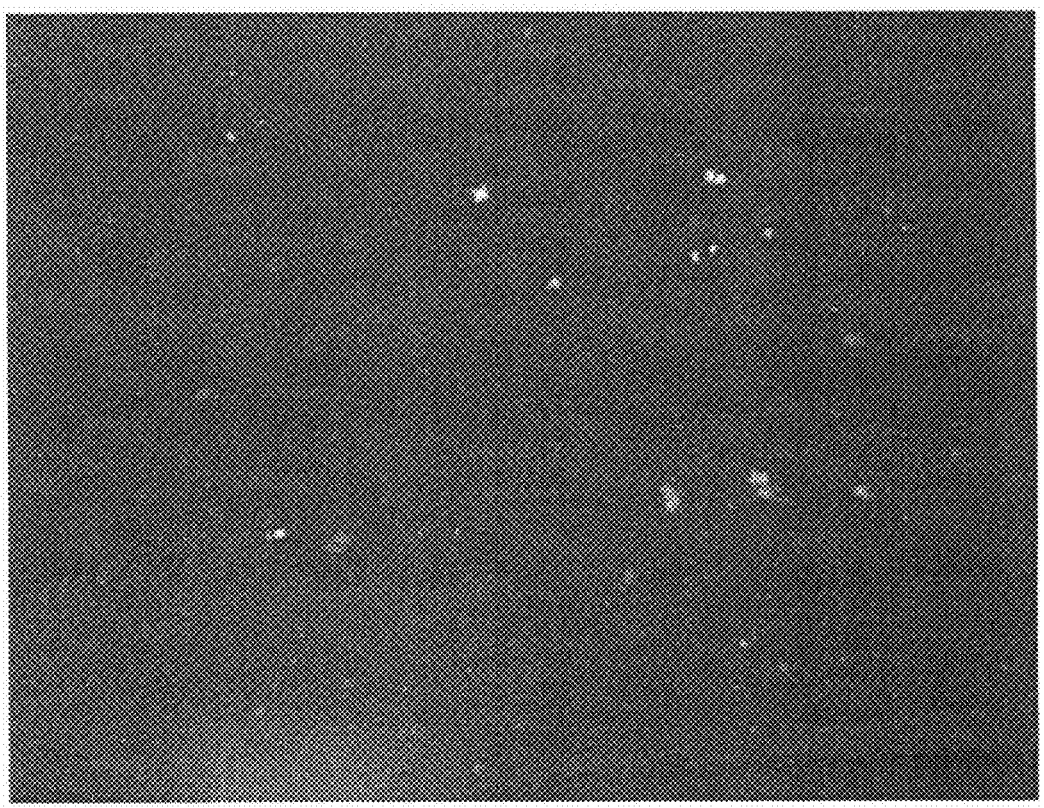
FIG. 19 is a view of a luminescent image of the HeLa cell into which an EGFP-Luc gene is introduced.

Next, the results of observation will be described. FIG. 17 is a view of the fluorescent image of a HeLa cell into which a vector (EGFP-Luc gene) is introduced. FIG. 18 is a view of superimposed images of the fluorescent image and bright-field image of the HeLa cell into which the vector (EGFP-Luc gene) is introduced. FIG. 19 is a view of the luminescent image of the HeLa cell into which the vector (EGFP-Luc gene) is introduced. As shown in FIGS. 17, 18, and 19, the transfected HeLa cells could be specified by fluorescent observation using the predetermined site luminescence measuring apparatus 100, and further the specified HeLa cells were focused and then the luminescent image could be captured.

Example 3

In this example, the amount of expression of the gene to be analyzed is measured by luminescence (promoter assay for the gene to be analyzed), while the stage of the cell cycle is identified by fluorescence using the expression amount measuring apparatus 1000 as described in the embodiments.

First, vectors to be introduced into cells are produced. Specifically, the cell cycle-related gene promoter containing luciferase (green) expression vector is produced. The type of cells to be used is PC12. Next, the produced vectors are transfected into cells (transfection). Then, the cell membrane of the cell is stained with "PKH LinkerKits (red): manufactured by SIGMA". Thereafter, promoter assay of the cell cycle-related gene, the gene to be analyzed, is performed while the stage of the cell cycle is identified using the expression amount measuring apparatus 1000. Thus, the relationship between the cell cycle and morphology of cells could be examined.

Example 4

In this example, the amount of expression of the gene to be analyzed is measured by fluorescence and the expression period of the genes and the localization of the genes are identified, while the stage of the cell cycle is identified by luminescence using the expression amount measuring apparatus 1000 as described in the embodiments.

First, vectors to be introduced into cells are produced. Specifically, the fluorescent protein vector into which the gene promoter for analysis is introduced is produced. Then, HaloTag (registered trademark) vector (manufactured by Promega KK) is introduced into cells. The type of cells to be used is PC12. Cells are labeled with luciferase by adding HaloTag (registered trademark) ligand (manufactured by Promega KK) thereto. That is, cells are luciferase-labeled by the ligand binding to HaloTag (registered trademark) (manufactured by Promega KK). Then, the expression period of the gene to be analyzed which can be involved in the cell cycle and their localization are identified while the stage of the cell cycle is monitored using the expression amount measuring apparatus 1000. This allowed for evaluating whether there is a relationship between the gene to be analyzed and the cell cycle, and the usefulness of the gene to be analyzed as a cell-cycle marker.

INDUSTRIAL APPLICABILITY

As described above, the predetermined site luminescence measuring method, and the predetermined site luminescence measuring apparatus in the present invention are useful when measuring the luminescence from the predetermined site in living samples. In addition, the expression amount measuring method in the present invention is useful when measuring the amount of expression in the gene to be analyzed which are introduced into living cells as well as identifying the stage of the cell cycle, and can be advantageously used in various fields such as biotechnology, medicine manufacture, and medical care.

The invention claimed is:

1. A predetermined site luminescence measuring method for measuring the luminescence from a live sample into which a fusion gene is introduced, the fusion gene being obtained by fusing a targeting base sequence that directs a photoprotein to a predetermined site in the sample and a luminescence-related gene that expresses the photoprotein, in order to obtain the amount of luminescence from the predetermined site, wherein the fusion gene is obtained by further fusing a fluorescence-related gene that expresses a fluorescence protein with the targeting base sequence, and the luminescence-related gene, the method comprising:

a fluorescent image capturing step of capturing a fluorescent image of the sample into which the fusion gene is introduced, the fluorescent image capturing step performed by a fluorescent image acquiring unit;

a determining step of determining whether the photoprotein is localized at the predetermined site based on the fluorescent image captured at the fluorescent image capturing step, the determining step performed by a determining unit; and a luminescence measuring step of measuring the luminescence from the sample when the localization is determined as a result of the determining step, the luminescence measuring step performed by a luminescence measuring unit.

2. The predetermined site luminescence measuring method according to claim 1, further comprising:

a luminescent image capturing step of, when multiple live samples into which the fusion gene is introduced are present in an area to be captured, capturing a luminescent image of the samples, the luminescent image capturing step performed by a luminescent image acquiring unit; and a selecting step of selecting a sample for measurement from the samples in which the localization is determined as the result of the determining step by superimposing the fluorescent image captured at the fluorescent image capturing step and the luminescent image captured at the luminescent image capturing step, the selecting step performed by a selecting unit, wherein the fluorescent image capturing step includes capturing the fluorescent image of the samples, the determining step includes determining whether the photoprotein is localized at the predetermined site based on the fluorescent image for each sample, and the luminescence measuring step includes measuring the luminescence from the sample selected at the selecting step.

3. The predetermined site luminescence measuring method according to claim 2, wherein the amount of luminescence from the predetermined site in the sample is obtained sequentially by repeatedly performing the fluorescent image capturing step, the determining step, the luminescent image capturing step, the selecting step, and the luminescence measuring step.

4. The predetermined site luminescence measuring method according to claim 1, further comprising a luminescence separation step of separating luminescence from the sample in accordance with luminescent color, wherein multiple fusion genes to be introduced into the samples are prepared in advance so that each combination of a targeted site to which the photoprotein is directed by the targeting base sequence, a luminescent color of luminescence emitted from the photoprotein, and a fluorescent color of fluorescence emitted from the fluorescence protein is different, the determining step includes determining whether a photoprotein is localized at the predetermined site for each fluorescent color based on the fluorescent image, and the luminescence measuring step includes, when the localization is determined as a result of the determining step, specifying luminescence from the site where the localization is determined among the multiple luminescence separated at the luminescence separation step, and measuring the specified luminescence.

5. The predetermined site luminescence measuring method according to claim 1, wherein the sample is any one of a test sample, a tissue, a cell, and an individual.

6. The predetermined site luminescence measuring method according to claim 3, further comprising an ATP quantifying step of quantifying ATP at the predetermined site in the samples selected at the selecting step based on the amount of luminescence measured at the luminescence measuring step, the ATP quantifying step performed by a related substance quantifying unit, wherein the sample is a cell, the predetermined site is mitochondria, the targeting base sequence is a mitochondrial targeting signal, the photoprotein is luciferase, and the fluorescence protein is a green fluorescent protein, and ATP at the predetermined site in the sample is quantified sequentially by repeatedly performing the fluorescent image capturing step, the determining step, the luminescent image capturing step, the selecting step, the luminescence measuring step, and the ATP quantifying step.

7. A predetermined site luminescence measuring apparatus that measures the luminescence from a live sample into which a fusion gene is introduced, the fusion gene being obtained by fusing a targeting base sequence that directs a photoprotein to a predetermined site in the sample and a luminescence-related gene that expresses the photoprotein, in order to obtain the amount of luminescence from the predetermined site, wherein the fusion gene obtained by further fusing a fluorescence-related gene that expresses a fluorescence protein with the targeting base sequence, and the luminescence-related gene, the apparatus comprising:

a fluorescent image capturing unit that captures a fluorescent image of the sample into which the fusion gene is introduced;

a determining unit that determines whether the photoprotein is localized at the predetermined site based on the fluorescent image captured by the fluorescent image capturing unit; and a luminescence measuring unit that measures the luminescence from the sample when the localization is determined as a result of the determining unit.

8. An expression amount measuring method comprising:

a luminescence measuring step of measuring luminescence intensity of luminescence emitted from a living cell into which a luminescence-related gene which expresses a photoprotein, a fluorescence-related gene which expresses a fluorescence protein, and a gene to be analyzed are introduced, the luminescence measuring step performed by a luminescence measuring unit;

a fluorescence measuring step of measuring fluorescence intensity emitted from the cell, the fluorescence measuring step performed by a fluorescence measuring unit; and an expression amount measuring step of measuring the amount of expression of the gene to be analyzed based on the luminescence intensity measured at the luminescence measuring step or the fluorescence intensity measured at the fluorescence measuring step, the expression amount measuring step performed by an expression measuring unit, wherein the cell is a cell into which a cell cycle-related gene which expresses at a predetermined stage of the cell cycle is further introduced in addition to the luminescence-related gene, the fluorescence-related gene, and the gene to be analyzed, the method further comprising a stage identifying step of identifying the stage of the cell cycle by determining the presence or absence of the expression of the cell cycle-related gene based on the fluorescence intensity measured at the fluorescence measuring step when the luminescence intensity is used at the expression amount measuring step, or based on the luminescence intensity measured at the luminescence measuring step when the fluorescence intensity is used at the expression amount measuring step, the stage identifying step performed by a stage identifying unit.

9. The expression amount measuring method according to claim 8, further comprising:

a fluorescent image capturing step of, when multiple cells are present in an area to be captured, capturing a fluorescent image of the cells, the fluorescent image capturing step performed by a fluorescent image acquiring unit; and a luminescent image capturing step of capturing a luminescent image of the cells, the luminescent image capturing step performed by a luminescent image acquiring unit, wherein the luminescence measuring step includes measuring luminescence intensity of luminescence emitted from each cell based on the luminescent image captured at the luminescent image capturing step, the fluorescence measuring step includes measuring fluorescence intensity emitted from each cell based on the fluorescent image captured at the fluorescent image capturing step, the expression amount measuring step includes measuring the amount of expression of the gene to be analyzed in each cell based on the luminescence intensity measured at the luminescence measuring step or the fluorescence intensity measured at the fluorescence measuring step, and the stage identifying step identifies the stage of the cell cycle for each cell by determining the presence or absence of the expression of the cell cycle-related gene for each cell based on the fluorescence intensity measured at the fluorescence measuring step when the luminescence intensity is used at the expression amount measuring step, or based on the luminescence intensity measured at the luminescence measuring step when the fluorescence intensity is used at the expression amount measuring step.

10. The expression amount measuring method according to claim 9, further comprising a selecting step of selecting the cell for measurement from among the cells whose stages are identified at the stage identifying step, the selecting step performed by a selecting unit, wherein the expression amount measuring step includes measuring the amount of expression of the gene to be analyzed which is introduced into the cells selected at the selecting step, based on the luminescence intensity measured at the luminescence measuring step or the fluorescence intensity measured at the fluorescence measuring step.

11. The expression amount measuring method according to claim 10, wherein the amount of expression of the gene to be analyzed is measured sequentially by repeatedly performing the luminescent image capturing step, the fluorescent image capturing step, the luminescence measuring step, the fluorescence measuring step, the stage identifying step, the selecting step, and the expression amount measuring step while the stage of the cell cycle is identified in the cells selected at the selecting step.

12. The expression amount measuring method according to claim 11, wherein the expression amount measuring step includes measuring the amount of expression of the gene to be analyzed in the cell selected at the selecting step based on the fluorescence intensity measured at the fluorescence measuring step, and identifying an expression site of the gene to be analyzed in the cell based on the fluorescent image captured at the fluorescent image capturing step.

13. An expression amount measuring method, comprising:

a luminescence measuring step of measuring luminescence intensity of luminescence emitted from cells in a living cell into which a luminescence-related gene which expresses a photoprotein and a gene to be analyzed are introduced, the luminescence measuring step performed by a luminescence measuring unit; and an expression amount measuring step of measuring the amount of expression of the gene to be analyzed based on the luminescence intensity measured at the luminescence measuring step, the expression amount measuring step performed by an expression measuring unit, wherein the cell is stained with a fluorescent substance at the predetermined site, the method further comprising:

a fluorescent image capturing step of capturing a fluorescent image of the cell, the fluorescent image capturing step performed by a fluorescent image acquiring unit; and a stage identifying step of identifying the stage of the cell cycle by determining whether the shape of the cell is changed or not based on the fluorescent image captured at the fluorescent image capturing step the stage identifying step performed by a stage identifying unit.

14. The expression amount measuring method according to claim 13, further comprising a luminescent image capturing step of, when multiple cells are present in an area to be captured, capturing a luminescent image of the cells, the luminescent image capturing step performed by a luminescent image acquiring unit, wherein the fluorescent image capturing step includes capturing a fluorescent image of the cells, the luminescence measuring step includes measuring luminescence intensity of luminescence emitted from each cell based on the luminescent image captured at the luminescent image capturing step, the expression amount measuring step includes measuring the amount of expression of the gene to be analyzed in each cell based on the luminescence intensity measured at the luminescence measuring step, and the stage identifying step includes identifying the stage of the cell cycle by determining whether the shape of the cell is changed or not based on the fluorescent image captured at the fluorescent image capturing step.

15. The expression amount measuring method according to claim 14, further comprising a selecting step of selecting the cell for measurement from among the cells whose stages are identified at the stage identifying step, the selecting step performed by a selecting unit,
wherein the expression amount measuring step includes measuring the amount of expression of the gene to be analyzed which is introduced into cells selected at the selecting step, based on the luminescence intensity measured at the luminescence measuring step.

16. The expression amount measuring method according to claim 15, wherein the amount of expression of the gene to be analyzed is measured sequentially by repeatedly performing the luminescent image capturing step, the fluorescent image capturing step, the luminescence measuring step, the stage identifying step, the selecting step, and the expression amount measuring step while the stage of the cell cycle is identified in the cells selected at the selecting step.

17. A measuring apparatus comprising: an imaging optical system which forms a specimen image of a specimen which is labeled with a luminescent label emitting luminescence and a fluorescent label emitting fluorescence by excitation and held by a holding unit; and a capturing unit that captures the specimen image,
wherein the specimen is a living cell into which a luminescence-related gene which expresses a photoprotein as the luminescent label and a fluorescence-related gene which express a fluorescence protein as the fluorescent label are introduced,
wherein the imaging optical system includes: a weak luminescence imaging optical system that forms the specimen image of luminescence from the luminescent label as a luminescent specimen image; and a fluorescence imaging optical system that forms the specimen image of fluorescence from the fluorescent label as a fluorescent specimen image, and
the capturing unit captures the luminescent specimen image and the fluorescent specimen image.

18. The measuring apparatus according to claim 17, wherein the fluorescence imaging optical system comprises an illuminating unit that illuminates the specimen.

19. The measuring apparatus according to claim 17, comprising an image capture switch controlling unit that makes a control to switch between the capturing of the luminescent specimen image and the capturing of the fluorescent specimen image, based on an image characteristic of the luminescent specimen image captured by the capturing unit.

20. The measuring apparatus according to claim 19, wherein the image characteristic is image intensity of the luminescent specimen image, and
the image capture switch controlling unit switches from the capturing of the luminescent specimen image to the capturing of the fluorescent specimen image when the image intensity is higher than a predetermined threshold.

21. The measuring apparatus according to claim 20, wherein the image intensity is the image intensity of all or part of the luminescent specimen image, and is cumulative image intensity from a predetermined time point up to a current time point or current image intensity.

22. The measuring apparatus according to claim 19, wherein the fluorescence imaging optical system comprises:
a fluorescence objective lens that converts fluorescence from each point of the fluorescent label into a substantially parallel pencil of rays;
a fluorescence imaging lens that concentrates the fluorescence converted into the substantially parallel pencil of rays by the fluorescence objective lens to form the fluorescent specimen image;
a fluorescence unit including: an excitation light transmitting filter which selectively transmits excitation light that excites the fluorescent label; a fluorescence transmitting filter which selectively transmits the fluorescence from the fluorescent label; and a dichroic mirror which reflects the excitation light and transmits the fluorescence, the fluorescence unit being arranged between the fluorescence objective lens and the fluorescence imaging lens; and
an excitation light irradiating unit including an excitation light source that emits the excitation light, the excitation light irradiating unit reflecting the excitation light from the excitation light source by the dichroic mirror to irradiate the specimen with the excitation light.

23. The measuring apparatus according to claim 22, wherein the weak luminescence imaging optical system comprises:
a weak luminescence objective lens that converts luminescence from each point of the luminescent label into a substantially parallel pencil of rays; and
a weak luminescence imaging lens that concentrates the luminescence converted into the substantially parallel pencil of rays by the weak luminescence objective lens to form the luminescent specimen image.

24. The measuring apparatus according to claim 22, wherein the weak luminescence imaging optical system and the fluorescence imaging optical system are mutually arranged on the opposite sides across the specimen,
the excitation light irradiating unit includes a non-irradiating unit that does not irradiate the specimen with excitation light, and
the image capture switch controlling unit controls the non-irradiating unit not to irradiate the specimen with excitation light when causing the capturing unit to capture a luminescent specimen, and controls the excitation light irradiating unit to irradiate the specimen with excitation light when causing the capturing unit to capture a fluorescent specimen image.

25. The measuring apparatus according to claim 24, comprising a visual field moving unit that moves the visual fields of the weak luminescence imaging optical system and the fluorescence imaging optical system relatively and parallel to each other.

26. The measuring apparatus according to claim 24, wherein the holding unit includes a specimen transferring unit that transfers the specimen to each visual field of the weak luminescence imaging optical system and the fluorescence imaging optical system.

27. The measuring apparatus according to claim 23, wherein the weak luminescence objective lens and the fluorescence objective lens are the same lens, and
the weak luminescence imaging optical system and the fluorescence imaging optical system share the objective lens.

28. The measuring apparatus according to claim 27, further comprising: a mirror which is insertably and detachably arranged in a pupil space between the objective lens and the fluorescence unit, the mirror reflecting luminescence from the objective lens to the weak luminescence imaging lens when arranged in the pupil space, wherein the excitation light irradiating unit includes a non-irradiation unit that does not irradiate the specimen with excitation light, and the image capture switch controlling unit arranges the mirror in the pupil space and controls the non-irradiating unit not to irradiate with excitation light when causing the capturing unit to capture a luminescent specimen image, and arrange the mirror out of the pupil space and controls the excitation light irradiating unit to irradiate with excitation light when causing the capturing unit to capture a fluorescent specimen image.

29. The measuring apparatus according to claim 22, wherein the weak luminescence imaging optical system and the fluorescence imaging optical system are arranged on the same side with respect to the specimen, the holding unit includes a specimen transferring unit that transfers the specimen to each visual field of the weak luminescence imaging optical system and the fluorescence imaging optical system, and the image capture switch controlling unit controls the specimen transferring unit to transfer the specimen to the visual field of the weak luminescence imaging optical system when causing the capturing unit to capture a luminescent specimen image, and controls the specimen transferring unit to transfer the specimen to the visual field of the fluorescence imaging optical system when causing the capturing unit to capture a fluorescent specimen image.

30. The measuring apparatus according to claim 22, further comprising an optical system moving unit that moves the weak luminescence imaging optical system and the fluorescence imaging optical system so that the visual fields of the weak luminescence imaging optical system and the fluorescence imaging optical system cover the specimen, wherein the weak luminescence imaging optical system and the fluorescence imaging optical system are arranged on the same side with respect to the specimen, and the image capture switch controlling unit controls the optical system moving unit to move the weak luminescence imaging optical system so that the visual field of the weak luminescence imaging optical system covers the specimen when causing the capturing unit to capture a luminescent specimen image, and controls the optical system moving unit to move the fluorescence imaging optical system so that the visual field of the fluorescence imaging optical system covers the specimen when causing the capturing unit to capture a fluorescent specimen image.

31. The measuring apparatus according to claim 30, wherein the optical system moving unit includes an axis of rotation that passes through the midpoint of a line segment connecting substantially central points of the visual fields of the weak luminescence imaging optical system and the fluorescence imaging optical system and is substantially parallel to the optical axis of each of the weak luminescence imaging optical system and the fluorescence imaging optical system, the optical system moving unit rotating and moving the weak luminescence imaging optical system and the fluorescence imaging optical system around the axis of rotation.

32. The measuring apparatus according to claim 17, wherein the capturing unit includes: a weak luminescence capturing unit that captures the luminescent specimen image; and a fluorescence capturing unit that captures the fluorescent specimen image.

33. The measuring apparatus according to claim 30, wherein the capturing unit includes: a weak luminescence capturing unit that captures the luminescent specimen image; and a fluorescence capturing unit that captures the fluorescent specimen image, and the optical system moving unit integrally moves the weak luminescence imaging optical system and the weak luminescence capturing unit as well as the fluorescence imaging optical system and the fluorescence capturing unit.

34. The measuring apparatus according to claim 30, wherein the luminescent specimen image and the fluorescent specimen image are formed in substantially the same position by the weak luminescence imaging lens and the fluorescence imaging lens, respectively, and the capturing unit is fixed in a position substantially corresponding to the position where the luminescent specimen image and the fluorescent specimen image are formed.

35. The measuring apparatus according to claim 27, further comprising an illuminating unit that corresponds to at least one of the weak luminescence imaging optical system and the fluorescence imaging optical system, for transmit illumination to the specimen.

36. The measuring apparatus according to claim 35, wherein the transmitted illumination is at least one of illumination for bright field observation, illumination for dark field observation, illumination for differential interference observation, and illumination for phase contrast observation.

37. The measuring apparatus according to claim 17, wherein the weak luminescence imaging optical system has a value calculated by $(NAo/\beta)^2$ of 0.01 or more, where NAo is a numerical aperture on the side of the specimen of the weak luminescence imaging optical system, and $\beta$ is a magnification for forming the luminescent specimen image.

* * * * *